US012260939B2

(12) United States Patent
Garcia et al.

(10) Patent No.: US 12,260,939 B2
(45) Date of Patent: Mar. 25, 2025

(54) SYSTEMS AND METHODS FOR PREDICTING COMPOUNDS ASSOCIATED WITH TRANSCRIPTIONAL SIGNATURES

(71) Applicant: Cellarity, Inc., Somerville, MA (US)

(72) Inventors: Juan Corchado Garcia, Cambridge, MA (US); Ragy Haddad, Cambridge, MA (US); Diogo Camacho, Sudbury, MA (US)

(73) Assignee: CELLARITY, INC., Somerville, MA (US)

( * ) Notice: Subject to any disclaimer, the term of this patent is extended or adjusted under 35 U.S.C. 154(b) by 0 days.

(21) Appl. No.: 18/539,190

(22) Filed: Dec. 13, 2023

(65) Prior Publication Data

US 2024/0194299 A1 Jun. 13, 2024

Related U.S. Application Data

(60) Provisional application No. 63/387,251, filed on Dec. 13, 2022.

(51) Int. Cl.
*G06N 20/20* (2019.01)
*G16B 5/00* (2019.01)
*G16B 20/00* (2019.01)
*G16B 40/20* (2019.01)

(52) U.S. Cl.
CPC .............. *G16B 40/20* (2019.02); *G06N 20/20* (2019.01); *G16B 5/00* (2019.02); *G16B 20/00* (2019.02)

(58) Field of Classification Search
CPC ........ G16B 40/20; G16B 40/30; G16B 15/30; G16B 5/00; G01N 33/6803; G01N 33/6893; G01N 33/6848; G01N 2500/00; G01N 2500/04; G01N 2800/52; G01N 30/8686;
(Continued)

(56) References Cited

U.S. PATENT DOCUMENTS

2020/0020419 A1 1/2020 Kahvejian

FOREIGN PATENT DOCUMENTS

| CN | 115666563 A | * | 1/2023 | ........... A61K 31/519 |
| WO | WO-2022084495 A1 | * | 4/2022 | ......... G06Q 30/0278 |
| WO | WO-2022155597 A2 | * | 7/2022 | |

OTHER PUBLICATIONS

Agresti, An Introduction to Categorical Data Analysis, 1996, Chapter 5, pp. 103-144, John Wiley & Son, New York.
(Continued)

*Primary Examiner* — Jeffrey P Aiello

(57) ABSTRACT

Systems and methods of associating a test compound with a reference compound are provided. A fingerprint of a chemical structure of the test compound is obtained. Abundance values for a set of cellular constituents are also obtained, from one or more reference assays, across a plurality of cells that have been exposed to a control solution free of the test compound. The fingerprint and the abundance values are inputted into a model that outputs a predicted similarity between (i) a predicted perturbational effect of the test compound across the set of cellular constituents and (ii) a measured cell-based perturbational effect of the reference compound across the set of cellular constituents. When the predicted similarity achieves a threshold similarity, the test compound is associated with the reference compound.

32 Claims, 30 Drawing Sheets

(58) Field of Classification Search
CPC ........ G16H 50/20; G16H 40/67; G16H 40/63; G06F 15/00
USPC .............. 435/6.11, 6.1, 69.1, 199; 514/44 A, 514/44 R; 702/22, 19, 30, 27, 23, 32, 702/189, 183, 188, 127; 703/11, 2, 12
See application file for complete search history.

(56) References Cited

OTHER PUBLICATIONS

Boser et al., 1992, "A training algorithm for optimal margin classifiers," in Proceedings of the 5th Annual ACM Workshop on Computational Learning Theory, ACM Press, Pittsburgh, Pa., pp. 142-152.
Bray et al., 2016, "Cell Painting, a high-content image-based assay for morphological profiling using multiplexed fluorescent dyes," Nature Protocols, 11, p. 1757-1774.
Fernandes et al., 2017, "Transfer Learning with Partial Observability Applied to Cervical Cancer Screening," Pattern Recognition and Image Analysis: 8th Iberian Conference Proceedings, 243-250.
Furey et al., 2000, Bioinformatics 16, 906-914.
Hastie, 2001, The Elements of Statistical Learning, Springer, New York (Chapter 9).
Krizhevsky et al., 2012, "Imagenet classification with deep convolutional neural networks," in *Advances in Neural Information Processing Systems 2*, Pereira, Burges, Bottou, Weinberger, eds., pp. 1097-1105, Curran Associates, Inc.
Larochelle et al., 2009, "Exploring strategies for training deep neural networks," J Mach Learn Res 10, pp. 1-40.
McLachlan et al., Bioinformatics 18(3):413-422, 2002.
Ng et al., 2002, "On discriminative vs. generative classifiers: A comparison of logistic regression and naive Bayes," Advances in Neural Information Processing Systems, 14.
O'Boyle N, Dalke A. DeepSMILES: An Adaptation of SMILES for Use in Machine-Learning of Chemical Structures. ChemRxiv. 2018; doi:10.26434/chemrxiv.7097960.v1.
Schliep et al., 2003, Bioinformatics 19(1):i255-i263.
Vapnik, 1998, Statistical Learning Theory, Wiley, New York; Mount, 2001, Bioinformatics: sequence and genome analysis, Cold Spring Harbor Laboratory Press, Cold Spring Harbor, N.Y.

* cited by examiner

Goal: Given a chemical structure, predict if it will have the same perturbational effect as a target perturbational effect.

 For a given similarity threshold determine if a respective vector of V-scores is a hit or a non-hit.

$$f\left(\left|\begin{array}{c}\rule{0pt}{6pt}\\ \rule{0pt}{6pt}\end{array}\right|\right) = \text{Hit/Non-hit (Classifier Score)}$$

304

310 (second model prediction of similarity between analog compound A cell behavior and reference compound target cell behavior)

f (V-score of analog compound A)

FIG. 4D

SBR Score: A score predicted based on chemical structure to indicate cell behavior similarity (e.g., transcriptional similarity) to the target cell behavior (e.g., target signature).

SYSTEMS AND METHODS FOR PREDICTING COMPOUNDS ASSOCIATED WITH TRANSCRIPTIONAL SIGNATURES

CROSS REFERENCE TO RELATED APPLICATIONS

This application claims priority to U.S. Provisional Patent Application Ser. No. 63/387,251, filed Dec. 13, 2022, which is hereby incorporated by reference in its entirety.

TECHNICAL FIELD

The present invention relates generally to systems and methods for predicting compounds associated with transcriptional signatures.

BACKGROUND

The study of cellular mechanisms is important for understanding disease.

Biological tissues are dynamic and highly networked multicellular systems. Dysfunction in subcellular networks in specific cells shift the entire landscape of cell behaviors and leads to disease states. Existing drug discovery efforts seek to characterize the molecular mechanisms that cause cells to transition from healthy to disease states, and to identify pharmacological approaches to reverse or inhibit these transitions. Past efforts have also sought to identify molecular signatures characterizing these transitions, and to identify pharmacological approaches that reverse these signatures.

Molecular data on cells, in tissues or cells enriched by surface markers, comprise phenotypic and molecular diversity for cells in a population that can be challenging to resolve. The heterogeneity of cells in these collections of cells often results in misleading or incorrect efforts aimed at elucidating disease-driving mechanisms. Approaches such as RNA sequencing, particularly single-cell RNA sequencing, can characterize cells at higher resolution, such as individual cells at the molecular level. These data provide a substrate for understanding varied cell states at higher resolution and reveal the rich and remarkable diversity of states that cells possess.

Significant challenges exist when interpreting sequencing data, for instance single cell data, namely the sparsity of these data, overlooking the presence of molecules present in cells, and noise, with uncertainty in the accuracy of these molecular measurements. Accordingly, new approaches are required to derive insight into pharmacological approaches for controlling individual cell state, and to correspondingly resolve disease.

In addition, complex diseases often cannot be broken down to a single or a few molecular targets. In spite of recent advances in high-throughput imaging technology and high-throughput screening for in vitro disease models, translating candidate targets generated from in vitro-based screening approaches into efficacious drugs is a considerable task that often involves a return to the comparatively slow and inefficient molecular target-based drug discovery approach.

Given the above background, what is needed in the art are systems and methods for identification of candidate compounds for drug discovery.

SUMMARY

The present disclosure addresses the above-identified shortcomings, at least in part, with systems and methods of associating test chemical compounds with reference compounds. In particular, the presently disclosed systems and methods utilize the chemical structure of a test chemical compound (e.g., a fingerprint of the chemical structure) to predict a similarity of a predicted perturbational effect of the test chemical compound across a set of cellular constituents (e.g., a predicted transcriptional signature for the test chemical compound) and a known perturbational effect of the reference compound across the set of cellular constituents (e.g., a measured, cell-based target transcriptional signature for the reference compound).

Advantageously, in some embodiments, the presently disclosed systems and methods facilitate the identification of chemical compounds that induce behavioral responses that are similar to a target behavioral response (e.g., a target perturbation, such as a transcriptional signature of a reference compound) using chemical structures, or representations thereof, without the need for additional cell-based assay data. In some implementations, this increases the speed and efficiency with which new compounds are identified for further validation and development, such as by allowing for high-throughput screens of chemical structure libraries for which cell-based assay data is not available. Moreover, this reduces the amount of labor and analysis required to obtain and compare cell-based behavioral data between a test chemical compound and a target reference compound. In some implementations, the systems and methods disclosed herein are used for determining one or more test chemical compounds for treating various physiological conditions, such as disease, based on predicted similarities (e.g., similar perturbational effects) to a reference compound that is known or currently used for treating the various physiological conditions.

In an example implementation, the systems and methods disclosed herein were used to predict if a chemical structure of a test chemical compound, or a representation thereof, drives a target transcriptional perturbation in cells, as illustrated in Example 1, below, with reference to FIGS. 6A-B, 7, and 8A-B. A first model was used to predict whether test chemical compounds were associated with a reference compound (e.g., transcriptionally similar to the reference compound), based on the chemical structure of the test chemical compounds and a transcriptional signature for a control solution free of the test chemical compounds (e.g., a control transcriptional signature). The first model's accuracy was measured by receiver operating characteristic area under curve (ROC AUC=0.91) and average precision (AP=0.87), showing strong predictability by the first model. Test chemical compounds that were predicted as transcriptionally similar to the reference compound ("predicted hits") were validated by comparing the transcriptional responses (e.g., differential expression of a panel of genes) induced in test cells by the predicted hits versus the reference compound. Notably, the transcriptional responses induced by the predicted hits and the reference compound were highly similar, whereas random control compounds (non-hits) induced transcriptional responses that were substantially different from that of the reference compound. These results demonstrate the ability of the first model to accurately predict whether a test chemical compound induces behavioral responses (e.g., transcriptional responses) that are similar to a target behavioral response induced by a reference compound.

One aspect of the present disclosure provides a method of associating a test chemical compound with a reference compound, including obtaining a fingerprint of a chemical structure of the test chemical compound. The method further includes obtaining, from one or more reference assay experiments, a plurality of abundance values for each cellular constituent in a set of cellular constituents across a first plurality of cells that have been exposed to a control solution free of the test chemical compound. Responsive to inputting the fingerprint of the chemical structure of the test chemical compound and the plurality of abundance values into a first model, a predicted similarity between (i) a predicted perturbational effect of the test chemical compound across the set of cellular constituents and (ii) a measured cell-based perturbational effect of the reference chemical compound across the set of cellular constituents is retrieved as output from the first model. When the predicted similarity achieves a threshold similarity, the test chemical compound is associated with the reference compound.

In some embodiments, the first model comprises a first plurality of parameters.

In some embodiments, the control solution is a polar aprotic solvent or a mixture of polar aprotic solvents. In some embodiments, the control solution is dimethyl sulfoxide, N,N-dimethylformamide, acetonitrile, acetone or a mixture thereof.

In some embodiments, each respective abundance value in the plurality of abundance values is a measure of central tendency of the abundance value of the corresponding cellular constituent across the first plurality of cells in the one or more reference assay experiments.

In some embodiments, the plurality of abundance values are obtained in the one or more reference assay experiments by single-cell ribonucleic acid (RNA) sequencing (scRNA-seq).

In some embodiments, each cellular constituent in the set of cellular constituents uniquely maps to a different gene. In some embodiments, each cellular constituent in the plurality of cellular constituents is a particular gene, a particular mRNA associated with a gene, a carbohydrate, a lipid, an epigenetic feature, a metabolite, an antibody, a peptide a protein, or a post-translational modification of a protein. In some embodiments, the set of cellular constituents comprises 10 or more cellular constituents, 20 or more cellular constituents, 30 or more cellular constituents, 40 or more cellular constituents, or 50 or more cellular constituents. In some embodiments, the set of cellular constituents consists of between 10 and 200 cellular constituents.

In some embodiments, the first model is a logistic regression model. In some embodiments, the first model is an algorithm for gradient boosting on decision trees. In some embodiments, the first model is CatBoost. In some embodiments, the first model comprises a logistic regression model, a boosted trees model, a random forest model, a decision tree model, a multinomial logistic regression model, a linear model, or a linear regression model.

In some embodiments, the first plurality of cells are cells from an organ, cells from a tissue, a plurality of stem cells, a plurality of primary human cells, cells from umbilical cord blood, cells from peripheral blood, bone marrow cells, cells from a solid tissue, or a plurality of differentiated cells.

In some embodiments, the fingerprint of the chemical structure of the test chemical compound is calculated from a simplified molecular-input line-entry system (SMILES) string representation of the test chemical compound. In some embodiments, the fingerprint of the chemical structure of the test chemical compound is generated from a chemical structure of the test chemical compound using Daylight, BCI, ECFP4, EcFC, MDL, APFP, TTFP, UNITY 2D fingerprint, RNNS2S, or GraphConv.

In some embodiments, the plurality of abundance values are determined by a colorimetric measurement, a fluorescence measurement, a luminescence measurement, a resonance energy transfer (FRET) measurement, a measurement of a protein-protein interaction, a measurement of a protein-polynucleotide interaction, a measurement of a protein-small molecule interaction. mass spectrometry, nuclear magnetic resonance, or a microarray measurement.

In some embodiments, the test chemical compound is a first organic compound having a molecular weight of less than 2000 Daltons, and the reference chemical compound is a second organic compound having a molecular weight of less than 2000 Daltons. In some embodiments, the test chemical compound satisfies any two or more rules, any three or more rules, or all four rules of the Lipinski's rule of Five: (i) not more than five hydrogen bond donors, (ii) not more than ten hydrogen bond acceptors, (iii) a molecular weight under 500 Daltons, and (iv) a Log P under 5.

In some embodiments, the reference compound alleviates a condition in a subject, and the method further includes administering the test chemical compound to the subject as a treatment to alleviate the condition in the subject when the predicted similarity achieves the threshold similarity. In some embodiments, the treatment includes a composition comprising the test chemical compound and one or more excipient and/or one or more pharmaceutically acceptable carrier and/or one or more diluent. In some embodiments, the condition is inflammation or pain. In some embodiments, the condition is a disease. In some embodiments, the condition is a cancer, hematologic disorder, autoimmune disease, inflammatory disease, immunological disorder, metabolic disorder, neurological disorder, genetic disorder, psychiatric disorder, gastroenterological disorder, renal disorder, cardiovascular disorder, dermatological disorder, respiratory disorder, viral infection, or other disease or disorder.

In some embodiments, the method further includes training the first model.

In some embodiments, the first model includes a plurality of weights and the training includes, for each respective training compound in a plurality of training compounds, performing a procedure comprising: (i) obtaining a respective training fingerprint of a chemical structure of the respective training compound; (ii) responsive to inputting the respective fingerprint of the chemical structure of the respective training compound and the plurality of abundance values for each cellular constituent in the set of cellular constituents across the first plurality of cells into the first model, retrieving, as respective training output from the first model, a corresponding training predicted similarity between (a) a predicted perturbational effect of the respective training compound across the set of cellular constituents and (b) a measured cell-based perturbational effect of the reference chemical compound across the set of cellular constituents; (iii) applying a respective difference to a loss function to obtain a respective output of the loss function, where the respective difference is between (a) the corresponding training predicted similarity from the first model and (b) a score from a second model that indicates whether, or to what degree, a predicted perturbational effect of the respective training compound across the set of cellular constituents matches a measured cell-based perturbational effect of the reference chemical compound across the set of cellular constituents; and (iv) using the respective output of the loss function to adjust the first plurality of parameters.

In some embodiments, the score from the second model is obtained by inputting a vector of abundance values into a second model, where each element in the vector of abundance values is a difference between: (a) an abundance of a corresponding cellular constituent in the set of cellular constituents in a corresponding reference cell-based assay upon exposure to the respective training compound solvated in the control solution; and (b) an abundance of a corresponding cellular constituent in the set of cellular constituents in a corresponding reference cell-based assay upon exposure to the control solution free of the respective training compound.

Another aspect of the present disclosure provides a computer system having one or more processors, and memory storing one or more programs for execution by the one or more processors, the one or more programs comprising instructions for performing any of the methods and/or embodiments disclosed herein.

Another aspect of the present disclosure provides a non-transitory computer readable storage medium storing one or more programs configured for execution by a computer, the one or more programs comprising instructions for carrying out any of the methods and/or embodiments disclosed herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The embodiments disclosed herein are illustrated by way of example, and not by way of limitation, in the figures of the accompanying drawings. Like reference numerals refer to corresponding parts throughout the drawings.

FIGS. 4A, 4B, 4C, 4D, and 4E collectively illustrate an example schematic for associating a test chemical compound with a reference compound, in accordance with some embodiments of the present disclosure.

FIG. 8A shows that hit compounds ("Predicted" 1, 2, 3, and 4) predicted as similar by the first model directly from chemical structure produce a similar gene expression profile in cells as the reference compound. FIG. 8B shows that randomly selected, non-hit control compounds ("Control" 1, 2, 3, and 4) produce different gene expression profiles than the reference compound's expression profile.

DETAILED DESCRIPTION

Introduction

Figure 1A:
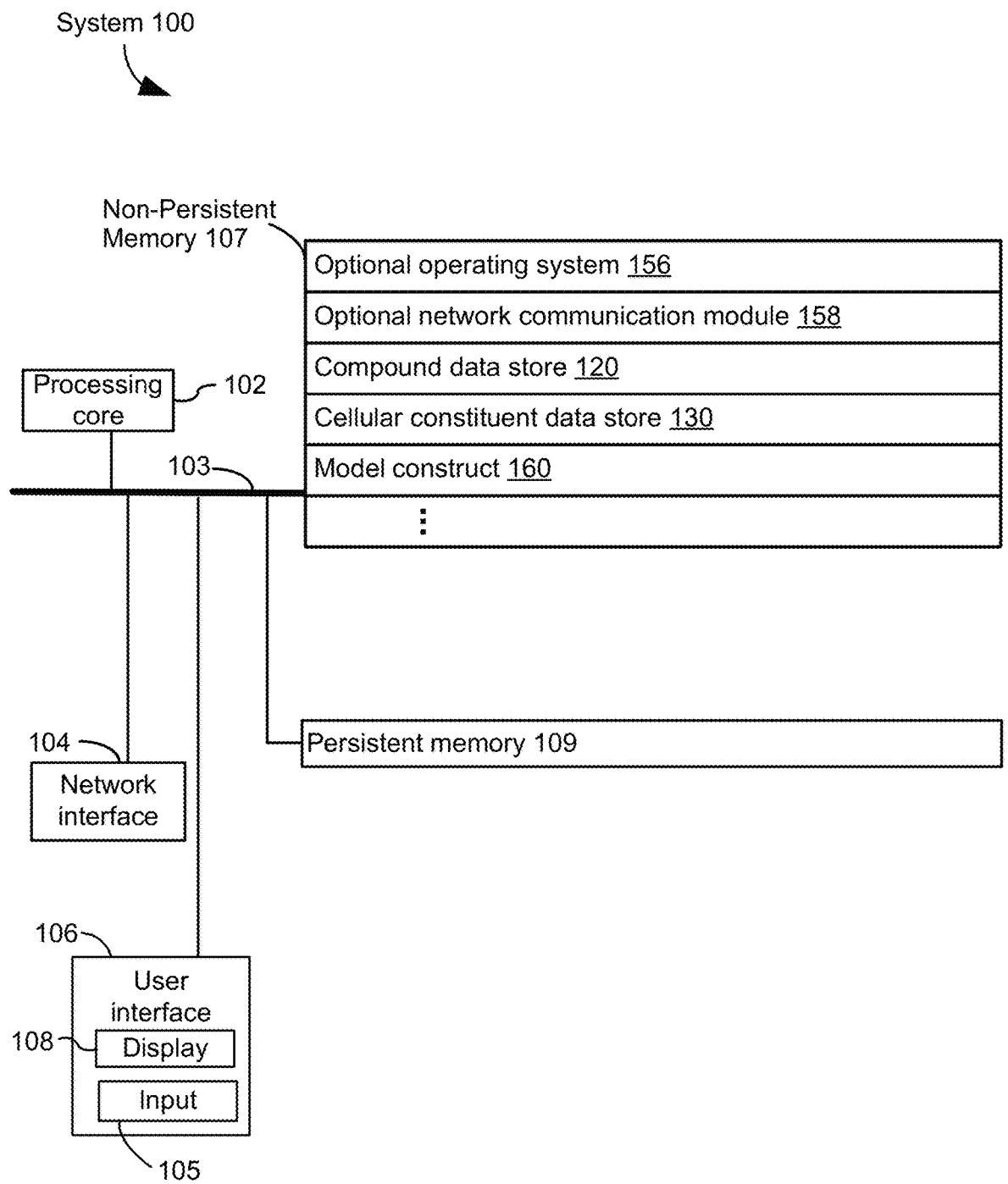
FIGS. 1A and 1B illustrates a block diagram of an exemplary system and computing device, in accordance with an embodiment of the present disclosure.

Molecular signatures in cells, such as transcriptional signatures, are useful for the characterization of diseases and other biological conditions. Moreover, the identification of such molecular signatures can inform drug discovery and development by providing a target for pharmacological approaches to reverse or inhibit these signatures and the cellular behaviors they implicate. Exposure to various chemical compounds often induces perturbational effects in cells, or changes in the molecular signatures of the cells. In some instances, it is desirable to identify new and/or unknown chemical compounds that have similar perturbational effects as existing compounds, for example, to obtain alternative chemical compounds that can be optimized for increased efficacy and/or reduced toxicity relative to a reference compound.

Conventional machine learning approaches related to drug discovery utilize in silico target screening capabilities using 3D protein and chemical structure representation paired with deep learning methods and high-performance computing to compute a candidate compound's method of action towards a library of targets. These approaches, however, fall under the target-focused screening paradigm, which does not adequately address the complexity of dynamic and highly networked multicellular systems underlying biological processes. Other conventional methods for drug discovery use machine learning approaches to model how single cells and cell lines respond to perturbations, based on transcriptomic data or imaging data. In such methods, high-throughput datasets are used to learn phenotypic representations of disease and compound perturbations of cellular in vitro systems. These are used to predict compounds that would induce or counteract phenotypic disease responses. Traditional high-throughput data modeling approaches, however, are disadvantaged by a lack of curation and a potential for the identification of large numbers of candidate targets. Validation of each potential candidate obtained from high-throughput screening is a laborious process, often requiring molecular target-based optimization or synthesis of hundreds or even thousands or compounds for in vitro screening.

Advantageously, the systems and methods disclosed herein address the shortcomings described above by providing a systematic, scalable approach for drug discovery. In contrast to the abovementioned approaches, the present disclosure describes an approach to drug discovery that targets the perturbational effects of a reference chemical compound across a set of cellular constituents in a target-agnostic manner. This approach is realized, in some aspects, by using a model to predict the similarity between (i) a predicted perturbational effect of a test compound across the set of cellular constituents and (ii) a measured, cell-based perturbational effect of the reference compound across the set of cellular constituents, responsive to inputting the chemical structure (or a representation thereof, e.g., a fingerprint) of the test compound and a molecular signature, for a first plurality of cells, responsive to a control solution that is free of the test compound. Test compounds are associated with the reference compound (e.g., deemed to induce similar perturbational effects) when the predicted similarity satisfies a threshold, and these associations can be used to predict new and/or unknown chemical structures for drug discovery. This target-agnostic approach advantageously allows for the systematic curation and optimization of candidate targets by associating them with known reference compounds, thus bridging the considerable gap between target discovery to predictive translation across systems. Many models require the development of in vivo assays (e.g. phenotypic assays) and screening of results to validate the model. For example, the process of measuring perturbational effects using cell-based assays for each test compound in a library of test compounds is laborious, costly, resource-heavy, and time-consuming. Herein, we disclose a model that considerably reduces the time, labor, personnel, and/or resources needed to generate input data.

For example, as illustrated in Example 1 below, fingerprints of the chemical structures of a set of test chemical compounds were inputted into a first model, along with the transcriptional signatures of cells exposed to control solutions free of the test chemical compounds. For each respective test chemical compound in the set of test chemical compounds, the first model outputted a predicted similarity between (i) a predicted transcriptional signature induced by the test chemical compound and (ii) a measured transcriptional signature induced by the reference chemical compound. For each respective test chemical compound in the set of test chemical compounds, the predicted similarity obtained from the first model was compared with a similarity score obtained from a second model, where the similarity score indicated whether, or to what degree, a predicted transcriptional signature for the respective test chemical compound matched a measured transcriptional signature for the reference chemical compound. The comparison was used to evaluate the accuracy of the first model's predictions.

Figure 6A:
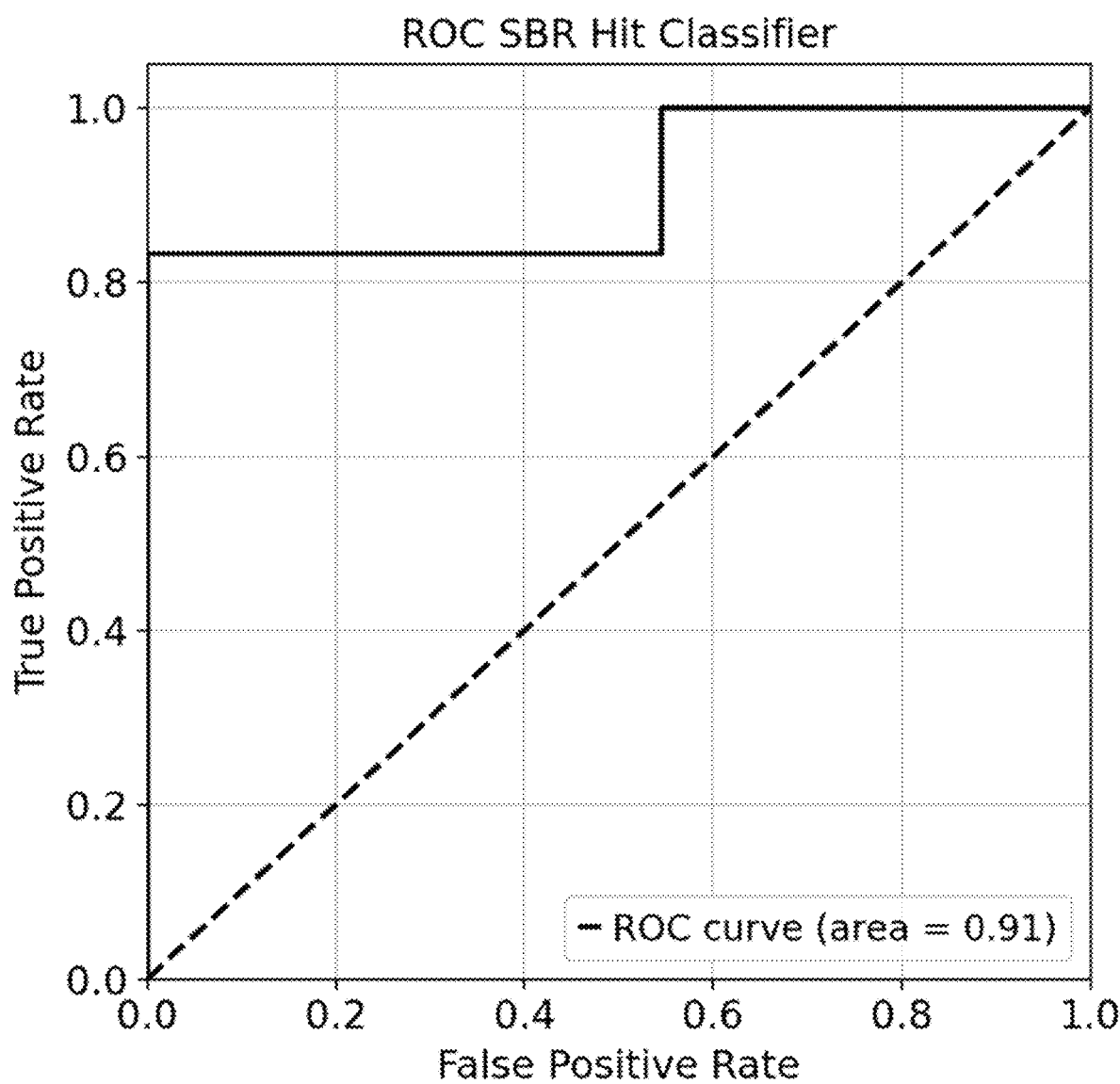
FIGS. 6A and 6B collectively illustrate receiver operating characteristic (ROC) area under the curve (AUC) and precision-recall metrics of a first model for associating a test chemical compound with a reference compound, where the first model predicts transcriptional similarity using, as input, chemical structures for a set of unseen test chemical compounds classified as being similar ("transcriptional hit") or not similar ("not a hit") to a target transcriptional profile for a reference compound, in accordance with an embodiment of the present disclosure.
Figure 6B:
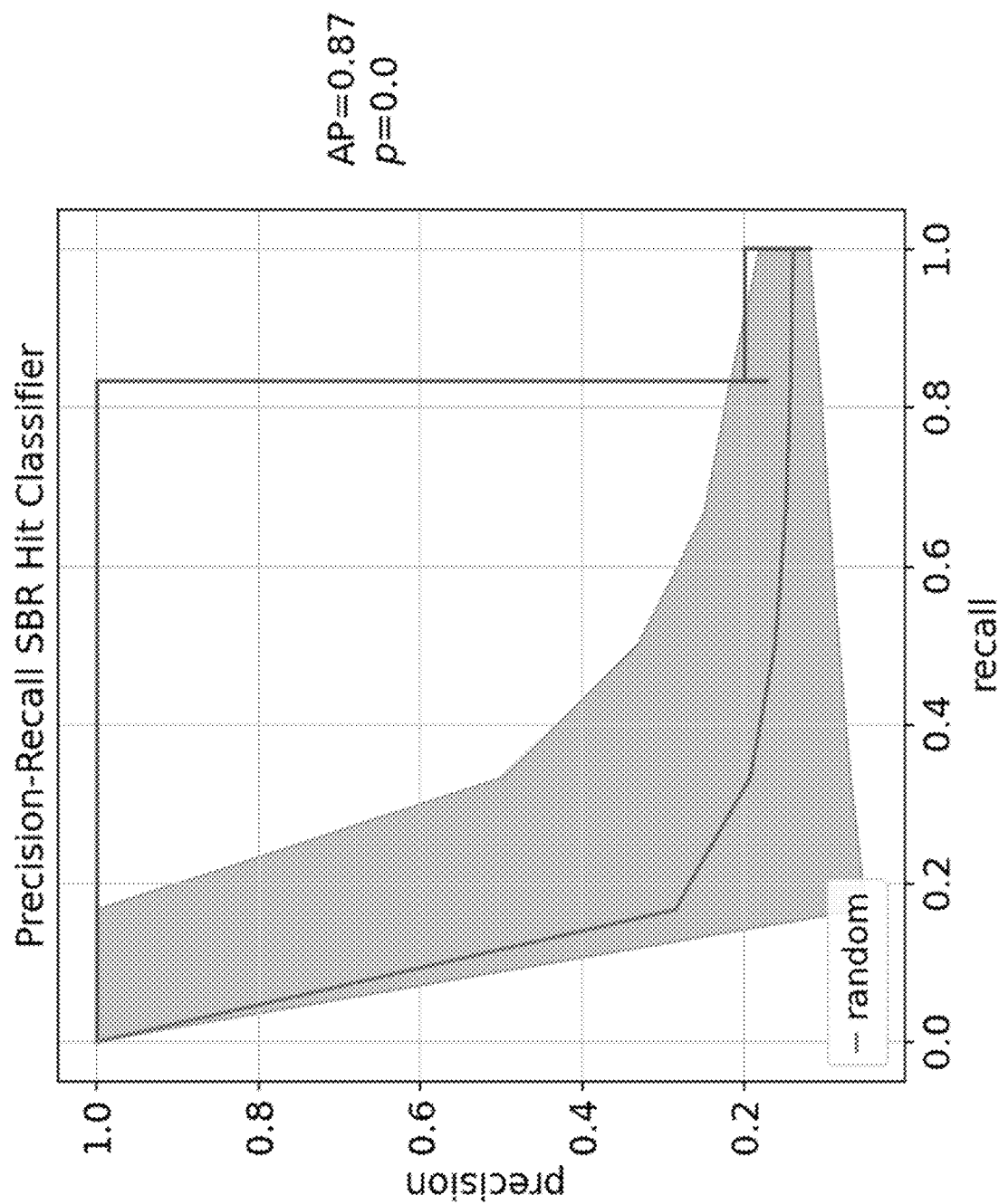
Figure 7:
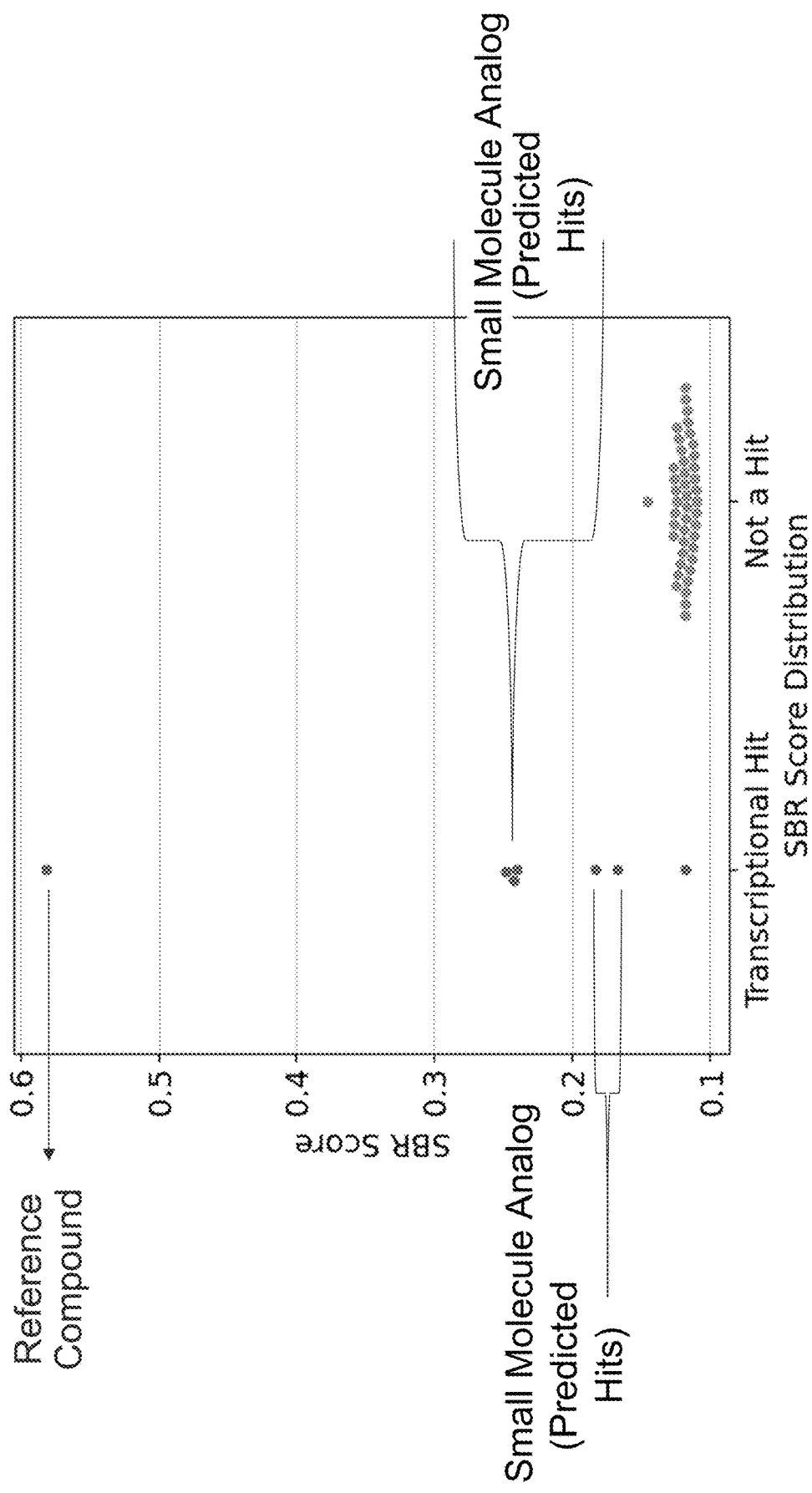
FIG. 7 illustrates predicted similarities obtained from a first model for associating a test chemical compound with a reference compound, where the first model uses, as input, chemical structures for a set of unseen test chemical compounds classified as being similar ("transcriptional hit") or not similar ("not a hit") to a target transcriptional profile for a reference compound, in accordance with an embodiment of the present disclosure.
Figure 8A:
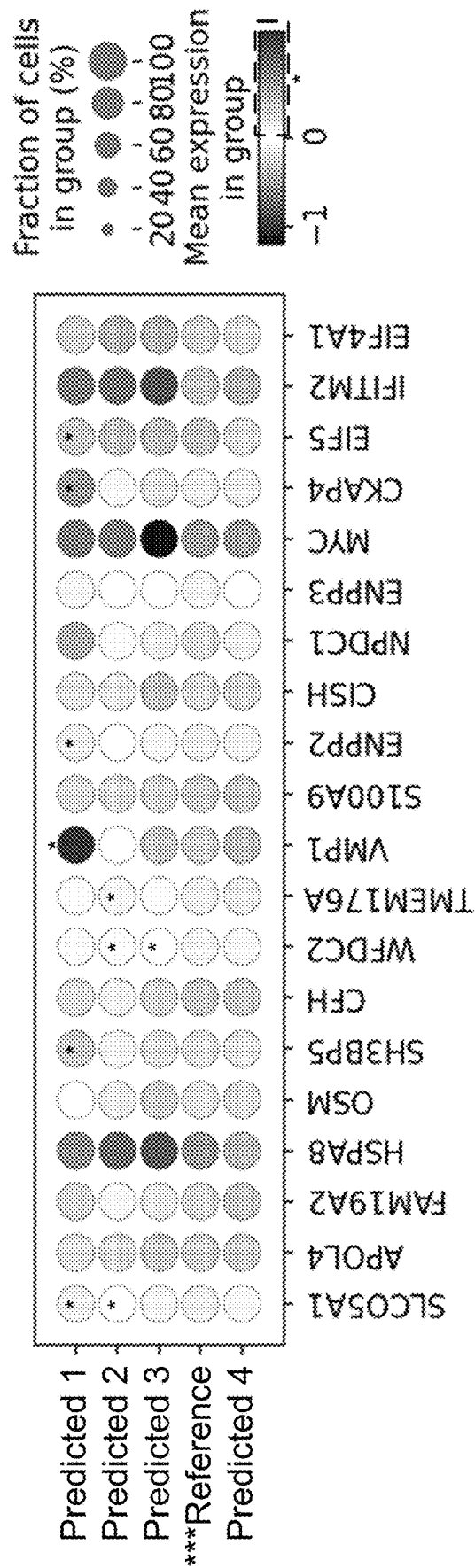
FIGS. 8A and 8B collectively illustrate gene expression of perturbations predicted by a first model for associating a test chemical compound with a reference compound, in accordance with an embodiment of the present disclosure.
Figure 8B:
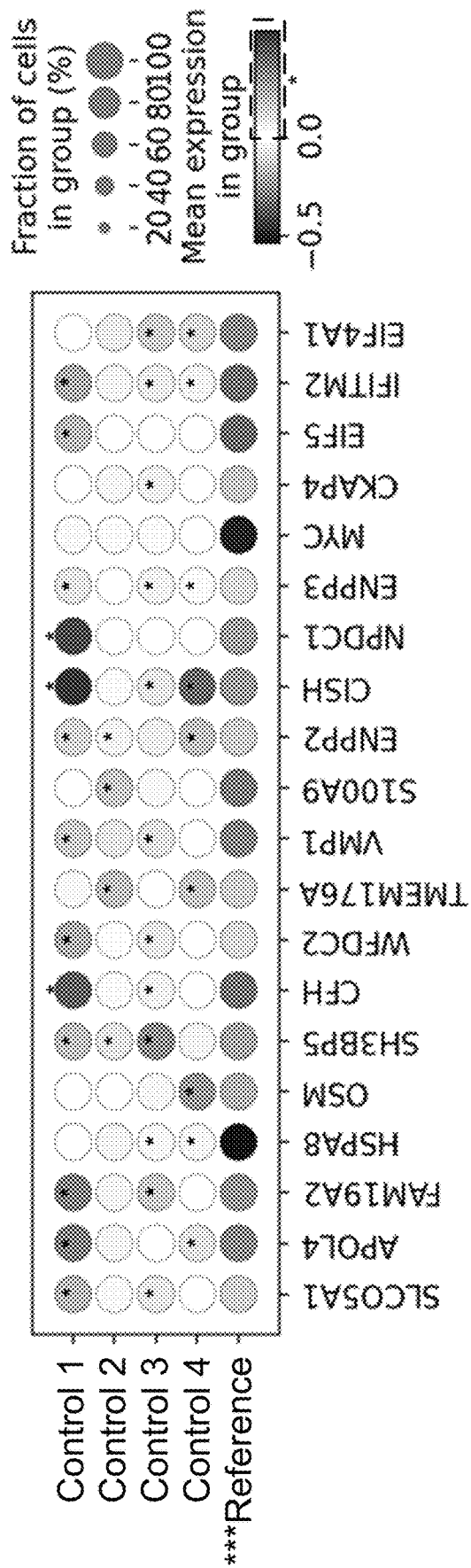

Notably, as illustrated in FIGS. 6A-B, the first model exhibited strong predictability, as measured by receiver operating characteristic area under curve (ROC AUC=0.91) and average precision metrics (AP=0.87). As further illustrated in FIGS. 7 and 8A-B, test chemical compounds that were predicted as transcriptionally similar to the reference compound ("predicted hits") were validated by comparing the transcriptional response (e.g., differential expression of a panel of genes) induced in test cells by the predicted hits versus the reference compound. The transcriptional responses induced by the predicted hits and the reference compound were highly similar, whereas random control compounds (non-hits) induced transcriptional responses that were substantially different from that of the reference compound. These results demonstrate the ability of the first model to accurately predict whether a test chemical compound induces behavioral responses (e.g., transcriptional responses) that are similar to a target behavioral response induced by a reference compound.

Example Benefits

The presently disclosed systems and methods are advantageously integrated into a practical application by providing value to the technical field of drug discovery and development. For example, system and methods disclosed herein facilitate the in-silico prediction of transcriptional effects directly from chemical structure; the use of large-scale screenings to identify new test compounds with perturbational similarity to a target perturbational signature (e.g., a transcriptional profile induced by a reference compound); and the optimization of structures towards target cell behaviors (e.g., perturbational effects) without a cellular target by using target-agnostic in-silico screening. In some implementations, these characteristics allow for faster and more efficient optimization of test chemical compounds towards target cell behaviors.

For instance, in some implementations, systems and methods disclosed herein utilize a first model to optimize test chemical compounds towards a target cell behavior using chemical structures. This characteristic allows for the prediction of perturbational similarity even in the absence of measured, cell-based perturbational data that is specific to the test chemical compound. In other words, systems and methods disclosed herein can be performed without the need to obtain measured abundance values for each cellular constituent in a set of cellular constituents across a plurality of cells that have been exposed to a test chemical compound. Traditional methods for determining similarity of perturbational effects (e.g., transcriptional signatures) between a test chemical compound and a reference compound include measuring abundance values for cellular constituents (e.g., genes) in cells exposed to the test chemical compound, normalizing these abundance values against measurements obtained from a control solution (e.g., the control solution in which the test chemical compound is solvated), and comparing the normalized abundance values for the test chemical compound against normalized abundance values similarity obtained for the reference compound.

The process of comparing perturbational effects between reference and test compounds and identifying test compounds that have similar perturbational effects is considerably more laborious and resource-heavy than methods disclosed herein. In particular, obtaining test compound-specific perturbational effects often relies on the execution of cell-based assays to manually generate measured abundance values for each respective cellular constituent in a set of cellular constituents, for each test compound. In cases where there are many test chemical compounds to be screened, such as in a high throughput screen over a large library of candidate compounds (e.g., hundreds, thousands, or tens of thousands of candidate compounds), the effort of obtaining measured abundance values becomes prohibitively difficult.

Advantageously, systems and methods disclosed herein, in some aspects, rely only on the chemical structure of the test chemical compound (or a representation thereof, e.g., a fingerprint) and a plurality of abundance values for each cellular constituent in a set of cellular constituents across a first plurality of cells that have been exposed to a control solution free of the test chemical compound (e.g., a perturbational signature for a control solution or "blank"). Because the abundance values for the control solution are not specific to the test chemical compound, this significantly reduces the burden of having to perform cell-based assays for each respective test chemical compound for which a similarity prediction is desired (e.g., when screening a large library of candidate compounds). For example, abundance values for a control solution can be obtained in one or more reference assay experiments, and these abundance values can be reused as input to the first model for each respective test chemical compound in a plurality of test chemical compounds. The broad applicability of, in some such instances, a single set of abundance values with each of a plurality of test chemical compounds as input to the first model considerably reduces the time, labor, personnel, and resources needed to generate such input data. Moreover, in instances where a large number of test chemical compounds are screened, the corresponding number of unique datasets corresponding to the plurality of test chemical compounds can exact a heavy toll on the computational resources available to the first model. In contrast, the application of a broadly applicable set of abundance values for the control solution as input to the first model substantially reduces the computational burden and processing time needed for analysis and prediction.

Alternatively or additionally, in some implementations, systems and methods disclosed herein facilitate the use of large-scale screenings to identify new test compounds with perturbational similarity to a target perturbational signature (e.g., a transcriptional profile induced by a reference compound). Advantageously, this allows for the optimization of test chemical structures for efficacy that is driven by a transcriptional signature, as well as the mitigation of toxicity that is associated with a transcriptional signature.

Consider the case where a reference compound induces a target transcriptional signature in a corresponding plurality of cells (e.g., a transcriptional signature that reverses or ameliorates a disease-related cell behavior). In some such cases, it is desirable to identify new test chemical compounds that achieve similar transcriptional effects in cells as the reference compound. In some implementations, the new test chemical compounds include one or more test chemical compounds that have different toxicities, side effects, solubilities, or other biochemical or pharmacological properties. Such properties can be used to optimize chemical structures for drug discovery and development, for the modulation of various transcriptional perturbations and/or cell behaviors, including disease-associated cell behaviors. In addition to predicting a similarity between the perturbational effects induced by a test chemical compound and a reference compound, in some implementations, systems and methods disclosed herein can be used to identify chemical moieties that will induce a target perturbational effect.

In some implementations, systems and methods disclosed herein facilitate the optimization of structures towards target cell behaviors (e.g., perturbational effects) without a cellular target by using target-agnostic in-silico screening. In other words, in some implementations, systems and methods disclosed herein are used to predict new test chemical compounds having target activity (e.g., inducing target perturbational effects) based on the chemical structures and target-agnostic perturbation data. Particularly, the perturbation data that is inputted into the first model includes perturbations effects induced by a control solution, but is agnostic as to the perturbational effects of the test chemical compound on the target cell. Moreover, in some implementations, the input to the first model does not include a nucleotide or amino acid sequence of the test chemical compound, but relies on chemical structure for test compound-specific indications.

The application of perturbational effects induced by control solution in the first plurality of cells provides additional context to the inputs and outputs of the first model. For instance, in some implementations, the measured cell-based perturbational effect of the reference chemical compound across the set of cellular constituents is measured under assay conditions in which the reference compound is solvated in the control solution (e.g., DMSO). Thus, the plurality of abundance values for each cellular constituent in a set of cellular constituents across a first plurality of cells that have been exposed to a control solution free of the test chemical compound that is inputted into the first model allows the first model to account for (e.g., normalize against) one or more of a cell type, solvent, and/or experimental variability associated with the reference compound for which the perturbational effect is determined. Thus, the first model advantageously provides robust and accurate similarity predictions based on chemical structure, while reducing uncertainty due to technical variation and experimental background.

As described above, in some embodiments, a computational modeling architecture with predictive capabilities is used to determine associations between test chemical compounds and reference compounds, through the generation of similarity predictions between test compound-specific and reference compound-specific perturbational effects.

Advantageously, the present disclosure further provides various systems and methods that improve the association of test chemical compounds with reference compounds, by improving the training and use of a model for predictions of similarity between test compound-specific and reference compound-specific perturbational effects. The complexity of a machine learning model includes time complexity (running time, or the measure of the speed of an algorithm for a given input size n), space complexity (space requirements, or the amount of computing power or memory needed to execute an algorithm for a given input size n), or both. Complexity (and subsequent computational burden) applies to both training of and prediction by a given model.

In some instances, computational complexity is impacted by implementation, incorporation of additional algorithms or cross-validation methods, and/or one or more parameters (e.g., weights and/or hyperparameters). In some instances, computational complexity is expressed as a function of input size n, where input data is the number of instances (e.g., the number of training samples), dimensions p (e.g., the number of features), the number of trees $n_{trees}$ (e.g., for methods based on trees), the number of support vectors $n_{sv}$ (e.g., for methods based on support vectors), the number of neighbors k (e.g., for k nearest neighbor models), the number of classes c, and/or the number of neurons n, at a layer i (e.g., for neural networks). With respect to input size n, then, an approximation of computational complexity (e.g., in Big O notation) denotes how running time and/or space requirements increase as input size increases. Functions can increase in complexity at slower or faster rates relative to an increase in input size. Various approximations of computational complexity include but are not limited to constant (e.g., $O(1)$), logarithmic (e.g., $O(\log n)$), linear (e.g., $O(n)$), loglinear (e.g., $O(n \log n)$), quadratic (e.g., $O(n^2)$), polynomial (e.g., $O(n^c)$), exponential (e.g., $O(c^n)$), and/or factorial (e.g., $O(n!)$). In some instances, simpler functions are accompanied by lower levels of computational complexity as input sizes increase, as in the case of constant functions, whereas more complex functions such as factorial functions can exhibit substantial increases in complexity in response to slight increases in input size.

Computational complexity of machine learning models can similarly be represented by functions (e.g., in Big O notation), and complexity varies in some instances depending on the type of model, the size of one or more inputs or dimensions, usage (e.g., training and/or prediction), and/or whether time or space complexity is being assessed. For example, complexity in decision tree models is approximated as $O(n^2 p)$ for training and $O(p)$ for predictions, while complexity in linear regression models is approximated as $O(p^2 n + p^3)$ for training and $O(p)$ for predictions. For random forest models, training complexity is approximated as $O(n^2 p n_{trees})$ and prediction complexity is approximated as $O(p n_{trees})$. For gradient boosting models, complexity is approximated as $O(npn_{trees})$ for training and $O(pn_{trees})$ for predictions. For kernel support vector machines, complexity is approximated as $O(n^2 p + n^3)$ for training and $O(n_{sv} p)$ for predictions. For naïve Bayes models, complexity is represented as $O(np)$ for training and $O(p)$ for predictions, and for neural networks, complexity is approximated as $O(pn_1 + n_1 n_2 + \ldots)$ for predictions. Complexity in K nearest neighbors models is approximated as $O(knp)$ for time and $O(np)$ for space. For logistic regression models, complexity is approximated as $O(np)$ for time and $O(p)$ for space. For logistic regression models, complexity is approximated as $O(np)$ for time and $O(p)$ for space.

As described above, for machine learning models, computational complexity determines the scalability and therefore the overall effectiveness and usability of a model (e.g., a regressor) for increasing input, feature, and/or class sizes, as well as for variations in model architecture. In the context of large-scale datasets, as in the case of gene expression datasets comprising abundances of at least 10, at least 100, at least 1000 or more genes obtained for at least 10, at least 100, at least 1000 or more cells and/or test chemical compounds, the computational complexity of functions performed on such large datasets can strain the capabilities of many existing systems. In addition, as the number of input features (e.g., number of cellular constituents (e.g., genes) and/or number of abundance values per cellular constituent) and/or the number of instances (e.g., number of test chemical compounds) increases together with technological advancements, increasing availability of annotations, and expanding downstream applications and possibilities, the computational complexity of any given classification model can quickly overwhelm the time and space capacities provided by the specifications of a respective system.

Thus, by using a machine learning model with a minimum input size (e.g., at least 10, at least 100, at least 1000 or more test chemical compounds or training compounds; at least 10, at least 50, at least 100 or more cellular constituents; and/or at least 5, at least 10, at least 100 or more abundance values per cellular constituent) and/or a corresponding minimum number of parameters (e.g., at least 50, at least 100, or at least 1000 parameters) for the association of test chemical compounds with reference compounds, the computational complexity is proportionally increased such that it cannot be mentally performed, and the method addresses a computational problem.

Additional details on computational complexity in machine learning models are provided in "Computational complexity of machine learning algorithms," published Apr. 16, 2018, available online at: thekemeltrip.com/machine/learning/computational-complexity-learning-algorithms; Hastie, 2001, *The Elements of Statistical Learning*, Springer, New York; and Arora and Barak, 2009, *Computational Complexity: A Modern Approach*, Cambridge University Press, New York; each of which is hereby incorporated herein by reference in its entirety.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure, in some embodiments, is practiced without these specific details. In other instances, well-known methods, procedures, components, circuits, and networks have not been described in detail so as not to unnecessarily obscure aspects of the embodiments.

In some embodiments, plural instances are provided for components, operations or structures described herein as a single instance. Finally, boundaries between various components, operations, and data stores are somewhat arbitrary, and particular operations are illustrated in the context of specific illustrative configurations. Other forms of functionality are envisioned and, in some embodiments, fall within the scope of the implementation(s). In general, structures and functionality presented as separate components in the example configurations, in some embodiments, are implemented as a combined structure or component. Similarly, structures and functionality presented as a single component, in some embodiments, are implemented as separate components. These and other variations, modifications, additions, and improvements fall within the scope of the implementation(s).

It will also be understood that, although the terms "first," "second," etc., in some embodiments, are used herein to describe various elements, these elements should not be limited by these terms. These terms are only used to distinguish one element from another. For example, a first dataset could be termed a second dataset, and, similarly, a second dataset could be termed a first dataset, without departing from the scope of the present invention. The first dataset and the second dataset are both datasets, but they are not the same dataset.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" will be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" will be construed to mean "upon determining" or "in response to determining" or "in accordance with a determination" or "upon detecting" or "in response to detecting" that the stated condition precedent is true, depending on the context.

Furthermore, when a reference number is given an "$i^{th}$" denotation, the reference number refers to a generic component, set, or embodiment. For instance, a cellular-component termed "cellular-component i" refers to the $i^{th}$ cellular-component in a plurality of cellular-components.

The foregoing description included example systems, methods, techniques, instruction sequences, and computing machine program products that embody illustrative implementations. For purposes of explanation, numerous specific details are set forth in order to provide an understanding of various implementations of the inventive subject matter. It will be evident, however, to those skilled in the art that implementations of the inventive subject matter, in some embodiments, is practiced without these specific details. In general, well-known instruction instances, protocols, structures and techniques have not been shown in detail.

The foregoing description, for purpose of explanation, has been described with reference to specific implementations. However, the illustrative discussions below are not intended to be exhaustive or to limit the implementations to the precise forms disclosed. Many modifications and variations are possible in view of the above teachings. The implementations are chosen and described in order to best explain the principles and their practical applications, to thereby enable others skilled in the art to best utilize the implementations and various implementations with various modifications as are suited to the particular use contemplated.

In the interest of clarity, not all of the routine features of the implementations described herein are shown and described. It will be appreciated that, in the development of any such actual implementation, numerous implementation-specific decisions are made in order to achieve the designer's specific goals, such as compliance with use case- and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like.

The language used in the specification has been principally selected for readability and instructional purposes, and in some instances has not been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention.

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

Any terms not directly defined herein shall be understood to have the meanings commonly associated with them as understood within the art of the invention. Certain terms are discussed herein to provide additional guidance to the practitioner in describing the compositions, devices, methods, and the like of aspects of the invention, and how to make or use them. It will be appreciated that the same thing, in some embodiments, is said in more than one way. Consequently, in some instances, alternative language and synonyms apply to any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents unless it is explicitly stated. Use of examples, including examples of terms, is for illustrative purposes only and does not limit the scope and meaning of the aspects of the invention herein.

Definitions

As used herein, the term "about" or "approximately" means within an acceptable error range for the particular value as determined by one of ordinary skill in the art, which depends in part on how the value is measured or determined, e.g., the limitations of the measurement system. For example, in some embodiments "about" means within 1 or more than 1 standard deviation, per the practice in the art. In some embodiments, "about" means a range of 20%, ±10%, ±5%, or ±1% of a given value. In some embodiments, the term "about" or "approximately" means within an order of magnitude, within 5-fold, or within 2-fold, of a value. In some implementations, where particular values are described in the application and claims, unless otherwise stated the term "about" means an acceptable error range for the particular value is assumed. All numerical values within the detailed description herein are modified by "about" the indicated value, and consider experimental error and variations that would be expected by a person having ordinary skill in the art. In some embodiments, the term "about" has the meaning as commonly understood by one of ordinary skill in the art. In some embodiments, the term "about" refers to ±10%. In some embodiments, the term "about" refers to ±5%.

As used herein, the terms "abundance," "abundance level," or "expression level" refers to an amount of a cellular constituent (e.g., a gene product such as an RNA species, e.g., mRNA or miRNA, or a protein molecule) present in one or more cells, or an average amount of a cellular constituent present across multiple cells. When referring to mRNA or protein expression, the term generally refers to the amount of any RNA or protein species corresponding to a particular genomic locus, e.g., a particular gene. However, in some embodiments, an abundance refers to the amount of a particular isoform of an mRNA or protein corresponding to a particular gene that gives rise to multiple mRNA or protein isoforms. In some embodiments, the genomic locus is identified using a gene name, a chromosomal location, or any other genetic mapping metric.

As used interchangeably herein, a "cell state" or "biological state" refers to a state or phenotype of a cell or a population of cells. For example, in some embodiments, a cell state is healthy or diseased. In some embodiments, a cell state is one of a plurality of diseases. In some embodiments, a cell state is a response to a compound treatment and/or a differentiated cell lineage. In some embodiments, a cell state is characterized by a measure (e.g., an activation, expression, and/or measure of abundance) of one or more cellular constituents, including but not limited to one or more genes, one or more proteins, and/or one or more biological pathways.

As used herein, a "cell state transition" or "cellular transition" refers to a transition in a cell's state from a first cell state to a second cell state. In some embodiments, the second cell state is an altered cell state (e.g., a healthy cell state to a diseased cell state). In some embodiments, one of the respective first cell state and second cell state is an unperturbed state and the other of the respective first cell state and second cell state is a perturbed state caused by an exposure of the cell to a condition. The perturbed state, in some embodiments, is caused by exposure of the cell to a compound. A cell state transition, in some embodiments, is marked by a change in cellular constituent abundance in the cell, and thus by the identity and quantity of cellular constituents (e.g., mRNA, transcription factors) produced by the cell (e.g., a perturbation signature).

As used herein, the term "dataset" in reference to cellular constituent abundance measurements for a cell or a plurality of cells, in some embodiments, refers to a high-dimensional set of data collected from one or more cells (e.g., a single-cell cellular constituent abundance dataset) in some contexts. In other contexts, the term "dataset," in some embodiments, refers to a plurality of high-dimensional sets of data collected from one or more cells (e.g., a plurality of single-cell cellular constituent abundance datasets), each set of data of the plurality collected from one cell of a plurality of cells.

As used herein, the term "differential abundance" or "differential expression" refers to differences in the quantity and/or the frequency of a cellular constituent present in a first entity (e.g., a first cell, plurality of cells, and/or sample) as compared to a second entity (e.g., a second cell, plurality of cells, and/or sample). In some embodiments, a first entity is a sample characterized by a first cell state (e.g., a diseased phenotype) and a second entity is a sample characterized by a second cell state (e.g., a normal or healthy phenotype). For example, a cellular constituent, in some embodiments, is a polynucleotide (e.g., an mRNA transcript) which is present at an elevated level or at a decreased level in entities characterized by a first cell state compared to entities characterized by a second cell state. In some embodiments, a cellular constituent, is a polynucleotide which is detected at a higher frequency or at a lower frequency in entities characterized by a first cell state compared to entities characterized by a second cell state. A cellular constituent, in some embodiments, is differentially abundant in terms of quantity, frequency or both. In some instances, a cellular constituent is differentially abundant between two entities if the amount of the cellular constituent in one entity is statistically significantly different from the amount of the cellular constituent in the other entity. For example, a cellular constituent is differentially abundant in two entities if it is present at least about 120%, at least about 130%, at least about 150%, at least about 180%, at least about 200%, at least about 300%, at least about 500%, at least about 700%, at least about 900%, or at least about 1000% greater in one entity than it is present in the other entity, or if it is detectable in one entity and not detectable in the other. In some instances, a cellular constituent is differentially expressed in two sets of entities if the frequency of detecting the cellular constituent in a first subset of entities (e.g., cells representing a first subset of annotated cell states) is statistically significantly higher or lower than in a second subset of entities (e.g., cells representing a second subset of annotated cell states). For example, a cellular constituent is differentially expressed in two sets of entities if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of entities than the other set of entities.

As used herein, the term "healthy" refers to a sample characterized by a healthy state (e.g., obtained from a subject possessing good health). A healthy subject, in some embodiments, demonstrates an absence of any malignant or non-malignant disease. A "healthy" individual, in some embodiments, has other diseases or conditions, unrelated to the condition being assayed, which are normally not considered "healthy."

As used herein, the term "perturbation" in reference to a cell (e.g., a perturbation of a cell or a cellular perturbation) refers to any exposure of the cell to one or more conditions, such as a treatment by one or more compounds. These compounds, in some embodiments, are referred to as "perturbagens." In some embodiments, the perturbagen includes, e.g., a small molecule, a biologic, a therapeutic, a protein, a protein combined with a small molecule, an ADC, a nucleic acid, such as an siRNA or interfering RNA, a cDNA over-expressing wild-type and/or mutant shRNA, a cDNA over-expressing wild-type and/or mutant guide RNA (e.g., Cas9 system or other gene editing system), or any combination of any of the foregoing. In some embodiments, a perturbation induces or is characterized by a change in the phenotype of the cell and/or a change in the expression or abundance level of one or more cellular constituents in the cell (e.g., a perturbation signature). For instance, a perturbation, in some embodiments, is characterized by a change in the transcriptional profile of the cell.

As used herein, the term "sample," "biological sample," or "patient sample," refers to any sample taken from a subject, which, in some embodiments, reflects a biological state associated with the subject. Examples of samples include, but are not limited to, blood, whole blood, plasma, serum, urine, cerebrospinal fluid, fecal, saliva, sweat, tears, pleural fluid, pericardial fluid, or peritoneal fluid of the subject. In some embodiments, a sample includes any tissue or material derived from a living or dead subject. In some embodiments, a sample is cell-free sample. In some embodiments, a sample comprises one or more cellular constituents. For instance, in some embodiments, a sample comprises a nucleic acid (e.g., DNA or RNA) or a fragment thereof, or a protein. In some embodiments, the term "nucleic acid" refers to deoxyribonucleic acid (DNA), ribonucleic acid (RNA) or any hybrid or fragment thereof. In some embodiments, the nucleic acid in the sample is a cell-free nucleic acid. In some embodiments, a sample is a liquid sample or a solid sample (e.g., a cell or tissue sample). In some embodiments, a sample is a bodily fluid. In some embodiments, a sample is a stool sample. In some embodiments, a sample is treated to physically disrupt tissue or cell structure (e.g., centrifugation and/or cell lysis), thus releasing intracellular components into a solution which further contains enzymes, buffers, salts, detergents, and the like which to prepare the sample for analysis.

As used herein, an "effective amount" or "therapeutically effective amount" is an amount sufficient to affect a beneficial or desired clinical result upon treatment. An effective amount, in some embodiments, is administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the therapeutic agent being administered.

As used herein, the term "classification" refers to any number(s) or other characters(s) that are associated with a particular property of a sample or input (e.g., one or more chemical structures, one or more abundance values, or a portion or representation thereof). For example, in some embodiments, the term "classification" refers to an association of a test chemical compound with a reference compound, such as a prediction of similarity between a predicted perturbational effect of the test chemical compound and a measured perturbational effect of the reference compound. In some embodiments, the term "classification" refers to a score that indicates a match between a perturbational effect of a training compound and a perturbational effect of a reference compound. For instance, in some implementations, a test chemical compound is determined to be similar or not similar to a reference compound when a predicted similarity achieves a threshold similarity. In some embodiments, the classification is binary (e.g., similar or not similar) or have more levels of classification (e.g., a scale from 1 to 10, from 1 to 100, or from 0 to 1). In some embodiments, the terms "cutoff" and "threshold" refer to predetermined numbers used in an operation. In some embodiments, a threshold value is a value above or below which a particular classification applies. For example, in some embodiments, a threshold similarity refers to a value above (or below) which a test chemical compound is associated with a reference compound. Either of these terms are applicable in either of these contexts.

As used interchangeably herein, the term "classifier" or "model" refers to a machine learning model or algorithm.

In some embodiments, a model includes an unsupervised learning algorithm. One example of an unsupervised learning algorithm is cluster analysis. In some embodiments, a model includes supervised machine learning. Nonlimiting examples of supervised learning algorithms include, but are not limited to, logistic regression, neural networks, support vector machines, Naïve Bayes algorithms, nearest neighbor algorithms, random forest algorithms, decision tree algorithms, boosted trees algorithms, multinomial logistic regression algorithms, linear models, linear regression, Gradient Boosting, mixture models, hidden Markov models, Gaussian NB algorithms, linear discriminant analysis, or any combinations thereof. In some embodiments, a model is a multinomial classifier algorithm. In some embodiments, a model is a 2-stage stochastic gradient descent (SGD) model. In some embodiments, a model is a deep neural network (e.g., a deep-and-wide sample-level model).

Neural networks. In some embodiments, the model is a neural network (e.g., a convolutional neural network and/or a residual neural network). Neural network algorithms, also known as artificial neural networks (ANNs), include convolutional and/or residual neural network algorithms (deep learning algorithms). In some embodiments, neural networks are machine learning algorithms that are trained to map an input dataset to an output dataset, where the neural network includes an interconnected group of nodes organized into multiple layers of nodes. For example, in some embodiments, the neural network architecture includes at least an input layer, one or more hidden layers, and an output layer. In some embodiments, the neural network includes any total number of layers, and any number of hidden layers, where the hidden layers function as trainable feature extractors that allow mapping of a set of input data to an output value or set of output values. In some embodiments, a deep learning algorithm or deep neural network (DNN) is a neural network including a plurality of hidden layers, e.g., two or more hidden layers. In some instances, each layer of the neural network includes a number of nodes (or "neurons"). In some embodiments, a node receives input that comes either directly from the input data or the output of nodes in previous layers, and performs a specific operation, e.g., a summation operation. In some embodiments, a connection from an input to a node is associated with a parameter (e.g., a weight and/or weighting factor). In some embodiments, the node sums up the products of all pairs of inputs, $x_i$, and their associated parameters. In some embodiments, the weighted sum is offset with a bias, b. In some embodiments, the output of a node or neuron is gated using a threshold or activation function, f, which, in some instances, is a linear or non-linear function. In some embodiments, the activation function is, for example, a rectified linear unit (ReLU) activation function, a Leaky ReLU activation function, or other function such as a saturating hyperbolic tangent, identity, binary step, logistic, arcTan, softsign, parametric rectified linear unit, exponential linear unit, softPlus, bent identity, softExponential, Sinusoid, Sine, Gaussian, or sigmoid function, or any combination thereof.

In some implementations, the weighting factors, bias values, and threshold values, or other computational parameters of the neural network, are "taught" or "learned" in a training phase using one or more sets of training data. For example, in some implementations, the parameters are trained using the input data from a training dataset and a gradient descent or backward propagation method so that the output value(s) that the ANN computes are consistent with the examples included in the training dataset. In some embodiments, the parameters are obtained from a back propagation neural network training process.

Any of a variety of neural networks are suitable for use in accordance with the present disclosure. Examples include, but are not limited to, feedforward neural networks, radial basis function networks, recurrent neural networks, residual neural networks, convolutional neural networks, residual convolutional neural networks, and the like, or any combination thereof. In some embodiments, the machine learning makes use of a pre-trained and/or transfer-learned ANN or deep learning architecture. In some implementations, convolutional and/or residual neural networks are used, in accordance with the present disclosure.

For instance, a deep neural network model includes an input layer, a plurality of individually parameterized (e.g., weighted) convolutional layers, and an output scorer. The parameters (e.g., weights) of each of the convolutional layers as well as the input layer contribute to the plurality of parameters (e.g., weights) associated with the deep neural network model. In some embodiments, at least 100 parameters, at least 1000 parameters, at least 2000 parameters or at least 5000 parameters are associated with the deep neural network model. As such, deep neural network models require a computer to be used because they cannot be mentally solved. In other words, given an input to the model, the model output needs to be determined using a computer rather than mentally in such embodiments. See, for example, Krizhevsky et al., 2012, "Imagenet classification with deep convolutional neural networks," in *Advances in Neural Information Processing Systems* 2, Pereira, Burges, Bottou, Weinberger, eds., pp. 1097-1105, Curran Associates, Inc.; Zeiler, 2012 "ADADELTA: an adaptive learning rate method," CoRR, vol. abs/1212.5701; and Rumelhart et al., 1988, "Neurocomputing: Foundations of research," ch. Learning Representations by Back-propagating Errors, pp. 696-699, Cambridge, MA, USA: MIT Press, each of which is hereby incorporated by reference.

Neural network algorithms, including convolutional neural network algorithms, suitable for use as models are disclosed in, for example, Vincent et al., 2010, "Stacked denoising autoencoders: Learning useful representations in a deep network with a local denoising criterion," J Mach Learn Res 11, pp. 3371-3408; Larochelle et al., 2009, "Exploring strategies for training deep neural networks," J Mach Learn Res 10, pp. 1-40; and Hassoun, 1995, Fundamentals of Artificial Neural Networks, Massachusetts Institute of Technology, each of which is hereby incorporated by reference. Additional example neural networks suitable for use as models are disclosed in Duda et al., 2001, *Pattern Classification*, Second Edition, John Wiley & Sons, Inc., New York; and Hastie et al., 2001, *The Elements of Statistical Learning*, Springer-Verlag, New York, each of which is hereby incorporated by reference in its entirety. Additional example neural networks suitable for use as models are also described in Draghici, 2003, *Data Analysis Tools for DNA Microarrays*, Chapman & Hall/CRC; and Mount, 2001, *Bioinformatics: sequence and genome analysis*, Cold Spring Harbor Laboratory Press, Cold Spring Harbor, New York, each of which is hereby incorporated by reference in its entirety.

Support vector machines. In some embodiments, the model is a support vector machine (SVM). SVM algorithms suitable for use as models are described in, for example, Cristianini and Shawe-Taylor, 2000, "An Introduction to Support Vector Machines," Cambridge University Press, Cambridge; Boser et al., 1992, "A training algorithm for optimal margin classifiers," in Proceedings of the 5th Annual ACM Workshop on Computational Learning Theory, ACM Press, Pittsburgh, Pa., pp. 142-152; Vapnik, 1998, Statistical Learning Theory, Wiley, New York; Mount, 2001, Bioinformatics: sequence and genome analysis, Cold Spring Harbor Laboratory Press, Cold Spring Harbor, N.Y.; Duda, Pattern Classification, Second Edition, 2001, John Wiley & Sons, Inc., pp. 259, 262-265; and Hastie, 2001, The Elements of Statistical Learning, Springer, New York; and Furey et al., 2000, Bioinformatics 16, 906-914, each of which is hereby incorporated by reference in its entirety. When used for classification, SVMs separate a given set of binary labeled data with a hyper-plane that is maximally distant from the labeled data. For certain cases in which no linear separation is possible, SVMs work in combination with the technique of 'kernels', which automatically realizes a non-linear mapping to a feature space. The hyper-plane found by the SVM in feature space corresponds, in some instances, to a non-linear decision boundary in the input space. In some embodiments, the plurality of parameters (e.g., weights) associated with the SVM define the hyper-plane. In some embodiments, the hyper-plane is defined by at least 10, at least 20, at least 50, or at least 100 parameters and the SVM model requires a computer to calculate because it cannot be mentally solved.

Naïve Bayes algorithms. In some embodiments, the model is a Naive Bayes algorithm. Naïve Bayes models suitable for use as models are disclosed, for example, in Ng et al., 2002, "On discriminative vs. generative classifiers: A comparison of logistic regression and naive Bayes," Advances in Neural Information Processing Systems, 14, which is hereby incorporated by reference. A Naive Bayes model is any model in a family of "probabilistic models" based on applying Bayes' theorem with strong (naïve) independence assumptions between the features. In some embodiments, they are coupled with Kernel density estimation. See, for example, Hastie et al., 2001, *The elements of statistical learning: data mining, inference, and prediction*, eds. Tibshirani and Friedman, Springer, New York, which is hereby incorporated by reference.

Nearest neighbor algorithms. In some embodiments, a model is a nearest neighbor algorithm. In some implementations, nearest neighbor models are memory-based and include no model to be fit. For nearest neighbors, given a query point $x_0$ (a test subject), the k training points $x_{(r)}$, $r, \ldots, k$ (here the training subjects) closest in distance to $x_0$ are identified and then the point $x_0$ is classified using the k nearest neighbors. In some embodiments, Euclidean distance in feature space is used to determine distance as $d_{(i)}=\|x_{(i)}-x_{(o)}\|$. Typically, when the nearest neighbor algorithm is used, the abundance data used to compute the linear discriminant is standardized to have mean zero and variance 1. In some embodiments, the nearest neighbor rule is refined to address issues of unequal class priors, differential misclassification costs, and feature selection. Many of these refinements involve some form of weighted voting for the neighbors. For more information on nearest neighbor analysis, see, Duda, *Pattern Classification*, Second Edition, 2001, John Wiley & Sons, Inc; and Hastie, 2001, The Elements of Statistical Learning, Springer, New York, each of which is hereby incorporated by reference.

A k-nearest neighbor model is a non-parametric machine learning method in which the input consists of the k closest training examples in feature space. The output is a class membership. An object is classified by a plurality vote of its neighbors, with the object being assigned to the class most common among its k nearest neighbors (k is a positive integer, typically small). If k=1, then the object is simply assigned to the class of that single nearest neighbor. See, Duda et al., 2001, *Pattern Classification*, Second Edition, John Wiley & Sons, which is hereby incorporated by reference. In some embodiments, the number of distance calculations needed to solve the k-nearest neighbor model is such that a computer is used to solve the model for a given input because it cannot be mentally performed.

Random forest, decision tree, and boosted tree algorithms. In some embodiments, the model is a decision tree. Decision trees suitable for use as models are described generally by Duda, 2001, Pattern Classification, John Wiley & Sons, Inc., New York, pp. 395-396, which is hereby incorporated by reference. Tree-based methods partition the feature space into a set of rectangles, and then fit a model (like a constant) in each one. In some embodiments, the decision tree is random forest regression. For example, one specific algorithm is a classification and regression tree (CART). Other specific decision tree algorithms include, but are not limited to, ID3, C4.5, MART, and Random Forests. CART, ID3, and C4.5 are described in Duda, 2001, Pattern Classification, John Wiley & Sons, Inc., New York, pp. 396-408 and pp. 411-412, which is hereby incorporated by reference. CART, MART, and C4.5 are described in Hastie et al., 2001, The Elements of Statistical Learning, Springer-Verlag, New York, Chapter 9, which is hereby incorporated by reference in its entirety. Random Forests are described in Breiman, 1999, "Random Forests—Random Features," Technical Report 567, Statistics Department, U.C. Berkeley, September 1999, which is hereby incorporated by reference in its entirety. In some embodiments, the decision tree model includes at least 10, at least 20, at least 50, or at least 100 parameters (e.g., weights and/or decisions) and requires a computer to calculate because it cannot be mentally solved.

Regression. In some embodiments, the model uses a regression algorithm. In some embodiments, a regression algorithm is any type of regression. For example, in some embodiments, the regression algorithm is logistic regression. In some embodiments, the regression algorithm is logistic regression with lasso, L2 or elastic net regularization. In some embodiments, those extracted features that have a corresponding regression coefficient that fails to satisfy a threshold value are pruned (removed from) consideration. In some embodiments, a generalization of the logistic regression model that handles multicategory responses is used as the model. Logistic regression algorithms are disclosed in Agresti, *An Introduction to Categorical Data Analysis*, 1996, Chapter 5, pp. 103-144, John Wiley & Son, New York, which is hereby incorporated by reference. In some embodiments, the model makes use of a regression model disclosed in Hastie et al., 2001, *The Elements of Statistical Learning*, Springer-Verlag, New York. In some embodiments, the logistic regression model includes at least 10, at least 20, at least 50, at least 100, or at least 1000 parameters (e.g., weights) and requires a computer to calculate because it cannot be mentally solved.

Linear discriminant analysis algorithms. In some embodiments, linear discriminant analysis (LDA), normal discriminant analysis (NDA), or discriminant function analysis is a generalization of Fisher's linear discriminant, a method used in statistics, pattern recognition, and machine learning to find a linear combination of features that characterizes or separates two or more classes of objects or events. In some embodiments, the resulting combination is used as the model (linear model) in some embodiments of the present disclosure.

Mixture model and Hidden Markov model. In some embodiments, the model is a mixture model, such as that described in McLachlan et al., Bioinformatics 18(3):413-422, 2002. In some embodiments, in particular, those embodiments including a temporal component, the model is a hidden Markov model such as described by Schliep et al., 2003, Bioinformatics 19(1):i255-i263.

Clustering. In some embodiments, the model is an unsupervised clustering model. In some embodiments, the model is a supervised clustering model. Clustering algorithms suitable for use as models are described, for example, at pages 211-256 of Duda and Hart, Pattern Classification and Scene Analysis, 1973, John Wiley & Sons, Inc., New York, (hereinafter "Duda 1973") which is hereby incorporated by reference in its entirety. As an illustrative example, in some embodiments, the clustering problem is described as one of finding natural groupings in a dataset. To identify natural groupings, two issues are addressed. First, a way to measure similarity (or dissimilarity) between two samples is determined. This metric (e.g., similarity measure) is used to ensure that the samples in one cluster are more like one another than they are to samples in other clusters. Second, a mechanism for partitioning the data into clusters using the similarity measure is determined. One way to begin a clustering investigation is to define a distance function and to compute the matrix of distances between all pairs of samples in the training set. If distance is a good measure of similarity, then the distance between reference entities in the same cluster is significantly less than the distance between the reference entities in different clusters. However, in some implementations, clustering does not use a distance metric. For example, in some embodiments, a nonmetric similarity function $s(x, x')$ is used to compare two vectors $x$ and $x'$. In some such embodiments, $s(x, x')$ is a symmetric function whose value is large when $x$ and $x'$ are somehow "similar." Once a method for measuring "similarity" or "dissimilarity" between points in a dataset has been selected, clustering uses a criterion function that measures the clustering quality of any partition of the data. Partitions of the dataset that extremize the criterion function are used to cluster the data. Particular exemplary clustering techniques contemplated for use in the present disclosure include, but are not limited to, hierarchical clustering (agglomerative clustering using a nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering. In some embodiments, the clustering includes unsupervised clustering (e.g., with no preconceived number of clusters and/or no predetermination of cluster assignments).

Ensembles of models and boosting. In some embodiments, an ensemble (two or more) of models is used. In some embodiments, a boosting technique such as AdaBoost is used in conjunction with many other types of learning algorithms to improve the performance of the model. In this approach, the output of any of the models disclosed herein, or their equivalents, is combined into a weighted sum that represents the final output of the boosted model. In some embodiments, the plurality of outputs from the models is combined using any measure of central tendency known in the art, including but not limited to a mean, median, mode, a weighted mean, weighted median, weighted mode, etc. In some embodiments, the plurality of outputs is combined using a voting method. In some embodiments, a respective model in the ensemble of models is weighted or unweighted.

As used herein, the term "parameter" refers to any coefficient or, similarly, any value of an internal or external element (e.g., a weight and/or a hyperparameter) in an algorithm, model, regressor, and/or classifier that affects (e.g., modify, tailor, and/or adjust) one or more inputs, outputs, and/or functions in the algorithm, model, regressor and/or classifier. For example, in some embodiments, a parameter refers to any coefficient, weight, and/or hyperparameter used to control, modify, tailor, and/or adjust the behavior, learning, and/or performance of an algorithm, model, regressor, and/or classifier. In some instances, a parameter is used to increase or decrease the influence of an input (e.g., a feature) to an algorithm, model, regressor, and/or classifier. As a nonlimiting example, in some embodiments, a parameter is used to increase or decrease the influence of a node (e.g., of a neural network), where the node includes one or more activation functions. Assignment of parameters to specific inputs, outputs, and/or functions is not limited to any one paradigm for a given algorithm, model, regressor, and/or classifier but is applicable to any suitable algorithm, model, regressor, and/or classifier architecture for a desired performance. In some embodiments, a parameter has a fixed value. In some embodiments, a value of a parameter is manually and/or automatically adjustable. In some embodiments, a value of a parameter is modified by a validation and/or training process for an algorithm, model, regressor, and/or classifier (e.g., by error minimization and/or backpropagation methods). In some embodiments, an algorithm, model, regressor, and/or classifier of the present disclosure includes a plurality of parameters. In some embodiments, the plurality of parameters is n parameters, where: $n \geq 2$; $n \geq 5$; $n \geq 10$; $n \geq 25$; $n \geq 40$; $n \geq 50$; $n \geq 75$; $n \geq 100$; $n \geq 125$; $n \geq 150$; $n \geq 200$; $n \geq 225$; $n \geq 250$; $n \geq 350$; $n \geq 500$; $n \geq 600$; $n \geq 750$; $n \geq 1,000$; $n \geq 2,000$; $n \geq 4,000$; $n \geq 5,000$; $n \geq 7,500$; $n \geq 10,000$; $n \geq 20,000$; $n \geq 40,000$; $n \geq 75,000$; $n \geq 100,000$; $n \geq 200,000$; $n \geq 500,000$, $n \geq 1 \times 10^6$, $n \geq 5 \times 10^6$, or $n \geq 1 \times 10^7$. As such, the algorithms, models, regressors, and/or classifiers of the present disclosure cannot be mentally performed. In some embodiments n is between 10,000 and $1 \times 10^7$, between 100,000 and $5 \times 10^6$, or between 500,000 and $1 \times 10^6$. In some embodiments, the algorithms, models, regressors, and/or classifier of the present disclosure operate in a k-dimensional space, where k is a positive integer of 5 or greater (e.g., 5, 6, 7, 8, 9, 10, etc.). As such, the algorithms, models, regressors, and/or classifiers of the present disclosure cannot be mentally performed.

As used herein, the term "untrained model" (e.g., "untrained classifier" and/or "untrained neural network") refers to a machine learning model or algorithm, such as a classifier or a neural network, that has not been trained on a target dataset. In some embodiments, "training a model" (e.g., "training a neural network") refers to the process of training an untrained or partially trained model (e.g., "an untrained or partially trained neural network"). Moreover, it will be appreciated that the term "untrained model" does not exclude the possibility that transfer learning techniques are used in such training of the untrained or partially trained model. For instance, Fernandes et al., 2017, "Transfer Learning with Partial Observability Applied to Cervical Cancer Screening," Pattern Recognition and Image Analysis: $8^{th}$ Iberian Conference Proceedings, 243-250, which is hereby incorporated by reference, provides non-limiting examples of such transfer learning. In instances where transfer learning is used, the untrained model described above is provided with additional data over and beyond that of the primary training dataset. Typically, this additional data is in the form of parameters (e.g., coefficients, weights, and/or hyperparameters) that were learned from another, auxiliary training dataset. Moreover, while a description of a single auxiliary training dataset has been disclosed, it will be appreciated that there is no limit on the number of auxiliary training datasets used to complement the primary training dataset in training the untrained model in the present disclosure. For instance, in some embodiments, two or more auxiliary training datasets, three or more auxiliary training datasets, four or more auxiliary training datasets or five or more auxiliary training datasets are used to complement the primary training dataset through transfer learning, where each such auxiliary dataset is different than the primary training dataset. Any manner of transfer learning is used, in some such embodiments. For instance, consider the case where there is a first auxiliary training dataset and a second auxiliary training dataset in addition to the primary training dataset. In such a case, the parameters learned from the first auxiliary training dataset (by application of a first model to the first auxiliary training dataset) are applied to the second auxiliary training dataset using transfer learning techniques (e.g., a second model that is the same or different from the first model), which in turn results in a trained intermediate model whose parameters are then applied to the primary training dataset and this, in conjunction with the primary training dataset itself, is applied to the untrained model. Alternatively, in another example embodiment, a first set of parameters learned from the first auxiliary training dataset (by application of a first model to the first auxiliary training dataset) and a second set of parameters learned from the second auxiliary training dataset (by application of a second model that is the same or different from the first model to the second auxiliary training dataset) are each individually applied to a separate instance of the primary training dataset (e.g., by separate independent matrix multiplications) and both such applications of the parameters to separate instances of the primary training dataset in conjunction with the primary training dataset itself (or some reduced form of the primary training dataset such as principal components or regression coefficients learned from the primary training set) are then applied to the untrained model in order to train the untrained model.

As used herein, the term "vector" is an enumerated list of elements, such as an array of elements, where each element has an assigned meaning. As such, the term "vector" as used in the present disclosure is interchangeable with the term "tensor." As an example, if a vector comprises the abundance counts, in a plurality of cells, for a respective cellular constituent, there exists a predetermined element in the vector for each one of the plurality of cells. For ease of presentation, in some instances a vector is described as being one-dimensional. However, the present disclosure is not so limited. A vector of any dimension, in some embodiments, is used in the present disclosure provided that a description of what each element in the vector represents is defined (e.g., that element 1 represents abundance count of cell 1 of a plurality of cells, etc.).

I. Exemplary System Embodiments

Figure 1B:
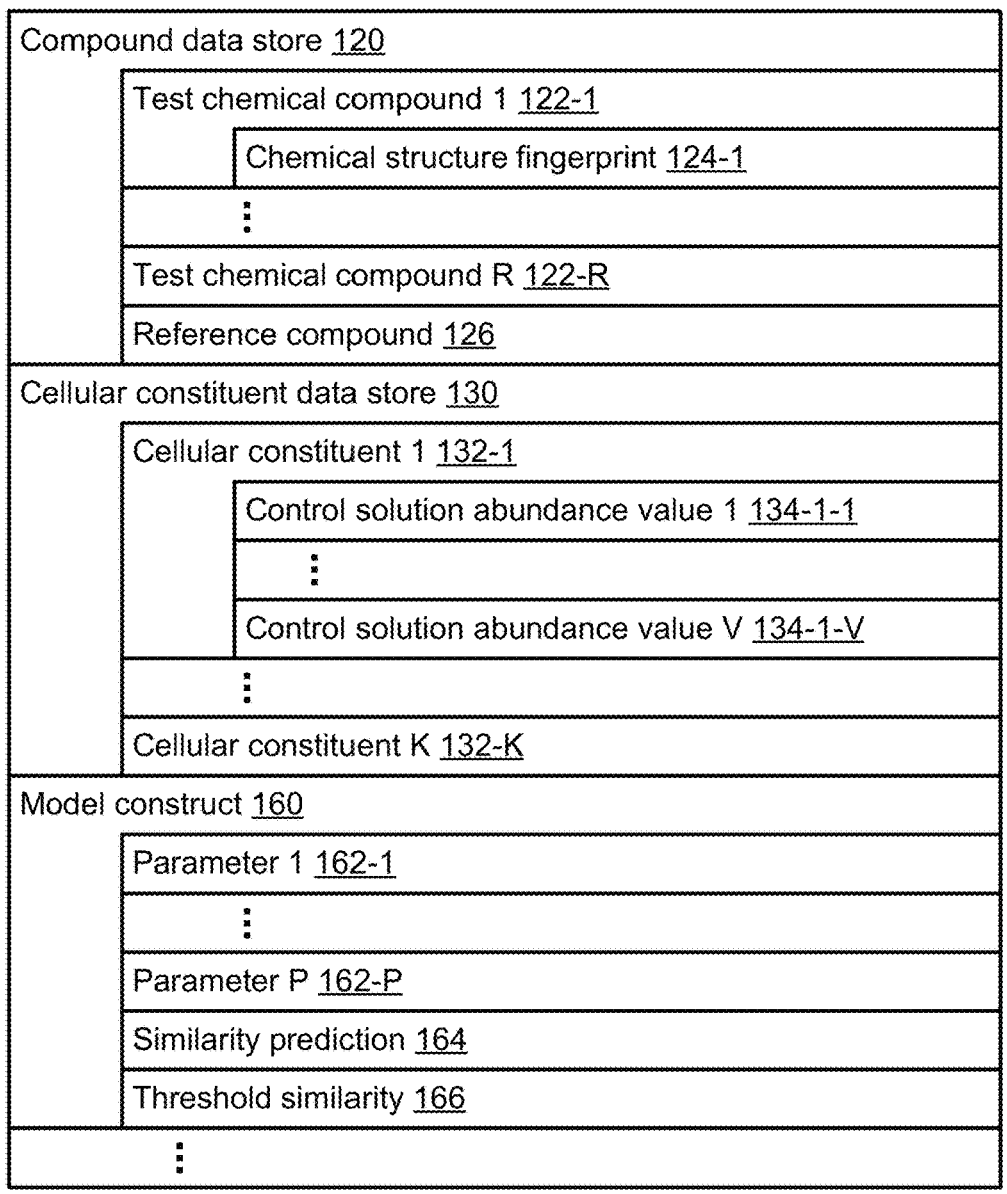
Figure 2A:
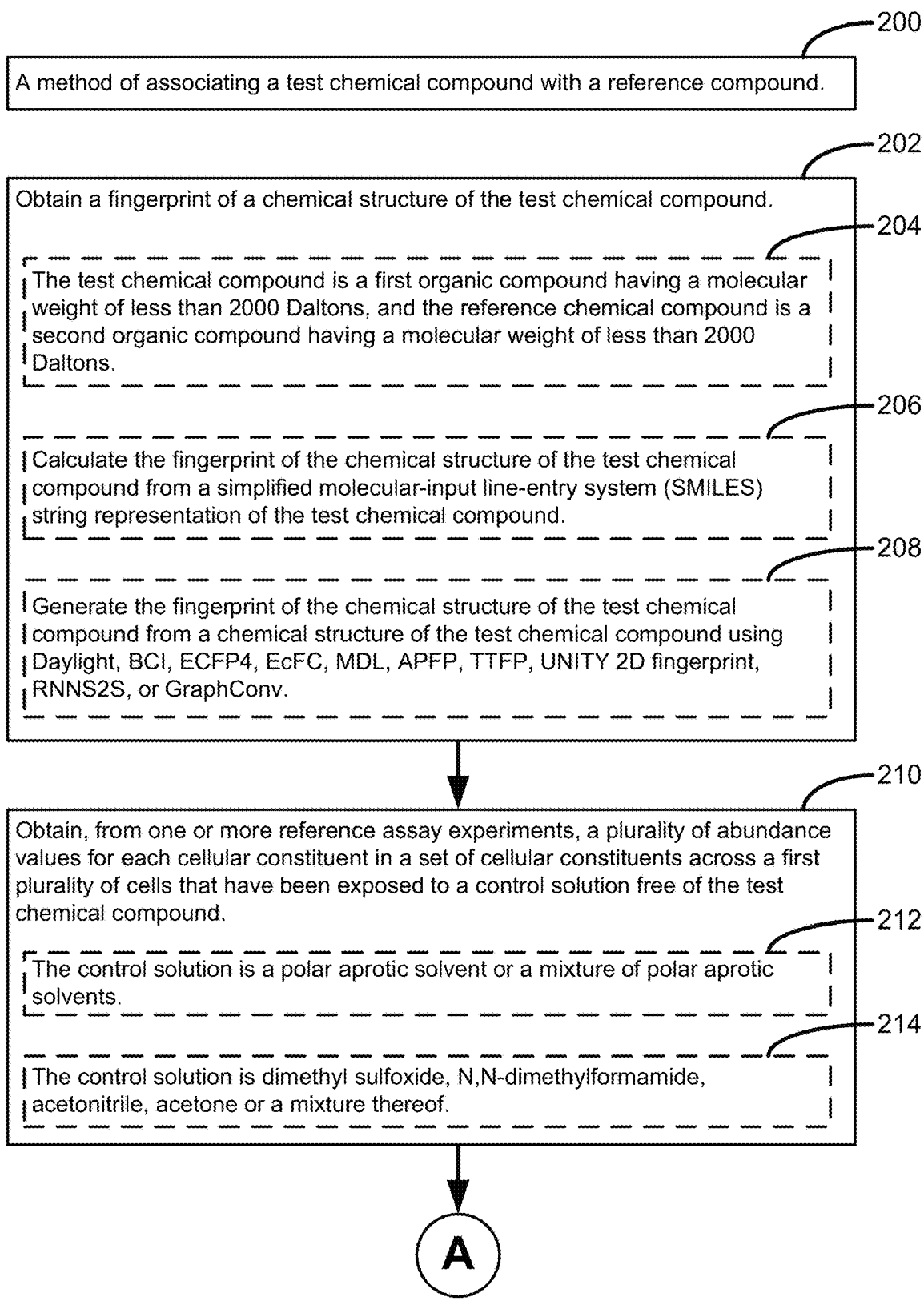
FIGS. 2A, 2B, 2C, 2D and 2E collectively provide a flow chart of processes and features of an example method for associating a test chemical compound with a reference compound, in which dashed boxes represent optional elements, in accordance with various embodiments of the present disclosure.
Figure 2B:
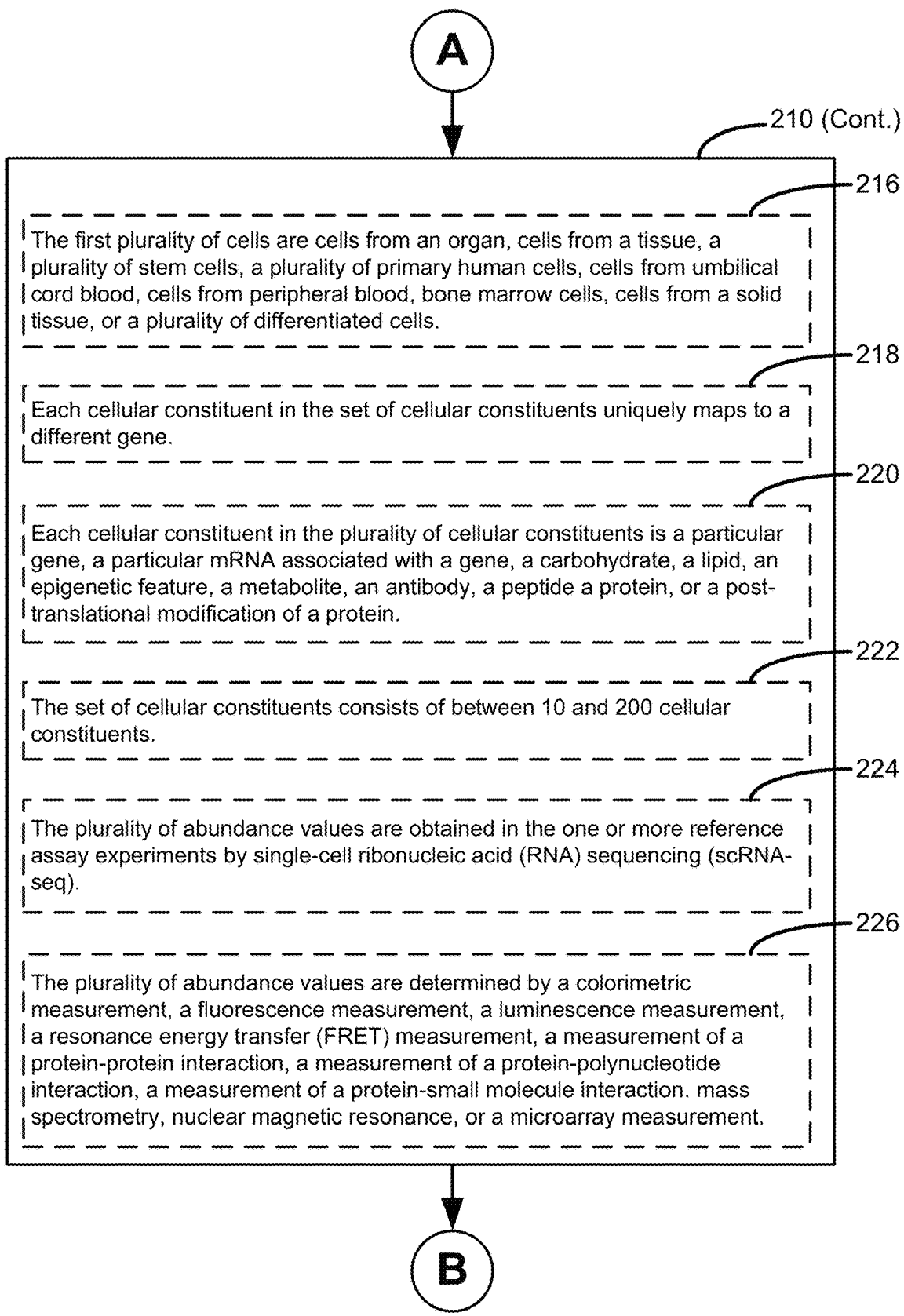
Figure 2C:
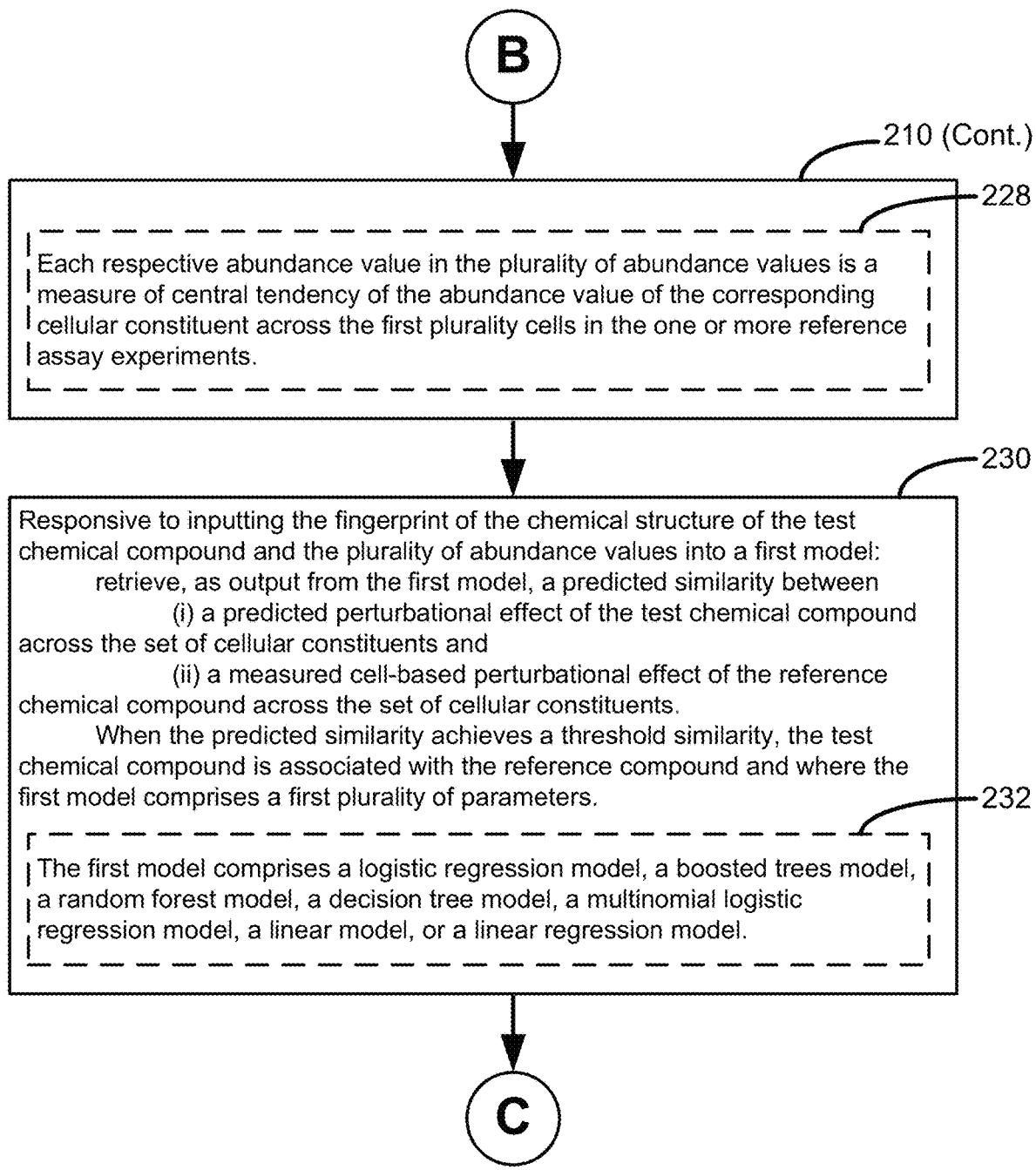
Figure 2D:
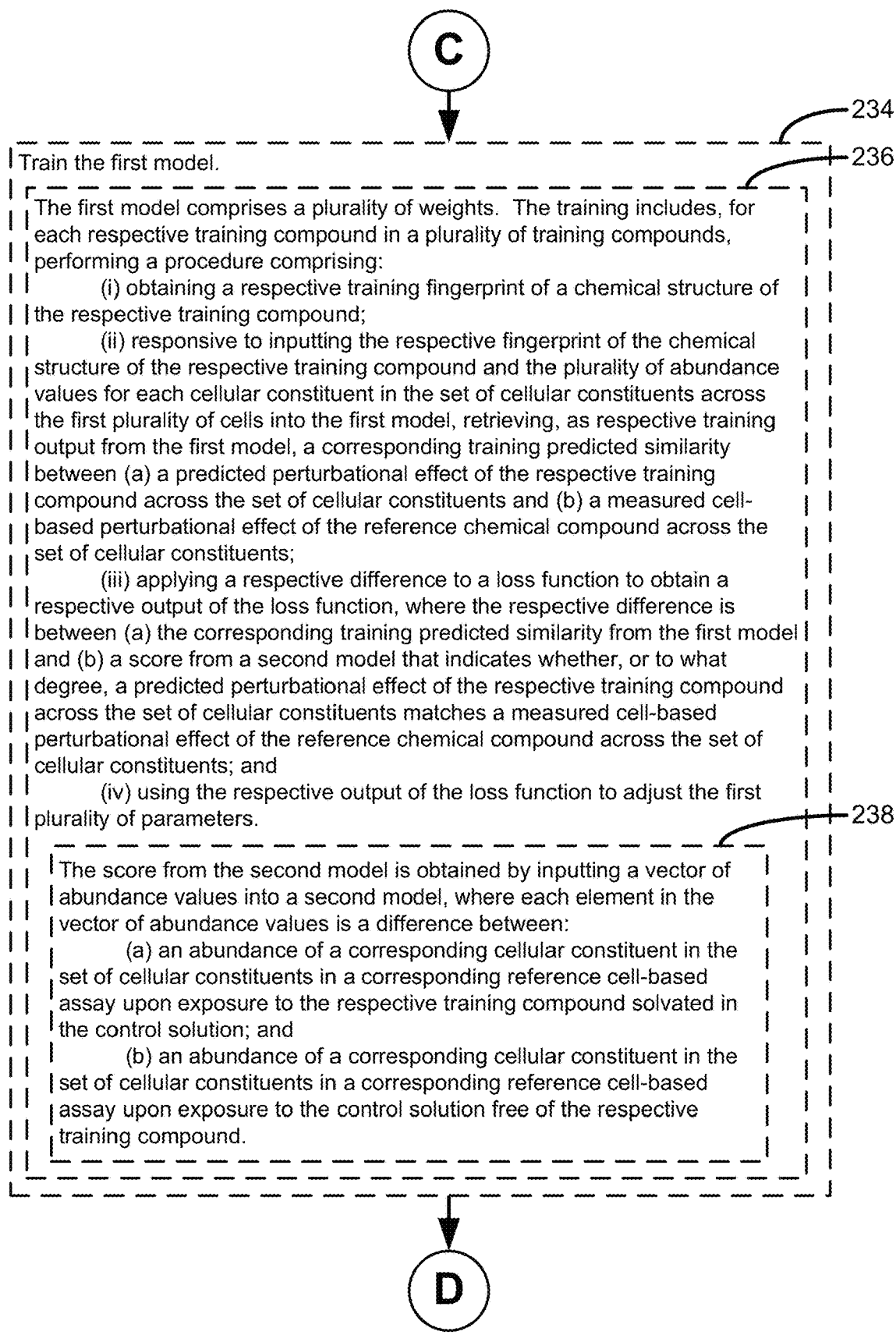
Figure 2E:
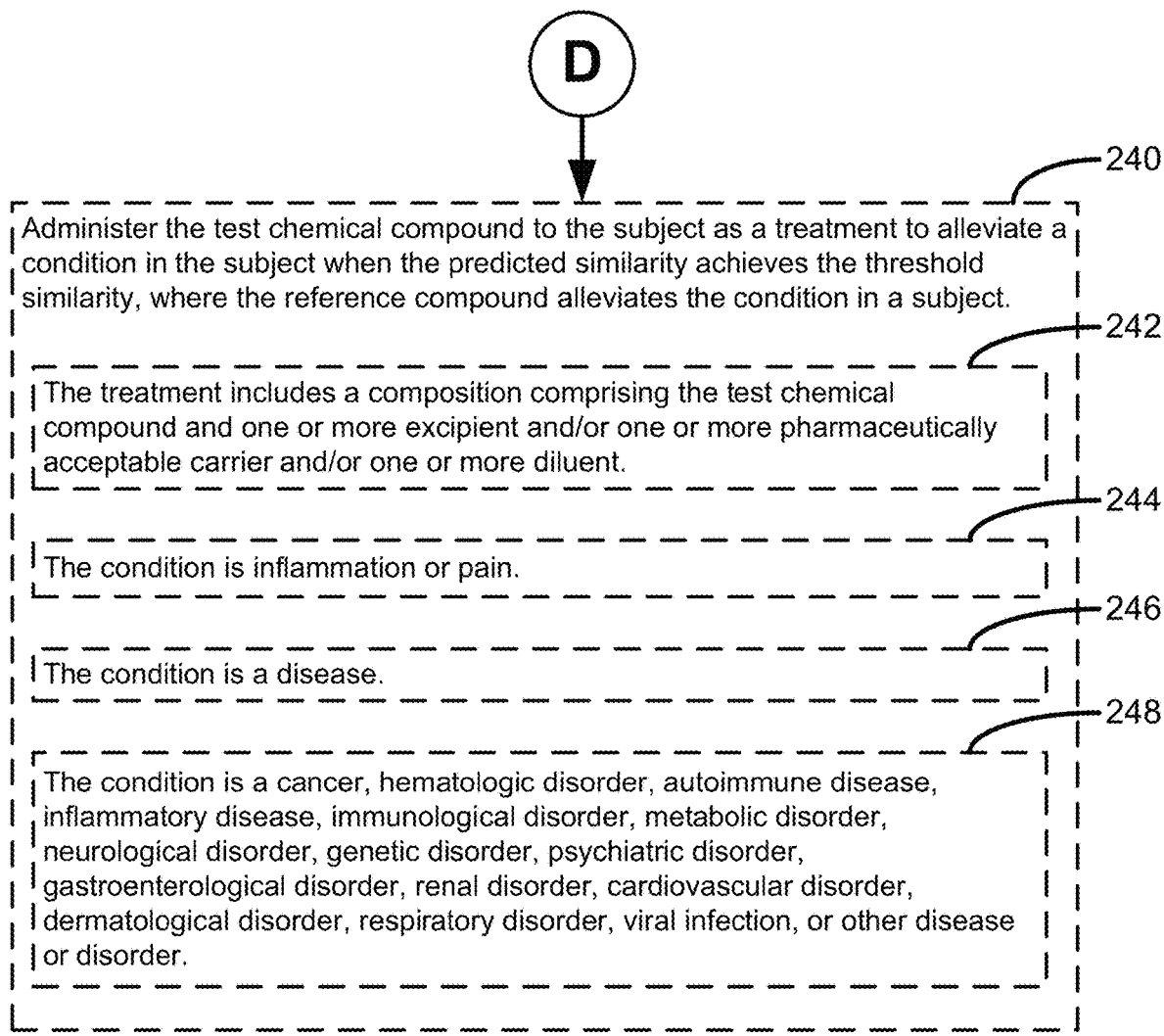

Now that an overview of some aspects of the present disclosure and some definitions used in the present disclosure have been provided, details of an exemplary system are described in conjunction with FIGS. 1A-B.

FIGS. 1A-B provides a block diagram illustrating a system 100 in accordance with some embodiments of the present disclosure. In some embodiments, the system 100 provides an association of a test chemical compound with a reference compound. In FIGS. 1A-B, the system 100 is illustrated as a computing device. Other topologies of the computer system 100 are possible. For instance, in some embodiments, the system 100 constitutes several computer systems that are linked together in a network or is virtual machine or a container in a cloud computing environment. As such, the exemplary topology shown in FIGS. 1A-B merely serves to describe the features of an embodiment of the present disclosure in a manner that will be readily understood to one of skill in the art.

Referring to FIGS. 1A-B, in some embodiments a computer system 100 (e.g., a computing device) includes a network interface 104. In some embodiments, the network interface 104 interconnects the system 100 computing devices within the system with each other, as well as optional external systems and devices, through one or more communication networks (e.g., through network communication module 158). In some embodiments, the network interface 104 optionally provides communication through network communication module 158 via the Internet, one or more local area networks (LANs), one or more wide area networks (WANs), other types of networks, or a combination of such networks.

Examples of networks include the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

The system 100 in some embodiments includes one or more processing units (CPU(s)) 102 (e.g., a processor, a processing core, etc.), one or more network interfaces 104, a user interface 106 including (optionally) a display 108 and an input system 105 (e.g., an input/output interface, a keyboard, a mouse, etc.) for use by the user, memory (e.g., non-persistent memory 107, persistent memory 109), and one or more communication buses 103 for interconnecting the aforementioned components. The one or more communication buses 103 optionally include circuitry (sometimes called a chipset) that interconnects and controls communications between system components. The non-persistent memory 107 typically includes high-speed random access memory, such as DRAM, SRAM, DDR RAM, ROM, EEPROM, flash memory, whereas the persistent memory 109 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 109 optionally includes one or more storage devices remotely located from the CPU(s) 102. The persistent memory 109, and the non-volatile memory device(s) within the non-persistent memory 109, include non-transitory computer readable storage medium. In some embodiments, the non-persistent memory 107 or alternatively the non-transitory computer readable storage medium stores the following programs, modules and data structures, or a subset thereof, sometimes in conjunction with the persistent memory 109:

- an optional operating system 156 (e.g., ANDROID, iOS, DARWIN, RTXC, LINUX, UNIX, OS X, WINDOWS, or an embedded operating system such as VxWorks), which includes procedures for handling various basic system services and for performing hardware dependent tasks;
- an optional network communication module (or instructions) 158 for connecting the system 100 with other devices and/or a communication network 104;
- a compound data store 120, optionally including a reference compound 126 and, for at least a first test chemical compound 122 (e.g., 122-1, . . . 122-R), a fingerprint of a chemical structure 124 (e.g., 124-1) of the test chemical compound;
- a cellular constituent data store 130, optionally including, for each cellular constituent 132 in a set of cellular constituents (e.g., 132-1, . . . 132-K), a plurality of abundance values 134 across a first plurality of cells that have been exposed to a control solution free of the test chemical compound (e.g., 134-1-1, . . . 134-1-V); and
- a model construct 160, optionally including a plurality of parameters 162 (e.g., 162-1, . . . 162-P), where:
  responsive to inputting the fingerprint of the chemical structure 124 of the test chemical compound and the plurality of abundance values 134, the model construct 160 outputs a predicted similarity 164 between (i) a predicted perturbational effect of the test chemical compound 122 across the set of cellular constituents 132 and (ii) a measured cell-based perturbational effect of the reference chemical compound 126 across the set of cellular constituents 132, and
  when the predicted similarity 164 achieves a threshold similarity 166, the test chemical compound 122 is associated with the reference compound 126.

In various embodiments, one or more of the above identified elements are stored in one or more of the previously mentioned memory devices and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 107 optionally stores a subset of the modules and data structures identified above. Furthermore, in some embodiments, the memory stores additional modules and data structures not described above. In some embodiments, one or more of the above identified elements is stored in a computer system, other than that of the system 100, that is addressable by the system 100 so that the system 100 may retrieve all or a portion of such data when needed.

Although FIGS. 1A-B depict a "system 100," the figures are intended more as a functional description of the various features that may be present in computer systems than as a structural schematic of the implementations described herein. In practice, and as recognized by those of ordinary skill in the art, items shown separately could be combined and some items could be separated. Moreover, although FIGS. 1A-B depict certain data and modules in non-persistent memory 107, some or all of these data and modules instead may be stored in persistent memory 109 or in more than one memory. For example, in some embodiments, at least compound data store 120 and cellular constituent data store 130 are stored in a remote storage device, such as a part of a cloud-based infrastructure. In some embodiments, at least compound data store 120 and cellular constituent data store 130 are stored on a cloud-based infrastructure. In some embodiments, compound data store 120 and cellular constituent data store 130 are also be stored in the remote storage device(s).

While a system in accordance with the present disclosure has been disclosed with reference to FIGS. 1A-B, a method 200 in accordance with the present disclosure are now detailed with reference to FIGS. 2A-E, 3, and 4A-E.

II. Embodiments for Associating a Test Chemical Compound with a Reference Compound Referring to FIGS. 2A-E, one aspect of the present disclosure provides a method 200 of associating a test chemical compound 122 with a reference compound 126. Conditions.

As described above, in some embodiments, a reference chemical compound is selected based on a corresponding perturbational effect, such as a cell behavior or phenotype that is associated with a condition. See, for example, the section entitled "Example Benefits," above.

In some embodiments, the reference compound modifies, alleviates, reverses, inhibits, or improves a condition in a subject. In some embodiments, the condition is inflammation or pain. In some embodiments, the condition is a disease.

In some embodiments, the condition is a cancer, hematologic disorder, autoimmune disease, inflammatory disease, immunological disorder, metabolic disorder, neurological disorder, genetic disorder, psychiatric disorder, gastroenterological disorder, renal disorder, cardiovascular disorder, dermatological disorder, respiratory disorder, viral infection, or other disease or disorder.

In some embodiments, the condition is a disease is selected from the group consisting of infectious or parasitic diseases; neoplasms; diseases of the blood or blood-forming organs; diseases of the immune system; endocrine, nutritional or metabolic diseases; mental, behavioral or neurodevelopmental disorders; sleep-wake disorders; diseases of the nervous system; diseases of the visual system; diseases of the ear or mastoid process; diseases of the circulatory system; diseases of the respiratory system; diseases of the digestive system; diseases of the skin; diseases of the musculoskeletal system or connective tissue; diseases of the genitourinary system; conditions related to sexual health; diseases related to pregnancy, childbirth or the puerperium; certain conditions originating in the perinatal period; and developmental anomalies. In some embodiments, the disease is one or more entries of the ICD-11 MMS, or the International Classification of Disease. The ICD provides a method of classifying diseases, injuries, and causes of death. The World Health Organization (WHO) publishes the ICDs to standardize the methods of recording and tracking instances of diagnosed disease.

In some embodiments, the condition is a disease stimulant such as a disease precondition or comorbidity.

In some embodiments, the condition occurs in, or is measured in the context of, a cell system. In some embodiments, the condition occurs in, or is measured in the context of, one or more cells, where the one or more cells includes single cells, bulk cells, cell lines, biopsy sample cells, and/or cultured primary cells. In some embodiments, the condition is a physiological condition occurring in human cells. In some embodiments, the condition is a physiological condition occurring in a sample, such as any of the samples described herein (see, for example, the section entitled "Definitions: Samples," above).

In some embodiments, the condition is, or is related to, a cellular process. In some embodiments, the cellular process is an aberrant cell process and/or a cell process associated with a disease. In some embodiments, the cellular process is indicative of or related to a mechanism underlying any of the characteristics of disease, including but not limited to onset, progression, symptoms, severity, and/or resolution of disease. In some embodiments, the cellular process is a functional pathway, a signaling pathway, and/or a mechanism of action (e.g., of a compound, a small molecule, and/or a therapeutic). In some embodiments, the cellular process is characterized and/or modulated by one or more genes. In some embodiments, the cellular process occurs during a transition between a first cell state and a second cell state.

In some embodiments, the condition is associated with an annotation, such as a gene set enrichment assay (GSEA) annotation, a gene ontology annotation, a functional or signaling pathway annotation, and/or a cellular signature annotation. In some embodiments, annotations are obtained from any public knowledge database, including but not limited to the NIH Gene Expression Omnibus (GEO), EBI ArrayExpress, NCBI, BLAST, EMBL-EBI, GenBank, Ensembl, the KEGG pathway database, the Library of Integrated Network-based Cellular Signatures (LINCS) L1000 dataset, the Reactome pathway database, and/or the Gene Ontology project.

In some embodiments, the condition is a phenotype. In some embodiments, the phenotype measured using experimental data including, but not limited to, flow cytometry readouts, imaging and microscopy annotations (e.g., H&E slides, IHC slides, radiology images, and/or other medical imaging), and/or cellular constituent data.

In some embodiments, the condition is a measure of toxicity. In some embodiments, the condition is inhibition or activation of a nuclear receptor, and/or an amount of inhibition or an amount of activation of a nuclear receptor. In some embodiments, the condition is inhibition or activation, and/or an amount of inhibition or an amount of activation of a biological pathway (e.g., a stress response pathway). Example nuclear receptors and example stress response pathways, as well as inhibition or activation data for these nuclear receptors and example stress response pathways that can be used in the present disclosure, are described for approximately 10,000 compounds as described in Huang et al., 2016, "Modelling the Tox21 10 K chemical profiles for in vivo toxicity prediction and mechanism characterization," Nat Commun. 7, p. 10425, which is hereby incorporated by reference.

In some embodiments, the condition is characterized by a modulation of one or more cellular constituents in a set of cellular constituents and/or a perturbation signature (e.g., a differential expression profile of a plurality of analytes in response to a perturbation). Any type of analyte (e.g., a gene, a transcript, a carbohydrate, a lipid, an epigenetic feature, a metabolite, a protein, or a combination thereof) is contemplated for use in the set of cellular constituents. In some embodiments, a respective cellular constituent is associated with any cellular or biological process known in the art, as well as any aberrations thereof, as will be apparent to one skilled in the art. Cellular constituent modules suitable for use with the presently disclosed systems and methods are further described in the section entitled "Cellular constituents," below.

In some embodiments, the condition is a perturbation signature characterized by a discrepancy between a first cell state and a second cell state (e.g., a cell state transition). In some such embodiments, the condition is characterized by a discrepancy between a diseased state (e.g., a cell obtained from a diseased subject and/or a diseased tissue) and a healthy state (e.g., a cell obtained from a healthy or control subject and/or tissue). For instance, in some embodiments, a diseased state is identified by loss of a function of a cell, gain of a function of a cell, progression of a cell (e.g., transition of the cell into a differentiated state), stasis of a cell (e.g., inability of the cell to transition into a differentiated state), intrusion of a cell (e.g., emergence of the cell in an abnormal location), disappearance of a cell (e.g., absence of the cell in a location where the cell is normally present), disorder of a cell (e.g., a structural, morphological, and/or spatial change within and/or around the cell), loss of network of a cell (e.g., a change in the cell that eliminates normal effects in progeny cells or cells downstream of the cell), a gain of network of a cell (e.g., a change in the cell that triggers new downstream effects in progeny cells of cells downstream of the cell), a surplus of a cell (e.g., an overabundance of the cell), a deficit of a cell (e.g., a density of the cell being below a critical threshold), a difference in cellular constituent ratio and/or quantity in a cell, a difference in the rate of transitions in a cell, or any combination thereof.

In embodiments, a cell state comprises a population of cells. In embodiments, the population of cells comprises or consists of a plurality of primary human cells. In some such embodiments the plurality of primary human cells comprises or consists of a plurality of CD34+ cells, a plurality of CD34+ hematopoietic stems, a plurality of progenitor cells (HSPC), a plurality of T-cells, a plurality of mesenchymal stem cells (MSC), a plurality of airway basal stem cells, or a plurality of induced pluripotent stem cells.

In some embodiments, the population of cells comprises or consists of human cell lines. In some such embodiments, the population of cells comprises or consists of cells from umbilical cord blood, from peripheral blood, or from bone marrow.

In some embodiments, the population of cells comprises or consists of cells in or from a solid tissue. In some such embodiments, the solid tissue is placenta, liver, heart, brain, kidney, or gastrointestinal tract.

In some embodiments, the population of cells comprises or consists of a plurality of differentiated cells. In some such embodiments, the plurality of differentiated cells comprises or consists of one or more of a plurality of megakaryocytes, a plurality of osteoblasts, a plurality of chondrocytes, a plurality of adipocytes, a plurality of hepatocytes, a plurality of hepatic mesothelial cells, a plurality of biliary epithelial cells, a plurality of hepatic stellate cells, a plurality of hepatic sinusoid endothelial cells, a plurality of Kupffer cells, a plurality of pit cells, a plurality of vascular endothelial cells, a plurality of pancreatic duct epithelial cells, a plurality of pancreatic duct cells, a plurality of centroacinous cells, a plurality of acinar cells, a plurality of islets of Langerhans, a plurality of cardiac muscle cells, a plurality of fibroblasts, a plurality of keratinocytes, a plurality of smooth muscle cells, a plurality of type I alveolar epithelial cells, a plurality of type II alveolar epithelial cells, a plurality of Clara cells, a plurality of ciliated epithelial cells, a plurality of basal cells, a plurality of goblet cells, a plurality of neuroendocrine cells, a plurality of kultschitzky cells, a plurality of renal tubular epithelial cells, a plurality of urothelial cells, a plurality of columnar epithelial cells, a plurality of glomerular epithelial cells, a plurality of glomerular endothelial cells, a plurality of podocytes, a plurality of mesangium cells, a plurality of nerve cells, a plurality of astrocytes, a plurality of microglia, or a plurality of oligodendrocytes.

In some embodiments, the population of cells comprises or consists of a cell type other than CD34+ cells.

In some embodiments, the population of cells comprises or consists of one or more cells selected from a hematopoietic stem cell (HSC) (including but not limited to an induced pluripotent stem cell (IPSC)), hepatocyte, cholangiocyte, mesenchymal cell, stellate cell (including but not limited to a hepatic stellate cell), fibroblast, smooth muscle cell, pericyte, endothelial cell, liver sinusoidal endothelial cell (LSEC), periportal endothelial cell (PPEC), peritoneal exudate cell (PEC), myeloid cells, Kupffer cell, monocyte, optionally a non-classical monocyte. macrophage, optionally scar-associated macrophage (SAM), dendritic cell, optionally a conventional type 1 dendritic cell (cDC1), conventional type 2 dendritic cell (cDC2), or plasmacytoid dendritic cell; neutrophil, T-cell, optionally a proliferated T-cell, natural killer (NK) cell, optionally a proliferated conventional NK cell or cytotoxic NK cell, B-cell, plasma cell, erythrocyte, and mast cell.

In some embodiments, the population of cells comprises or consists of one or more cells selected from basophils/mast cells, CD14+, erythroid lineage cells, hematopoietic precursor cells, lymphoid lineage cells, megakaryocyte-erythroid progenitor cells, megakaryocytes, and myeloid lineage cells.

In some embodiments, the population of cells comprises or consists of one or more cells selected from aB cell, T cell, basophil mast progenitor cell, common lymphoid progenitor, common myeloid progenitor, dendritic cell, erythroid lineage cell, erythroid progenitor cell, granulocyte monocyte progenitor cell, hematopoietic precursor cell, macrophage, mast cell, megakaryocyte-erythroid progenitor cell, mesenchymal cell, monocyte, natural killer cell, neutrophil, plasma cell, plasmacytoid dendritic cell, and pro-B cell.

In some embodiments, the population of cells comprises or consists of one or more cells selected from a basophil, eosinophil, erythroid progenitor cell, hematopoietic precursor cell, erythroid cell, megakaryocyte-erythroid progenitor cell, granulocyte monocyte progenitor, ery-mast transitioning, megakaryocyte progenitor cell, monocyte, and mast cell.

Compounds.

Referring to Block 202, in some embodiments, the method 200 includes obtaining a fingerprint of a chemical structure 124 of the test chemical compound 122.

In some embodiments, the test chemical compound is selected from a plurality of test chemical compounds.

In some embodiments, the plurality of test chemical compounds includes at least 5, at least 10, at least 15, at least 20, at least 30, at least 40, at least 50, at least 100, at least 200, at least 300, at least 400, at least 500, at least 800, at least 1000, at least 2000, at least 3000, at least 4000, at least 5000, at least 8000, at least 10,000, at least 20,000, at least 30,000, at least 50,000, at least 80,000, at least 100,000, at least 200,000, at least 500,000, at least 800,000, at least 1 million, or at least 2 million test compounds. In some embodiments, the plurality of test chemical compounds includes no more than 10 million, no more than 5 million, no more than 1 million, no more than 500,000, no more than 100,000, no more than 50,000, no more than 10,000, no more than 8000, no more than 5000, no more than 2000, no more than 1000, no more than 800, no more than 500, no more than 200, or no more than 100 test compounds. In some embodiments, the plurality of test chemical compounds consists of from 10 to 500, from 100 to 10,000, from 5000 to 200,000, or from 100,000 to 10 million test compounds. In some embodiments, the plurality of test chemical compounds falls within another range starting no lower than 5 test compounds and ending no higher than 10 million test compounds.

In some embodiments, the plurality of test chemical compounds includes the reference compound. In some embodiments, the plurality of test chemical compounds does not include the reference compound. In some embodiments, the plurality of test chemical compounds includes one or more analogs of the reference compound. For example, in some embodiments, a test chemical compound is a synthetic analog of the reference compound.

In some embodiments, the reference compound is selected from a plurality of reference compounds.

In some embodiments, the plurality of reference compounds includes at least 5, at least 10, at least 20, at least 50, at least 100, at least 200, at least 500, at least 800, at least 1000, at least 2000, at least 5000, at least 8000, or at least 10,000 reference compounds. In some embodiments, the plurality of reference compounds includes no more than 100,000, no more than 10,000, no more than 5000, no more than 2000, no more than 1000, no more than 800, no more than 500, no more than 200, or no more than 100 reference compounds. In some embodiments, the plurality of reference compounds consists of from 10 to 500, from 50 to 1000, from 500 to 20,000, or from 10,000 to 100,000 reference compounds. In some embodiments, the plurality of reference compounds falls within another range starting no lower than 5 reference compounds and ending no higher than 100,000 reference compounds.

In some embodiments, a respective test chemical compound and/or a respective reference compound is obtained from a database. In some embodiments, the database is a compound database that provides results from drug screens, annotations, and/or general information such as compound targets and chemical properties of compounds. Examples of suitable compound databases contemplated for use in the present disclosure include, but are not limited to, the Genomics of Drug Sensitivity in Cancer, the Cancer Therapeutics Response Portal, the Connectivity Map, PharmacoDB, the Base of Bioisosterically Exchangeable Replacements (BoBER), and/or DrugBank. In some embodiments, the database is a cellular constituent database that provides information on genes, gene products, perturbation-induced cellular constituent signatures, and/or pathway annotations. Examples of suitable cellular constituent databases contemplated for use in the present disclosure include, but are not limited to, the NIH Gene Expression Omnibus (GEO), EBI ArrayExpress, NCBI, BLAST, EMBL-EBI, GenBank, Ensembl, the KEGG pathway database, the Library of Integrated Network-based Cellular Signatures (LINCS) L1000 dataset, the Reactome pathway database, and/or the Gene Ontology project.

In some embodiments, a respective test chemical compound and/or reference compound is a small molecule, a biologic, a peptide, a protein, a protein combined with a small molecule, an antibody-drug conjugate (ADC), a nucleic acid, such as an siRNA or interfering RNA, a cDNA over-expressing wild-type and/or mutant shRNA, a cDNA over-expressing wild-type and/or mutant guide RNA (e.g., Cas9 system or other cellular-component editing system), and/or any combination of any of the foregoing.

In some embodiments, a respective test chemical compound and/or reference compound is inorganic or organic.

In some embodiments, a respective test chemical compound and/or a respective reference compound comprises at least 2, at least 5, at least 10, at least 20, at least 30, at least 40, or at least 50 amino acids. In some embodiments, a respective test chemical compound and/or a respective reference compound is a polymer that comprises no more than 60, no more than 50, no more than 40, no more than 30, no more than 20, or no more than 10 amino acids. In some embodiments, a respective test chemical compound and/or a respective reference compound consists of from 2 to 10, from 2 to 50, from 5 to 50, from 10 to 45, or from 35 to 60 amino acids. In some embodiments, a respective test chemical compound and/or a respective reference compound comprises a plurality of amino acids that falls within another range starting no lower than 2 amino acids and ending no higher than 60 amino acids.

In some embodiments, a respective test chemical compound and/or a respective reference compound has a molecular weight of at least 10 Da, at least 20 Da, at least 50 Da, at least 100 Da, at least 200 Da, at least 500 Da, at least 1 kDa, at least 2 kDa, at least 3 kDa, at least 5 kDa, at least 10 kDa, at least 20 kDa, at least 30 kDa, at least 50 kDa, at least 100 kDa, or at least 500 kDa. In some embodiments, a respective test chemical compound and/or a respective reference compound has a molecular weight of no more than 1000 kDa, no more than 500 kDa, no more than 100 kDa, no more than 50 kDa, no more than 10 kDa, no more than 5 kDa, no more than 2 kDa, no more than 1 kDa, no more than 500 Da, no more than 300 Da, no more than 100 Da, or no more than 50 Da. In some embodiments, a respective test chemical compound and/or a respective reference compound has a molecular weight of from 10 Da to 900 Da, from 50 Da to 1000 Da, from 100 Da to 2000 Da, from 1 kDa to 5 kDa, from 1 kDa to 10 kDa, from 5 kDa to 500 kDa, or from 100 kDa to 1000 kDa. In some embodiments, a respective test chemical compound and/or a respective reference compound has a molecular weight that falls within another range starting no lower than 10 Daltons and ending no higher than 1000 kDa.

In some embodiments, a respective test chemical compound and/or a respective reference compound is a small molecule. For instance, in some embodiments, a respective test chemical compound and/or a respective reference compound is an organic compound having a molecular weight of less than approximately 1000 Daltons (e.g., less than 900 Daltons).

In some embodiments, a respective test chemical compound and/or a respective reference compound is a peptide. For instance, in some embodiments, a respective test chemical compound and/or a respective reference compound is an organic compound having 41 amino acids or fewer. In some embodiments, a respective test chemical compound and/or a respective reference compound has a molecular weight of less than approximately 4500 Daltons (e.g., 41 amino acids*110 Daltons).

In some embodiments, a respective test chemical compound and/or a respective reference compound is a protein. For instance, in some embodiments, a respective test chemical compound and/or a respective reference compound is an organic compound having at least 42 amino acids. In some embodiments, a respective test chemical compound and/or a respective reference compound has a molecular weight of at least approximately 4600 Daltons (e.g., 42 amino acids*110 Daltons).

Referring to Block 204, in some embodiments, the test chemical compound is a first organic compound having a molecular weight of less than 2000 Daltons, and the reference chemical compound is a second organic compound having a molecular weight of less than 2000 Daltons.

Relative sizes of peptides and proteins are further described, for example, in CellGS, "The difference between peptides and proteins," 2022, available on the Internet at cellgs.com/blog/the-difference-between-peptides-and-proteins.html, which is hereby incorporated herein by reference in its entirety.

In some embodiments, a compound of the present disclosure (e.g., a test chemical compound and/or a reference compound) is a chemical compound that satisfies Lipinski's Rule of Five. In some embodiments, a compound of the present disclosure is an organic compound that satisfies two or more rules, three or more rules, or all four rules of the Lipinski's Rule of Five: (i) not more than five hydrogen bond donors (e.g., OH and NH groups), (ii) not more than ten hydrogen bond acceptors (e.g., N and O), (iii) a molecular weight under 500 Daltons, and (iv) a Log P under 5. For instance, in some embodiments, the test chemical compound satisfies any two or more rules, any three or more rules, or all four rules of the Lipinski's Rule of Five: (i) not more than five hydrogen bond donors, (ii) not more than ten hydrogen bond acceptors, (iii) a molecular weight under 500 Daltons, and (iv) a Log P under 5.

The "Rule of Five" is so called because three of the four criteria involve the number five. See, e.g., Lipinski, 1997, Adv. Drug Del. Rev. 23, 3, which is hereby incorporated herein by reference in its entirety. Moreover, Lipinski's Rule of Five (e.g., RO5) provides a set of guidelines used to evaluate druglikeness, such as to determine whether a respective compound with a respective pharmacological or biological activity has corresponding chemical or physical properties suitable for administration in humans. In some embodiments, a compound of the present disclosure satisfies one or more criteria in addition to Lipinski's Rule of Five. For example, in some embodiments, a compound of the present disclosure has five or fewer aromatic rings, four or fewer aromatic rings, three or fewer aromatic rings, or two or fewer aromatic rings.

In some embodiments, the method further includes transforming molecular data for the test chemical compound (e.g., the chemical structure of the compound) into a format that can be read and manipulated by a model, such as the first model.

One approach to transforming chemical structures into machine learning-readable formats includes determining a "fingerprint" of the chemical structure using a string representation of the chemical structure. In some embodiments, the string representation is in a SMARTS (SMARTS—A Language for Describing Molecular Patterns," 2022 on the Internet at daylight.com/dayhtml/doc/theory/theory.smarts.html (accessed December 2020), DeepSMILES (O'Boyle and Dalke, 2018, "DeepSMILES: an adaptation of SMILES for use in machine-learning of chemical structures," Preprint at ChemRxiv. https://doi.org/10.26434/chemrxiv.7097960.v1.), self-referencing embedded string (SELFIES) (Krenn et al., 2022, "SELFIES and the future of molecular string representations," Patterns 3(10), pp. 1-27), or simplified molecular-input line-entry system (SMILES) format. Molecular fingerprinting using SMILES strings is described, for example, in Honda et al., 2019, "SMILES Transformer: Pre-trained Molecular Fingerprint for Low Data Drug Discovery," arXiv:1911.04738, which is hereby incorporated herein by reference in its entirety.

Thus, in some embodiments, referring to Block 206, the method further includes calculating the fingerprint of the chemical structure of the test chemical compound from a string representation of the test chemical compound.

Another approach to transforming chemical structures into machine-learning readable formats includes determining a graph-based molecular fingerprint. In graph-based molecular fingerprinting, the original molecular structure is represented by a graph, in which nodes represent individual atoms and edges represent bonds between atoms. Graph-based approaches provide several advantages, including the ability to efficiently encode multiple substructures with lower size requirements and thus lower computational burden, as well as the ability to encode indications of structural similarity between fingerprints. Graph-based fingerprinting is further described, for instance, in Duvenaud et al., 2015, "Convolutional networks on graphs for learning molecular fingerprints," NeurIPS, 2224-2232, which is hereby incorporated herein by reference in its entirety. In some embodiments, the fingerprint is generated from a graph convolutional network. In some embodiments, the fingerprint is generated from a spatial graph convolutional network, such as a graph attention network (GAT), a graph isomorphism network (GIN), or a graph substructure index-based approximate graph (SAGA). In some embodiments, the fingerprint is generated from a spectral graph convolutional network, such as a spectral graph convolution using Chebyshev polynomial filtering.

Referring to Block 208, in some embodiments, the method further includes generating the fingerprint of the chemical structure of the test chemical compound from a chemical structure of the test chemical compound using Daylight, BCI, ECFP4, EcFC, MDL, APFP, TTFP, UNITY 2D fingerprint, RNNS2S, or GraphConv. A fingerprint of a compound is a digital digest of the compound. Nonlimiting examples of such a digital digest include Daylight fingerprints, a BCI fingerprint, an ECFC4 fingerprint, an ECFP4 fingerprint, an EcFC fingerprint, an MDL fingerprint, an atom pair fingerprint (APFP fingerprint), a topological torsion fingerprint (TTFP) fingerprint, a UNITY 2D fingerprint, an RNNS2S fingerprint, or a GraphConv fingerprint. See, Franco, 2014, "The Use of 2D fingerprint methods to support the assessment of structural similarity in orphan drug legislation," J. Cheminform 6, p. 5, and Rensi and Altman, 2017, "Flexible Analog Search with Kernel PCA Embedded Molecule Vectors," Computational and Structural Biotechnology Journal, doi:10.1016/j.csbj.2017.03.003, each of which is hereby incorporated by reference. See also, Raymond and Willett, 2002, "Effectiveness of graph-based and fingerprint-based similarity measures for virtual screening of 2D chemical structure databases," Journal of Computer-Aided Molecular Design 16, 59-71, and Franco et al., 2014, "The use of 2D fingerprint methods to support the assessment of structural similarity in orphan drug legislation" Journal of chemoinformatics 6(5), each of which is hereby incorporated by reference.

In some embodiments, the method further includes generating the fingerprint of the chemical structure of the test chemical compound from a chemical structure of the test chemical compound by inputting a string representation of the test chemical compound into each featurizer in a set of featurizers to obtain the fingerprint. In some embodiments, the set of featurizers consists of 1, 2, 3, or 4 featurizers in Table 4.

TABLE 4

Example featurizers

| Featurizer name | No. of features | Internet Reference, last accessed Dec. 6, 2023 |
|---|---|---|
| gin_supervised_edgepred | 300 | molfeat.datamol.io/featurizers/gin_supervised_edgepred |
| ECFP:4 | 2000 | molfeat.datamol.io/featurizers/ecfp |
| Desc2d | 211 | molfeat.datamol.io/featurizers/desc2D |
| MACCS | 167 | molfeat.datamol.io/featurizers/maccs |

In some embodiments, the fingerprint of the first compound 2108-1 is a concatenation of an output of each feature in the set of features in such embodiments. For instance, in an embodiment in which all four featurizers of Table 4 are used, the fingerprint of the test chemical compound consists of 300+2000+211+167 or 2678 features.

In some embodiments, the set of featurizers consists of between 2 and 40 featurizers in Table 5. In some embodiments, the feature representation of the test chemical compound is a concatenation of an output of each feature in the set of featurizers.

TABLE 5

Additional example featurizers

| Featurizer name | Internet Reference, last accessed Dec. 6, 2023 |
|---|---|
| Roberta-Zin480M-102M | molfeat.datamol.io/featurizers/Roberta-Zinc480M-102M |
| GPT2-Zinc480M-87M | molfeat.datamol.io/featurizers/GPT2-Zinc480M-87M |
| ChemGPT-1.2B | molfeat.datamol.io/featurizers/ChemGPT-1.2B |
| ChemGPT-19M | molfeat.datamol.io/featurizers/ChemGPT-19M |
| ChemGPT-4.7M | molfeat.datamol.io/featurizers/ChemGPT-4.7M |
| MolT5 | olfeat.datamol.io/featurizers/MolT5 |
| Desc3D | molfeat.datamol.io/featurizers/tags/physchem |
| Desc2d | molfeat.datamol.io/featurizers/desc2D |
| mordred | molfeat.datamol.io/featurizers/mordred |
| scaffoldkeys | molfeat.datamol.io/featurizers/scaffoldkeys |
| electroshape | molfeat.datamol.io/featurizers/electroshape |
| usrcat | molfeat.datamol.io/featurizers/usrcat |
| usr | molfeat.datamol.io/featurizers/usr |
| cats3d | molfeat.datamol.io/featurizers/cats3d |
| cats2d | molfeat.datamol.io/featurizers/cats2d |
| Pharm3D-cats | molfeat.datamol.io/featurizers/pharm3D-cats |
| Pharm2D-cats | molfeat.datamol.io/featurizers/pharm2D-cats |
| pharm2D-default | molfeat.datamol.io/featurizers/pharm2D-default |
| pharm3D-gobbi | molfeat.datamol.io/featurizers/pharm3D-gobbi |
| pharm3D-pmapper | molfeat.datamol.io/featurizers/pharm3D-pmapper |
| Pharm2D-pmapper | molfeat.datamol.io/featurizers/pharm2D-pmapper |
| ChemBERTa-77M-MTR | molfeat.datamol.io/featurizers/ChemBERTa-77M-MTR |
| ChemBERTa-77M-MLM | molfeat.datamol.io/featurizers/ChemBERTa-77M-MLM |
| atompair-count | molfeat.datamol.io/featurizers/atompair-count |
| topological-count | molfeat.datamol.io/featurizers/topological-count |
| fcfp-count | molfeat.datamol.io/featurizers/fcfp-count |
| ecfp-count | molfeat.datamol.io/featurizers/ecfp-count |
| estate | molfeat.datamol.io/featurizers/estate |
| Extended Reduced Graph approach (ErG) | molfeat.datamol.io/featurizers/erg |
| SMILES extended connectivity fingerprint (SECFP) | molfeat.datamol.io/featurizers/secfp |
| MinHashed atom-pair fingerprint up to a diameter of four bonds (MAP4) | molfeat.datamol.io/featurizers/map4 |
| pattern | molfeat.datamol.io/featurizers/pattern |
| rdkit | molfeat.datamol.io/featurizers/rdkit |
| topological | molfeat.datamol.io/featurizers/topological |
| Functional-class fingerprints (FCFPs) | molfeat.datamol.io/featurizers/fcfp |
| Extended-connectivity fingerprints (ECFPs) | molfeat.datamol.io/featurizers/ecfp |
| avalon | molfeat.datamol.io/featurizers/avalon |
| gin_supervised_masking | molfeat.datamol.io/featurizers/gin_supervised_masking |
| gin_supervised_infomax | molfeat.datamol.io/featurizers/gin_supervised_infomax |
| gin_supervised_edgepred | molfeat.datamol.io/featurizers/gin_supervised_edgepred |
| jtvae_zinc_no_kl | molfeat.datamol.io/featurizers/jtvae_zinc_no_kl |
| pcqm4mv2_graphormer_base | molfeat.datamol.io/featurizers/pcqm4mv2_graphormer_base |
| gin_supervised_contextpred | molfeat.datamol.io/featurizers/gin_supervised_contextpred |
| MACCS | molfeat.datamol.io/featurizers/maccs |

In some embodiments, a featurizer in the set of featurizers makes use of a deep graph convolutional neural network (e.g., Zhang et al, "An End-to-End Deep Learning Architecture for Graph Classification," The Thirty-Second AAAI Conference on Artificial Intelligence), GraphSage (e.g., Hamilton et al., 2017, "Inductive Representation Learning on Large Graphs," arXiv:1706.02216 [cs.SI]), a graph isomorphism network (e.g., Hu et al., 2018, "How Powerful are Graph Neural Networks," cs>arXiv:1810.00826, an edge-conditioned convolutional neural network (ECC) (e.g., Simonovsky and Komodakis, 2017, "Dynamic Edge-Conditioned Filters in Convolutional Neural Networks on Graphs," arXiv:1704.02901 [cs.CV]), a differentiable graph encoder such as DiffPool (e.g., Ying et al., 2018, "Hierarchical Graph Representation Learning with Differentiable Pooling" arXiv:1806.08804 [cs.LG]), a message-passing graph neural network such as MPNN (Gilmer et al., 2017, "Neural Message Passing for Quantum Chemistry," arXiv:1704.01212 [cs.LG]) or D-MPNN (Yang et al., 2019, "Analyzing Learned Molecular Representations for Property Prediction" J. Chem. Inf. Model. 59(8), pp. 3370-3388), or a graph neural network such as CMPNN (Song et al., "Communicative Representation Learning on Attributed Molecular Graphs," Proceedings of the Twenty-Ninth International Joint Conference on Artificial Intelligence (IJCAI-20)). See also Rao et al., 2021, "MolRep:A Deep Representation Learning Library for Molecular Property Prediction," doi.org/10.1101/2021.01.13.426489; posted Jan. 16, 2021. T; Rao et al., "Quantitative Evaluation of Explainable Graph Neural Networks for Molecular Property Prediction," arXiv preprint arXiv:2107.04119; and github.com/biomed-AI/MolRep.

In some embodiments, the fingerprint of the chemical structure of the test chemical compound is obtained as a vector representation (e.g., as a string). Any suitable method for obtaining vector representations of chemical structure fingerprints, including the methods and embodiments disclosed above, are contemplated for use in the present disclosure.

In some embodiments, the fingerprint of the chemical structure of the test chemical compound is concatenated to a vector that includes, for each cellular constituent in a set of cellular constituents, a plurality of abundance values obtained from one or more reference assay experiments across a first plurality of cells that have been exposed to a control solution free of the test chemical compound.

Cellular Constituents.

Referring to Block 210, in some embodiments, the method 200 further includes obtaining, from one or more reference assay experiments, a plurality of abundance values 134 for each cellular constituent 132 in a set of cellular constituents across a first plurality of cells that have been exposed to a control solution free of the test chemical compound.

In some embodiments, the control solution is a solution that is used to solvate the test chemical compound. Alternatively or additionally, in some embodiments, the control solution is a solution that is used to solvate the reference compound. In some embodiments, the control solution is a solution that is used to solvate one or more test chemical compound in a plurality of test chemical compounds and/or one or more reference compounds in a plurality of reference compounds.

In some embodiments, the control solution is an organic solvent.

Referring to Block 212, in some embodiments, the control solution is a polar aprotic solvent or a mixture of polar aprotic solvents. In some embodiments, the control solution is a polar protic solvent or a mixture of polar protic solvents.

Referring to Block 214, in some embodiments, the control solution is dimethyl sulfoxide (DMSO), N,N-dimethylformamide, acetonitrile, acetone or a mixture thereof. Alternatively or additionally, in some embodiments, the control solution is water, ethanol, methanol, methyl ethyl ketone, ethyl acetate, methylene chloride, chloroform, diethyl ether, toluene, hexanes, petroleum ether, or a mixture thereof. In some embodiments, the control solution is cell media.

Referring to Block 216, in some embodiments, the first plurality of cells are cells from an organ, cells from a tissue, a plurality of stem cells, a plurality of primary human cells, cells from umbilical cord blood, cells from peripheral blood, bone marrow cells, cells from a solid tissue, or a plurality of differentiated cells. In some embodiments, the first plurality of cells are obtained from a biological sample, such as any sample disclosed herein (see, e.g., the section entitled "Definitions: Samples," above). In some embodiments, the first plurality of cells includes adipocytes.

In some embodiments, the first plurality of cells includes at least 5, at least 10, at least 15, at least 20, at least 50, at least 100, at least 500, at least 800, at least 1000, at least 2000, at least 5000, at least 8000, at least 10,000, at least 50,000, at least 80,000, at least 100,000, at least 200,000, at least 500,000, at least 800,000, at least 1 million, or at least 2 million cells. In some embodiments, the first plurality of cells includes no more than 10 million, no more than 5 million, no more than 1 million, no more than 500,000, no more than 100,000, no more than 50,000, no more than 10,000, no more than 5000, no more than 2000, no more than 1000, no more than 500, no more than 200, or no more than 100 test compounds. In some embodiments, the first plurality of cells consists of from 10 to 500, from 100 to 10,000, from 5000 to 200,000, or from 100,000 to 10 million test compounds. In some embodiments, the first plurality of cells falls within another range starting no lower than 5 cells and ending no higher than 10 million cells.

Referring to Block 218, in some embodiments, each cellular constituent in the set of cellular constituents uniquely maps to a different gene. In some embodiments, two or more cellular constituents in the set of cellular constituents maps to the same gene (e.g., mRNA and pre-mRNA from a common gene).

In some embodiments, the set of cellular constituents includes nucleic acids, including DNA, modified (e.g., methylated) DNA, and/or RNA, including coding (e.g., mRNAs) or non-coding RNA (e.g., sncRNAs); proteins, including post-transcriptionally modified proteins; lipids; carbohydrates; nucleotides (e.g., adenosine triphosphate (ATP), adenosine diphosphate (ADP), and/or adenosine monophosphate (AMP)), including cyclic nucleotides such as cyclic adenosine monophosphate (cAMP) and cyclic guanosine monophosphate (cGMP); other small molecule cellular constituents such as oxidized and reduced forms of nicotinamide adenine dinucleotide (NADP/NADPH); and/or any combinations thereof.

For instance, referring to Block 220, in some embodiments, each cellular constituent in the set of cellular constituents is a particular gene, a particular mRNA associated with a gene, a carbohydrate, a lipid, an epigenetic feature, a metabolite, an antibody, a peptide a protein, or a post-translational modification of a protein. In some embodiments, the post-translational modification is selected from the group consisting of glycosylation, phosphorylation, acetylation, and ubiquitylation.

In some embodiments, the set of cellular constituents comprises 10 or more cellular constituents, 20 or more cellular constituents, 30 or more cellular constituents, 40 or more cellular constituents, or 50 or more cellular constituents. Referring to Block 222, in some embodiments, the set of cellular constituents consists of between 10 and 200 cellular constituents.

In some embodiments, the set of cellular constituents comprises at least 5, at least 10, at least 15, at least 20, at least 25, at least 30, at least 40, at least 50, at least 60, at least 70, at least 80, at least 90, at least 100, at least 200, at least 300, at least 400, at least 500, at least 600, at least 700, at least 800, at least 900, or at least 1000, at least 2000, at least 3000, at least 4000, at least 5000, at least 10,000, at least 30,000, at least 50,000, or more than 50,000 cellular constituents. In some embodiments, the set of cellular constitutes comprises no more than 100,000, no more than 50,000, no more than 10,000, no more than 5000, no more than 1000, no more than 500, no more than 200, no more than 100, no more than 50, or no more than 20 cellular constituents. In some embodiments, the set of cellular constituents consists of from 5 to 20, from 20 to 50, from 50 to 100, from 100 to 200, from 200 to 500, from 500 to 1000, from 1000 to 5000, from 5000 to 10,000, or from 10,000 to 50,000 cellular constituents. In some embodiments, the set of cellular constituents falls within another range starting no lower than 5 cellular constituents and ending no higher than 100,000 cellular constituents.

In some embodiments, for each cellular constituent in the set of cellular constituents, the corresponding plurality of abundance values comprises at least 5, at least 10, at least 20, at least 30, at least 40, at least 50, at least 100, at least 200, at least 500, at least 1000, at least 5000, at least 10,000, or at least 50,000 abundance values. In some embodiments, the corresponding plurality of abundance values comprises no more than 100,000, no more than 50,000, no more than 30,000, no more than 10,000, no more than 5000, no more than 1000, no more than 500, no more than 200, no more than 100, no more than 50, or no more than 10 abundance values. In some embodiments, the corresponding plurality of abundance values consists of from 5 to 50, from 20 to 200, from 80 to 1000, from 500 to 20,000, from 10,000 to 50,000, or from 20,000 to 100,000 abundance values. In some embodiments, the corresponding plurality of abundance values falls within another range starting no lower than 5 abundance values and ending no higher than 100,000 abundance values.

In some embodiments, the one or more reference assay experiments for the control solution are performed in replicate (e.g., for a plurality of droplets and/or a plurality of wells on an assay plate). In some such embodiments, for each respective cellular constituent in the set of cellular constituents, the one or more reference assay experiments generate a corresponding plurality of abundance values, where each respective abundance value in the corresponding plurality of abundance values corresponds to a respective replicate (e.g., a well and/or droplet) in a plurality of replicates. Abundance values and embodiments for obtaining the same, including replicates, are described elsewhere herein in greater detail (see, for example, the sections entitled "Abundance values" and "Second model (Classifier)," below).

In some embodiments, where the one or more reference assay experiments are performed in a plurality of wells (e.g., in one or more multi-well assay plates), each respective well in the plurality of wells comprises one or more cells. In some embodiments, each respective well in the plurality of wells comprises no more than 100,000, no more than 10,000, no more than 1000, no more than 100, no more than 10, no more than 5, or no more than 1 cell.

In some embodiments, a first respective cellular constituent in the set of cellular constituents has the same or a different number of abundance values in the corresponding plurality of abundance values as a second respective cellular constituent in the set of cellular constituents, other than the first respective cellular constituent.

In some embodiments, the set of cellular constituents is selected based on a preliminary correlation metric that is calculated using, for each respective training compound in a plurality of training compounds, for each respective candidate cellular constituent in a plurality of candidate cellular constituents, a difference between (a) an abundance of the respective candidate cellular constituent in a corresponding reference cell-based assay upon exposure to the respective training compound solvated in the control solution; and (b) an abundance of the corresponding cellular constituent in a corresponding reference cell-based assay upon exposure to the control solution free of the respective training compound.

In some such embodiments, for each respective candidate cellular constituent in the plurality of candidate cellular constituents, the preliminary correlation metric is obtained by performing a logistic regression analysis across the plurality of training compounds to determine a regression coefficient that indicates a probability that a differential abundance value for the respective candidate cellular constituent, for a respective training compound in the plurality of training compounds, is indicative of a similarity between the respective training compound and a reference compound. Accordingly, in some embodiments, the preliminary correlation metric is a logistic regression coefficient.

In some embodiments, the set of cellular constituents is obtained by selecting, from the plurality of candidate cellular constituents, each respective candidate cellular constituents having a preliminary correlation metric that satisfies a first selection criterion. In some embodiments, the first selection criterion is a ranking of the top N highest logistic regression coefficients. In other words, in some such embodiments, the set of cellular constituents was selected as the top N cellular constituents that were most predictive for similarity to the reference compound.

In some embodiments, N is at least 5, at least 10, at least 15, at least 20, at least 25, at least 30, at least 40, at least 50, at least 60, at least 70, at least 80, at least 90, at least 100, at least 200, at least 300, at least 400, at least 500, at least 600, at least 700, at least 800, at least 900, or at least 1000, at least 2000, at least 3000, at least 4000, at least 5000, at least 10,000, at least 30,000, at least 50,000, or more than 50,000. In some embodiments, N is no more than 100,000, no more than 50,000, no more than 10,000, no more than 5000, no more than 1000, no more than 500, no more than 200, no more than 100, no more than 50, or no more than 20. In some embodiments, N is from 5 to 20, from 20 to 50, from 50 to 100, from 100 to 200, from 200 to 500, from 500 to 1000, from 1000 to 5000, from 5000 to 10,000, or from 10,000 to 50,000. In some embodiments, N falls within another range starting no lower than 5 and ending no higher than 100,000.

Selection of cellular constituents is described in further detail elsewhere herein (see, for example, the section entitled "Second model (Classifier)" and Example 1, below).

Abundance Values.

Referring to Block 224, in some embodiments, the plurality of abundance values (e.g., for each respective cellular constituent in the set of cellular constituents) is obtained in the one or more reference assay experiments by single-cell ribonucleic acid (RNA) sequencing (scRNA-seq).

In some embodiments, the plurality of abundance values is determined by single-cell ribonucleic acid (RNA) sequencing (scRNA-seq), scTag-seq, single-cell assay for transposase-accessible chromatin using sequencing (scATAC-seq), CyTOF/SCoP, E-MS/Abseq, miRNA-seq, CITE-seq, and any combination thereof.

Referring to Block 226, in some embodiments, the plurality of abundance values is determined by a colorimetric measurement, a fluorescence measurement, a luminescence measurement, a resonance energy transfer (FRET) measurement, a measurement of a protein-protein interaction, a measurement of a protein-polynucleotide interaction, a measurement of a protein-small molecule interaction, mass spectrometry, nuclear magnetic resonance, or a microarray measurement.

In some embodiments, the plurality of abundance values for a respective cellular constituent is obtained across a plurality of replicates (e.g., experimental replicates, wells, droplets, and/or single cells), where each respective abundance value in the plurality of abundance values corresponds to a respective replicate in the plurality of replicates.

In some embodiments, the plurality of replicates is selected from: a plurality of matched wells, a plurality of wells obtained from a common assay plate, a plurality of wells obtained from across a plurality of assay plates, a plurality of wells obtained from a same single-cell assay experiment, and/or a plurality of wells obtained from across a plurality of single-cell assay experiments (e.g., different experimental and/or technical conditions).

For example, in some embodiments, the plurality of abundance values for a respective cellular constituent is obtained over a plurality of single-cell assay experiments, where each respective abundance value in the plurality of abundance values corresponds to a respective single-cell assay experiment in the plurality of single-cell assay experiments. In some embodiments, the plurality of abundance values for a respective cellular constituent is obtained across a plurality of wells, such as wells in a multi-well assay plate, where each respective abundance value in the plurality of abundance values corresponds to a respective well in the plurality of wells.

Various methods for obtaining the plurality of abundance values are possible, as will be apparent to one skilled in the art.

For instance, in some embodiments, the plurality of abundance values for a respective cellular constituent is obtained from a first respective assay experiment that includes, on a first respective plate comprising a plurality of wells, a first set of wells collectively including the first plurality of cells that have been exposed to the control solution free of the test chemical compound, and a second set of wells collectively including a second plurality of cells that have been exposed to the test chemical compound solvated in the control solution, where each respective well in the first set of wells matches a corresponding matched well in the second set of wells, and where each respective well in the first set of wells is subjected to a laboratory handing and analysis procedure that matches the laboratory handling and analysis of a corresponding well in the second set of wells.

In some embodiments, the plurality of abundance values for a respective cellular constituent is not obtained from a plurality of matched wells (e.g., the first set of wells and the second set of wells are subjected to different respective laboratory handling and analysis procedures).

In some embodiments, the plurality of abundance values for a respective cellular constituent is obtained from a first respective assay experiment that includes, on a first respective plate comprising a first plurality of wells, a first set of wells collectively including the first plurality of cells that have been exposed to the control solution free of the test chemical compound, and a second set of wells collectively including a second plurality of cells that have been exposed to the test chemical compound solvated in the control solution. In some embodiments, the first plurality of wells and the second plurality of wells has the same or different number of wells. In some embodiments, the first plurality of wells and the second plurality of wells are subjected to the same or different respective laboratory handling and analysis procedures.

In some embodiments, the plurality of abundance values for a respective cellular constituent is not obtained from the same plate (e.g., the plurality of abundance values for a respective cellular constituent is obtained from across a plurality of different plates).

In some embodiments, the plurality of abundance values for a respective cellular constituent is obtained from one or more assay experiments that includes, on one or more plates, where each respective plate comprises a respective plurality of wells, a first set of wells collectively including the first plurality of cells that have been exposed to the control solution free of the test chemical compound, and a second set of wells collectively including a second plurality of cells that have been exposed to the test chemical compound solvated in the control solution, where the one or more assay experiments are performed for the second set of wells together with the first set of wells (e.g., in the same run).

In some embodiments, the plurality of abundance values for a respective cellular constituent in the first set of wells is not obtained together with the second set of wells (e.g., the plurality of abundance values for a respective cellular constituent is obtained from across one or more different experimental runs and/or timepoints).

In some embodiments, the plurality of abundance values for a respective cellular constituent is obtained from one or more reference assay experiments used to train a second model (e.g., a transcriptional classifier). Second models (e.g., transcriptional classifiers) used for providing classifications of similarity are described in further detail elsewhere herein (see, for example, the section entitled "Second model (Classifier)," below).

Referring to Block 228, in some embodiments, each respective abundance value in the plurality of abundance values is a measure of central tendency of the abundance value of the corresponding cellular constituent across the first plurality of cells in the one or more reference assay experiments. For instance, in an example implementation, each respective abundance value in a corresponding plurality of abundance values for a respective cellular constituent is an average over a corresponding set of measurements of the respective cellular constituent, where each respective measurement is obtained from a respective cell in the first plurality of cells, in the one or more reference assay experiments.

In some embodiments, the measure of central tendency is any measure of central tendency known in the art, including but not limited to a mean, median, mode, weighted mean, weighted median, weighted mode, arithmetic mean, mid-range, midhinge, trimean, and/or Winsorized mean.

In some such embodiments, each respective abundance value in the plurality of abundance values is normalized. In some embodiments, the normalization is performed using a measure of dispersion. Any suitable measure of dispersion known in the art is contemplated for use in the present disclosure, including, but not limited to, variance, standard deviation, and/or standard error. In some embodiments, each respective abundance value in the plurality of abundance values is not normalized.

Alternatively or additionally, in some embodiments, for each respective cellular constituent in the set of cellular constituents, the method further includes determining a measure of central tendency (e.g., mean, median, mode, weighted mean, weighted median, weighted mode, arithmetic mean, midrange, midhinge, trimean, and/or Winsorized mean) over the corresponding plurality of abundance values. For instance, in another example implementation, for a respective cellular constituent in the set of cellular constituents, each respective abundance value in the corresponding plurality of abundance values corresponds to a different respective replicate in a plurality of replicates, and the method further includes averaging the corresponding plurality of abundance values over the plurality of replicates.

In some such embodiments, the method further includes normalizing the measure of central tendency over the plurality of abundance values (e.g., variance, standard deviation, and/or standard error). In some embodiments, the measure of central tendency over the plurality of abundance values is not normalized.

In some embodiments, the method includes formatting the plurality of abundance values for each cellular constituent in a set of cellular constituents as a vector, where each respective element in the vector corresponds to a respective cellular constituent and includes the corresponding plurality of abundance values, or a representation thereof, for the respective cellular constituent. Thus, in an example embodiment, an abundance vector includes, for each respective cellular constituent in the set of cellular constituents, a corresponding average of the corresponding plurality of abundance values for the respective cellular constituent.

In some embodiments, the abundance vector is concatenated to a vector that includes a fingerprint of the chemical structure of the test chemical compound.

Any one of a number of abundance counting techniques (e.g., cellular constituent measurement techniques) are contemplated for use in the present disclosure to obtain the corresponding plurality of abundance values for each respective cellular constituent in the set of cellular constituents over the first plurality of cells. For instance, Table 1 lists non-limiting techniques for cellular constituent measurements (e.g., single-cell cellular constituent measurements), in accordance with some embodiments of the present disclosure.

In some embodiments, the corresponding plurality of abundance values of a respective cellular constituent is obtained from expressed RNA or a nucleic acid derived therefrom (e.g., cDNA or amplified RNA derived from cDNA that incorporates an RNA polymerase promoter) from a respective cell in the first plurality of cells, including naturally occurring nucleic acid molecules and/or synthetic nucleic acid molecules. In some embodiments, the corresponding plurality of abundance values of a respective cellular constituent is obtained from such non-limiting sources as total cellular RNA, poly(A)+ messenger RNA (mRNA) or a fraction thereof, cytoplasmic mRNA, or RNA transcribed from cDNA (e.g., cRNA). Methods for preparing total and poly(A)+ RNA are well known in the art, and are described generally, e.g., in Sambrook, et al., Molecular Cloning: A Laboratory Manual (3rd Edition, 2001). In some embodiments, RNA is extracted from a cell of interest using guanidinium thiocyanate lysis followed by CsCl centrifugation (see, e.g., Chirgwin et al., 1979, Biochemistry 18:5294-5299), a silica gel-based column (e.g., RNeasy (Qiagen, Valencia, Calif.) or StrataPrep (Stratagene, La Jolla, Calif)), or using phenol and chloroform, as described in Ausubel et al., eds., 1989, Current Protocols In Molecular Biology, Vol. III, Green Publishing Associates, Inc., John Wiley & Sons, Inc., New York, at pp. 13.12.1-13.12.5). Poly(A)+ RNA is selected, in some embodiments, by selection with oligo-dT cellulose or, alternatively, by oligo-dT primed reverse transcription of total cellular RNA. In some embodiments, RNA is fragmented by methods known in the art, e.g., by incubation with ZnCl2, to generate fragments of RNA.

In some implementations, the cellular constituent abundance measurement technique is selected based on the desired cellular constituent to be measured. For instance, in some embodiments, scRNA-seq, scTag-seq, and/or miRNA-seq is used to measure RNA expression. Specifically, scRNA-seq measures expression of RNA transcripts, scTag-seq allows detection of rare mRNA species, and miRNA-seq measures expression of micro-RNAs. CyTOF/SCoP and E-MS/Abseq can be used to measure protein expression in the cell. CITE-seq simultaneously measures both gene expression and protein expression in the cell, and scATAC-seq measures chromatin conformation in the cell. Table 1 below provides example protocols for performing each of the cellular constituent abundance measurement techniques described above. In some embodiments, any of the protocols described in Table 1 of Shen et al., 2022, "Recent advances in high-throughput single-cell transcriptomics and spatial transcriptomics," Lab Chip 22, p. 4774, is used to measure the abundance of cellular constituents, such as genes, for the cellular constituent abundance data set.

TABLE 1

Example Measurement Protocols

| Technique | Protocol |
|---|---|
| RNA-seq | Olsen et al., (2018), "Introduction to Single-Cell RNA Sequencing," Current protocols in molecular biology 122(1), pg. 57. |
| Tag-seq | Rozenberg et al., (2016), "Digital gene expression analysis with sample multiplexing and PCR duplicate detection: A straightforward protocol," BioTechniques, 61(1), pg. 26. |
| ATAC-seq | Buenrostro et al., (2015), "ATAC-seq: a method for assaying chromatic accessibility genome-wide," Current protcols in molecular biology, 109(1), pg. 21. |

TABLE 1-continued

Example Measurement Protocols

| Technique | Protocol |
|---|---|
| miRNA-seq | Faridani et al., (2016), "Single-cell sequencing of the small-RNA transcriptome," Nature biotechnology, 34(12), pg. 1264. |
| CyTOF/SCoPE-MS/Abseq | Bandura et al., (2009), "Mass cytometry: technique for real time single cell multitarget immunoassay based on inductively coupled plasma time-of-flight mass spectrometry," Analytic chemistry, 81(16), pg. 6813. Budnik et al., (2018), "SCoPE-ME: mass spectrometry of single mammalian cells quantifies proteome heterogeneity during cell differentiation," Genome biology, 19(1), pg. 161. Shahi et al., (2017), "Abseq: Ultrahigh-throughput single cell protein profiling with droplet microfluidic barcoding," Scientific reports, 7, pg. 44447. |
| CITE-seq | Stoeckius et al., (2017), "Simultaneous epitope and transcriptome measurement in single cells," Nature Methods, 14(9), pg. 856. |

In some embodiments, the set of cellular constituents is measured at a single time point. In some embodiments, the set of cellular constituents is measured at multiple time points. For instance, in some embodiments, the set of cellular constituents is measured at multiple time points throughout a cell state transition (e.g., a differentiation process, a response to an exposure to a compound, a developmental process, etc.).

It is to be understood that this is by way of illustration and not limitation, as the present disclosure encompasses analogous methods using measurements of other cellular constituents obtained from cells (e.g., single cells and/or bulk cells). It is to be further understood that the present disclosure encompasses methods using measurements obtained directly from experimental work carried out by an individual or organization practicing the methods described in this disclosure, as well as methods using measurements obtained indirectly, e.g., from reports of results of experimental work carried out by others and made available through any means or mechanism, including data reported in third-party publications, databases, assays carried out by contractors, or other sources of suitable input data useful for practicing the disclosed methods.

In some embodiments, the corresponding abundance values for the set of cellular constituents across the first and/or second plurality of cells are preprocessed. In some embodiments, the preprocessing includes one or more of filtering, normalization, mapping (e.g., to a reference sequence), quantification, scaling, deconvolution, cleaning, dimension reduction, transformation, statistical analysis, and/or aggregation.

For example, in some embodiments, the plurality of abundance values for a respective cellular constituent is filtered based on a desired quality, e.g., size and/or quality of a nucleic acid sequence, or a minimum and/or maximum abundance value for a respective cellular constituent. In some embodiments, filtering is performed in part or in its entirety by various software tools, such as Skewer. See, Jiang, H. et al., BMC Bioinformatics 15(182):1-12 (2014). In some embodiments, the plurality of abundance values for a respective cellular constituent is filtered for quality control, for example, using a sequencing data QC software such as AfterQC, Kraken, RNA-SeQC, FastQC, or another similar software program. In some embodiments, the plurality of abundance values for a respective cellular constituent is normalized, e.g., to account for pull-down, amplification, and/or sequencing bias (e.g., mappability, GC bias etc.). See, for example, Schwartz et al., PLoS ONE 6(1):e16685 (2011) and Benjamini and Speed, Nucleic Acids Research 40(10): e72 (2012), the contents of which are hereby incorporated by reference, in their entireties, for all purposes. In some embodiments, the preprocessing removes a subset of abundance values from the plurality of abundance values. In some embodiments, the preprocessing the plurality of abundance values for a respective cellular constituent improves (e.g., lowers) a high signal-to-noise ratio.

In some embodiments, the preprocessing comprises performing a comparison of a corresponding abundance value for a respective cellular constituent in a respective cell to a reference abundance. In some embodiments, the reference abundance is obtained from, e.g., a normal sample, a matched sample, a reference dataset comprising reference abundance values, a reference cellular constituent such as a housekeeping gene, and/or a reference standard. In some embodiments, the comparison is performed using any differential expression test including, but not limited to, a difference of means test, a Wilcoxon rank-sum test (Mann Whitney U test), a t-test, a logistic regression, and a generalized linear model. Those of skill in the art will appreciate that other metrics are also possible for comparison and/or normalization of cellular constituent abundances.

In some embodiments, each respective abundance value in the plurality of abundance values for a respective cellular constituent comprises any one of a variety of forms, including, without limitation, a raw abundance value, an absolute abundance value (e.g., transcript number), a relative abundance value, a compound or aggregated abundance value, a transformed abundance value (e.g., log 2 and/or log 10 transformed), a change (e.g., fold- or log-change) relative to a reference (e.g., a normal sample, matched sample, reference dataset, housekeeping gene, and/or reference standard), a standardized abundance value, a measure of central tendency (e.g., mean, median, mode, weighted mean, weighted median, and/or weighted mode), a measure of dispersion (e.g., variance, standard deviation, and/or standard error), an adjusted abundance value (e.g., normalized, scaled, and/or error-corrected), a dimension-reduced abundance value (e.g., principal component vectors and/or latent components), and/or a combination thereof. Methods for obtaining cellular constituent abundances using dimension reduction techniques are known in the art and further detailed below, including but not limited to principal component analysis, factor analysis, linear discriminant analysis, multi-dimensional scaling, isometric feature mapping, locally linear embedding, hessian eigenmapping, spectral embedding, t-distributed stochastic neighbor embedding, and/or any substitutions, additions, deletions, modification, and/or combinations thereof as will be apparent to one skilled in the art. See, for example, Sumithra et al., 2015, "A Review of Various Linear and Non Linear Dimensionality Reduction Techniques," Int J Comp Sci and Inf Tech, 6(3), 2354-2360, which is hereby incorporated herein by reference in its entirety.

In some embodiments, the plurality of abundance values for a respective cellular constituent is obtained from a database. Examples of suitable databases that provide results from drug screens, annotations, and/or general information such as compound targets and chemical properties of compounds include, but are not limited to, the Genomics of Drug Sensitivity in Cancer, the Cancer Therapeutics Response Portal, the Connectivity Map, PharmacoDB, the Base of Bioisosterically Exchangeable Replacements (BoBER), and/or DrugBank. In some embodiments, the plurality of abundance values for a respective cellular constituent is selected from a database that provides information on genes and gene products, perturbation-induced cellular constituent signatures, and/or pathway annotations. Examples of suitable databases include, but are not limited to, the NIH Gene Expression Omnibus (GEO), EBI ArrayExpress, NCBI, BLAST, EMBL-EBI, GenBank, Ensembl, the KEGG pathway database, the Library of Integrated Network-based Cellular Signatures (LINCS) L1000 dataset, the Reactome pathway database, and/or the Gene Ontology project.

In some embodiments, the plurality of abundance values for a respective cellular constituent is obtained using any of the methods disclosed in U.S. patent application Ser. No. 16/511,691 entitled "Methods of Analyzing Cells," filed Jul. 15, 2019, which is hereby incorporated herein by reference.

Similarity Predictions.

Referring to Block 230, in some embodiments, the method 200 further includes, responsive to inputting the fingerprint of the chemical structure 124 of the test chemical compound 122 and the plurality of abundance values 134 into a first model 160, retrieving, as output from the first model, a predicted similarity 164 between (i) a predicted perturbational effect of the test chemical compound 122 across the set of cellular constituents 132 and (ii) a measured cell-based perturbational effect of the reference chemical compound 126 across the set of cellular constituents 132. When the predicted similarity 164 achieves a threshold similarity, the test chemical compound 122 is associated with the reference compound 126 and wherein the first model comprises a first plurality of parameters 162.

In some embodiments, the predicted perturbational effect is selected from the group consisting of an IC50, a measure of differential gene expression, a log fold change, a ddCq value, a measure of apoptosis, a staining intensity, a textural pattern, a size of a cell or a cellular structure thereof, a shape of a cell or a cellular structure thereof, and any correlation or adjacency relationship thereof. Non-limiting examples of perturbational effects contemplated for use in the present disclosure are further disclosed elsewhere herein (see, e.g., the section entitled "Further embodiments," below).

In some embodiments, as discussed above, the fingerprint of the chemical structure of the test chemical compound and the plurality of abundance values are inputted into the first model as a concatenated vector. An example schematic for a concatenated input vector, including a vector representation of a fingerprint of a chemical structure and a vector representation of a plurality of abundance values for a control solution, for input to the first model is provided, for instance, in FIG. 4E.

In general, what is sought is a test chemical compound that is associated with (as demonstrated by having a predicted similarity satisfying the threshold similarity) the reference compound. For instance, in some embodiments, satisfaction of the threshold similarity is obtained when the predicted similarity is above or below a first predetermined numerical value.

For instance, in some embodiments, the predicted similarity is expressed as a normalized continuous value between "0" and "1" (or some other range "A" to "B" where A and B are two different numbers), where values closer to "1" (e.g., 0.89, 0.90, 0.91, 0.92, etc.) indicate a strong association between a test chemical compound and the reference compound. Values closer to "0" (e.g., 0.01, 0.02, 0.03, 0.04, etc.) indicate poor or no association between the test chemical compound and the reference compound. In such instances, a threshold similarity is chosen between "0" and "1" (or some other range "A" to "B" where A and B are two different numbers) and test chemical compound is deemed to be associated with the reference compound when the predicted similarity is above the threshold similarity, whereas the test chemical compound is deemed not to be associated with the reference compound when the predicted similarity is below the threshold similarity. In some such embodiments, the predicted similarity is expressed as a normalized value in a continuous scale between "0" and "1" (or some other range "A" to "B" where A and B are two different numbers) and the threshold similarity is a value between 0 and 1, between 0.10 and 0.90, between 0.05 and 0.30, between 0.10 and 0.20, between 0.05 and 0.40, between 0.12 and 0.50, between 0.20 and 0.80, between 0.30 and 0.70, between 0.50 and 0.99, between 0.60 and 0.99, between 0.70 and 0.99, between 0.80 and 0.99, or between 0.90 and 0.99.

As another example, in some embodiments, the similarity is expressed as a normalized value on continuous scale between "0" and "1" (or some other range "A" to "B" where A and B are two different numbers), where values closer to "1" (e.g., 0.89, 0.90, 0.91, 0.92, etc.) indicate no association between a test chemical compound and a reference compound. Values closer to "0" (e.g., 0.01, 0.02, 0.03, 0.04, etc.) indicate association between the test chemical compound and the reference compound. In such instances, a threshold similarity is chosen between "0" and "1" (or some other range "A" to "B" where A and B are two different numbers) and the test chemical compound is deemed to be associated with the physiological condition of interest when the predicted similarity is below the threshold similarity, whereas the test chemical compound is deemed not to be associated with the physiological condition of interest when the predicted similarity is above the threshold similarity. In some such embodiments, the predicted similarity is expressed as a normalized value in a continuous scale between "0" and "1" (or some other range "A" to "B" where A and B are two different numbers) and the threshold similarity is a value between 0 and 1, between 0.10 and 0.90, between 0.05 and 0.30, between 0.10 and 0.20, between 0.05 and 0.40, between 0.12 and 0.50, between 0.20 and 0.80, between 0.30 and 0.70, between 0.50 and 0.99, between 0.60 and 0.99, between 0.70 and 0.99, between 0.80 and 0.99, or between 0.90 and 0.99.

In some embodiments, the threshold similarity is manually defined by a user. In some embodiments, the threshold similarity is determined using an optimization process.

For example, in some embodiments, the threshold similarity is determined by varying the threshold similarity during a training process for the first model. In some such embodiments, the threshold similarity is set to a value such that each respective training compound in a plurality of training compounds that is labeled as associated with the reference compound is accurately deemed to be associated with the reference compound based on a comparison between the predicted similarity and the threshold similarity. In other words, in some such embodiments, the threshold similarity is set to a value such that known "hits" are accurately detected by the first model as such. Alternatively or additionally, in some such embodiments, the threshold similarity is set to a value such that each respective training compound in a plurality of training compounds that is labeled as not associated with the reference compound is accurately deemed not to be associated with the reference compound based on a comparison between the predicted similarity and the threshold similarity. In other words, in some such embodiments, the threshold similarity is set to a value such that known "non-hits" are accurately detected by the first model as such. In some embodiments, the threshold similarity is set to a value such that a performance metric for the first model satisfies a threshold criterion. For example, in some embodiments, the threshold criterion for the performance metric is a false positive rate of 0.05 or less.

Various methods for determining threshold similarities based on target performance metrics are possible and will be understood to be contemplated for use in the present disclosure, as will be apparent to one skilled in the art. An example implementation for defining a threshold similarity is described in Example 1, below.

First Model (Structure Behavior Relationship).

In some embodiments, any suitable model architecture disclosed herein is contemplated for use in the present disclosure as the first model.

In some embodiments, the first model is a logistic regression model.

Generally, logistic regression models seek to determine the probability that one or more independent variables (e.g., chemical structure and/or abundance values) relate to an outcome (e.g., association with a reference compound and/or predicted similarity). Particularly, in some embodiments, the first model attempts to determine a probability that a test chemical compound is similar to a reference compound based on the fingerprint of the chemical structure of the test chemical compound and the plurality of abundance values for each respective cellular constituent in the set of cellular constituents (e.g., a transcriptional profile induced by the control solution free of the test chemical compound). Using logistic regression, in some such embodiments, the predicted similarity generated by the first model is a probability that falls between 0 and 1, based on the input chemical structure and/or abundance values.

In some embodiments, the first model is a multiple logistic regression model. Generally, multiple logistic regression algorithms seek to determine the relationship between a plurality of independent variables (e.g., a multidimensional input, such as a chemical structure and/or a plurality of abundance values) and an outcome (e.g., association with a reference compound and/or predicted similarity). In some embodiments, this takes the form of $y \sim x_1 + x_2 + x_3 + \ldots + x_n$, for n independent variables x and outcome y.

For instance, in some such embodiments, the plurality of abundance values for each respective cellular constituent in the set of cellular constituents represents a different independent variable that modulates the probability of association. In some embodiments, one or more correlations exist between all or a subset of the plurality of independent variables.

In some embodiments, the first model is an algorithm for gradient boosting on decision trees. In some embodiments, the first model is CatBoost or XGBoost.

Generally, gradient boosted decision trees utilize a "decision tree" structure in which each split in the ensemble model corresponds to a component model (e.g., a "tree" that splits into two or more nodes or "leaves") that acts as a weak learner. Each "leaf" (e.g., node) includes a function that generates an intermediate output, responsive to receiving an input to the component model. Various parameters of a gradient boosted decision tree are possible, as will be apparent to one skilled in the art, including a number of nodes per tree, number of layers of trees, number of splits, and/or number of final output nodes. In some embodiments, the parameters are tunable, for instance, as hyperparameters.

Gradient boosted decision trees generally learn by gradient descent. For example, in some implementations, the gradient descent is performed on a loss function (e.g., mean squared error). A variety of suitable differentiable loss function are possible and known in the art. At each iteration of gradient descent, the model is updated by adding one or more additional component models (e.g., "trees") to the model, where each respective additional component model attempts to refine or correct the output of one or more existing component models. In some embodiments, additional component models are added at all or a subset of the existing nodes such that the model aims to minimize the residual loss (e.g., based on a determination of one or more component models that contribute most heavily to loss). Moreover, in some embodiments, existing component models are frozen, and their parameters are not changed after each iteration of gradient descent. The gradient boosted decision tree as a whole is parameterized in that each existing component model (splits and nodes) includes parameters, and the output of the model is determined based on the aggregated outputs of all of the component models in a given sequence leading to the final node.

Referring to Block 232, in some embodiments, the first model comprises a neural network, a graph neural network, a logistic regression model, a boosted trees model, a random forest model, a decision tree model, a multinomial logistic regression model, a linear model, or a linear regression model. See, for example, the sections entitled "Definitions: Models," above, and "Second model (Classifier)," below.

Graph Neural Networks (GNNs) are an effective framework for representation learning of graphs. GNNs follow a neighborhood aggregation scheme, where the representation vector of a node is computed by recursively aggregating and transforming representation vectors of its neighboring nodes. After k iterations of aggregation, a node is represented by its transformed feature vector, which captures the structural information within the node's k-hop neighborhood. The representation of an entire graph can then be obtained through pooling, for example, by summing the representation vectors of all nodes in the graph. Input to a GNN includes molecular graphs, labeled graphs where the vertices and edges represent the atoms and bonds of the molecule, respectively. Graph neural networks and molecular graphs are further described, for example, in Xu et al., "How powerful are graph neural networks?" ICLR 2019, arXiv:1810.00826v3, which is hereby incorporated herein by reference in its entirety.

GNN variants for both node and graph classification tasks are known in the art. For example, in some embodiments, the first model is a graph convolutional neural network. Nonlimiting examples of graph convolutional neural networks are disclosed in Behler Parrinello, 2007, "Generalized Neural-Network Representation of High Dimensional Potential-Energy Surfaces," Physical Review Letters 98, 146401; Chmiela et al., 2017, "Machine learning of accurate energy-conserving molecular force fields," Science Advances 3(5):e1603015; Schütt et al., 2017, "SchNet: A continuous-filter convolutional neural network for modeling quantum interactions," Advances in Neural Information Processing Systems 30, pp. 992-1002; Feinberg et al., 2018, "PotentialNet for Molecular Property Prediction," ACS Cent. Sci. 4, 11, 1520-1530; and Stafford et al., "AtomNet PoseRanker: Enriching Ligand Pose Quality for Dynamic Proteins in Virtual High Throughput Screens," chemrxiv.org/engage/chemrxiv/article-details/614b905e39ef6a1c36268003, each of which is hereby incorporated by reference.

In some embodiments, the first model comprises a plurality of parameters (e.g., weights and/or hyperparameters). In some embodiments, the plurality of parameters for the model comprises at least 10, at least 50, at least 100, at least 500, at least 1000, at least 2000, at least 5000, at least 10,000, at least 20,000, at least 50,000, at least 100,000, at least 200,000, at least 500,000, at least 1 million, at least 2 million, at least 3 million, at least 4 million or at least 5 million parameters. In some embodiments, the plurality of parameters for the model comprises no more than 8 million, no more than 5 million, no more than 4 million, no more than 1 million, no more than 500,000, no more than 100,000, no more than 50,000, no more than 10,000, no more than 5000, no more than 1000, or no more than 500 parameters. In some embodiments, the plurality of parameters for the model comprises from 10 to 5000, from 500 to 10,000, from 10,000 to 500,000, from 20,000 to 1 million, or from 1 million to 5 million parameters. In some embodiments, the plurality of parameters for the model falls within another range starting no lower than 10 parameters and ending no higher than 8 million parameters.

In some embodiments, the training of the first model is further characterized by one or more hyperparameters (e.g., one or more values that may be tuned during training). In some embodiments, the hyperparameter values are tuned (e.g., adjusted) during training. In some embodiments, the hyperparameter values are determined based on the specific elements of a training dataset and/or one or more inputs (e.g., chemical structures, abundance values, and/or representations thereof). In some embodiments, the hyperparameter values are determined using experimental optimization. In some embodiments, the hyperparameter values are determined using a hyperparameter sweep. In some embodiments, the hyperparameter values are assigned based on prior template or default values.

In some embodiments, a respective hyperparameter of the one or more hyperparameters comprises a learning rate. In some embodiments, the learning rate is at least 0.0001, at least 0.0005, at least 0.001, at least 0.005, at least 0.01, at least 0.05, at least 0.1, at least 0.2, at least 0.3, at least 0.4, at least 0.5, at least 0.6, at least 0.7, at least 0.8, at least 0.9, or at least 1. In some embodiments, the learning rate is no more than 1, no more than 0.9, no more than 0.8, no more than 0.7, no more than 0.6, no more than 0.5, no more than 0.4, no more than 0.3, no more than 0.2, no more than 0.1 no more than 0.05, no more than 0.01, or less. In some embodiments, the learning rate is from 0.0001 to 0.01, from 0.001 to 0.5, from 0.001 to 0.01, from 0.005 to 0.8, or from 0.005 to 1. In some embodiments, the learning rate falls within another range starting no lower than 0.0001 and ending no higher than 1. In some embodiments, the one or more hyperparameters further include regularization strength (e.g., L2 weight penalty, dropout rate, etc.). For instance, in some embodiments, the model is trained using a regularization on a corresponding parameter (e.g., weight) of each hidden neuron in the plurality of hidden neurons. In some embodiments, the regularization includes an L1 or L2 penalty.

In some embodiments, the first model is trained using a loss function. In some embodiments, the loss function includes mean square error, flattened mean square error, quadratic loss, mean absolute error, mean bias error, hinge, multi-class support vector machine, and/or cross-entropy. In some embodiments, the loss function is a gradient descent algorithm and/or a minimization function.

In some embodiments, the first model is associated with one or more activation functions. In some embodiments, an activation function in the one or more activation functions is tanh, sigmoid, softmax, Gaussian, Boltzmann-weighted averaging, absolute value, linear, rectified linear unit (ReLU), bounded rectified linear, soft rectified linear, parameterized rectified linear, average, max, min, sign, square, square root, multiquadric, inverse quadratic, inverse multiquadric, polyharmonic spline, swish, mish, Gaussian error linear unit (GeLU), and/or thin plate spline.

In some embodiments, the first model is an ensemble model of a plurality of component models. For instance, in some embodiments, a respective predicted similarity is an aggregate and/or a measure of central tendency of an output of each component model in the plurality of component models. In some embodiments, the plurality of component models includes a logistic regression model, a boosted trees model, a random forest model, a decision tree model, a multinomial logistic regression model, a linear model, and/or a linear regression model.

In some embodiments, the ensemble model comprises at least 2, at least 3, at least 4, at least 5, at least 6, at least 7, at least 8, at least 9, at least 10, at least 20, at least 30, at least 40, at least 50, at least 60, at least 70, at least 80, at least 90, at least 100, at least 200, at least 300, at least 400, or at least 500 component models. In some embodiments, the ensemble model comprises no more than 500, no more than 400, no more than 300, no more than 200, or no more than 100 component models. In some embodiments, the ensemble model comprises no more than 100, no more than 50, no more than 40, no more than 30, or no more than 20 component models. In some embodiments, the ensemble model comprises between 1 and 50, between 2 and 20, between 5 and 50, between 10 and 80, between 5 and 15, between 3 and 30, between 10 and 500, between 2 and 100, or between 50 and 100 component models. In some embodiments, the ensemble model comprises another range of component models starting no lower than 2 component models and ending no higher than 500 component models.

Referring to Block 234, in some embodiments, the method further includes training the first model.

Referring to Block 236, in some embodiments, the first model comprises a plurality of weights and the training includes, for each respective training compound in a plurality of training compounds, performing a procedure including (i) obtaining a respective training fingerprint of a chemical structure of the respective training compound and (ii) responsive to inputting the respective fingerprint of the chemical structure of the respective training compound and the plurality of abundance values for each cellular constituent in the set of cellular constituents across the first plurality of cells into the first model, retrieving, as respective training output from the first model, a corresponding training predicted similarity between (a) a predicted perturbational effect of the respective training compound across the set of cellular constituents and (b) a measured cell-based perturbational effect of the reference chemical compound across the set of cellular constituents.

In some embodiments, the procedure further includes (iii) applying a respective difference to a loss function to obtain a respective output of the loss function, where the respective difference is between (a) the corresponding training predicted similarity from the first model and (b) a score from a second model that indicates whether, or to what degree, a predicted perturbational effect of the respective training compound across the set of cellular constituents matches a measured cell-based perturbational effect of the reference chemical compound across the set of cellular constituents. In some embodiments, the procedure further includes (iv) using the respective output of the loss function to adjust the first plurality of parameters.

In some embodiments, a training input to the first model includes any of the embodiments described above for test inputs, including chemical compounds, fingerprints, abundance values, and/or cellular constituents, or any substitutions, modifications, additions, deletions, and/or combinations that will be apparent to one skilled in the art (see, for example, the sections entitled "Compounds," "Cellular constituents," and "Abundance values," above). For example, in some embodiments, a training input to the first model is a concatenated vector that includes a vector representation of a fingerprint of the chemical structure of the respective training compound and a vector representation of the plurality of abundance values for each cellular constituent in the set of cellular constituents across the first plurality of cells.

In some embodiments, the corresponding training predicted similarity includes any of the embodiments described above for predicted similarities, or any substitutions, modifications, additions, deletions, and/or combinations that will be apparent to one skilled in the art (see, for example, the section entitled "Similarity predictions," above).

In some embodiments, the plurality of training compounds includes the reference compound. In some embodiments, the plurality of training compounds does not include the reference compound. In some embodiments, the plurality of training compounds includes one or more analogs (e.g., synthetic analogs) of the reference compound. In some embodiments, the plurality of training compounds includes one or more compounds used to train a second model (e.g., a transcriptional classifier). In some embodiments, the plurality of training compounds is all or a subset of a plurality of compounds used to train the second model (e.g., the transcriptional classifier). In some embodiments, the plurality of training compounds is different from the plurality of training compounds used to train the second model.

In some embodiments, the plurality of abundance values for each cellular constituent in the set of cellular constituents across the first plurality of cells includes any of the embodiments for abundance values described above (see, for example, the sections entitled "Cellular constituents" and "Abundance values," above). In some embodiments, for each respective training compound in the plurality of training compounds, the training procedure includes inputting, into the first model, the same plurality of abundance values for each cellular constituent in the set of cellular constituents across the first plurality of cells into the first model. In other words, in some such embodiments, the same control solution-specific abundance values are inputted into the first model during training, for each respective training compound in the plurality of training compounds.

In some embodiments, the training procedure includes, for a first respective training compound in the plurality of training compounds, inputting into the first model a first plurality of abundance values for each cellular constituent in the set of cellular constituents, and, for a second respective training compound in the plurality of training compounds, inputting into the first model a second plurality of abundance values for each cellular constituent in the set of cellular constituents. In other words, in some such embodiments, different sets of control solution-specific abundance values for different training compounds are used to train the first model. In some embodiments, the first plurality of abundance values is obtained from a first plurality of cells exposed to a first control solution free of the first training compound and the second plurality of abundance values is obtained from a second plurality of cells exposed to a second control solution free of the second training compound, where the first and second control solutions are different (e.g., the first model is trained on two or more different control solutions). In some embodiments, the first plurality of abundance values is obtained from a first plurality of cells exposed to the control solution free of the test chemical compound and the second plurality of abundance values is obtained from a second plurality of cells exposed to the control solution free of the test chemical compound, where the first and second plurality of cells are of different types (e.g., the first model is trained on different cell types).

In some embodiments, the score from the second model is a similarity score from a transcriptional classifier that provides a training label (e.g., a ground truth label) for the respective training compound for training the first model. In some such embodiments, the using the respective output of the loss function to adjust the first plurality of parameters includes updating the first plurality of parameters based on the output of the loss function applied to a difference between the predicted similarity of the first model and the training label.

Generally, training a model comprises updating a plurality of parameters (e.g., weights) for the model through backpropagation (e.g., gradient descent). First, a forward propagation is performed, in which input data is accepted into the model and an output is calculated based on an initial plurality of parameters (e.g., an activation function and/or a plurality of weights). In some embodiments, initial parameters (e.g., weights and/or hyperparameters) are randomly assigned (e.g., initialized) for an untrained or partially trained model. In some embodiments, parameters are transferred from a previously saved plurality of parameters or from a pre-trained model (e.g., by transfer learning).

A backward pass is then performed by calculating a loss (e.g., error) based on a difference between the model's output (e.g., a predicted similarity) and one or more labels (e.g., a ground truth label, such as a similarity score that indicates an association of the training compound with the reference compound). Parameters (e.g., weights) are then updated by adjusting the value based on the calculated loss, thereby training the model. In some embodiments, the parameters are updated in a manner where the model attempts to minimize the error (e.g., according to the loss function). In some embodiments, any one of a variety of backpropagation algorithms and/or methods are used to update the plurality of weights, as will be apparent to one skilled in the art.

In some embodiments, the loss function includes mean square error, quadratic loss, mean absolute error, mean bias error, hinge, multi-class support vector machine, and/or cross-entropy. In some embodiments, training an untrained or partially trained model comprises computing an error in accordance with a gradient descent algorithm and/or a minimization function. In some embodiments, training an untrained or partially trained model comprises computing a plurality of errors using a plurality of loss functions. In some embodiments, each loss function in a plurality of loss functions receives a same or a different weighting factor.

In some embodiments, the loss function is used to update one or more parameters (e.g., weights) in a model by adjusting the value of the one or more parameters by an amount proportional to the calculated loss, thereby training the model. In some embodiments, the amount by which the parameters are adjusted is metered by a learning rate hyperparameter that dictates the degree or severity to which parameters are updated (e.g., smaller or larger adjustments). Thus, in some embodiments, the training updates all or a subset of the plurality of parameters based on a learning rate. In some embodiments, the learning rate is a differential learning rate.

In some embodiments, training a model further uses a regularization on each respective parameter in the first plurality of parameters. For example, in some embodiments, a regularization is performed by adding a penalty to the loss function, where the penalty is proportional to the values of the parameters. Generally, regularization reduces the complexity of the model by adding a penalty to one or more parameters to decrease the importance of the respective parameters and/or any associated nodes. Such practice can result in a more generalized model and reduce overfitting of the data. In some embodiments, the regularization includes an L1 or L2 penalty. For example, in some preferred embodiments, the regularization includes an L2 penalty on lower and upper parameters. In some embodiments, the regularization comprises spatial regularization (e.g., determined based on a priori and/or experimental knowledge) or dropout regularization. In some embodiments, the regularization comprises penalties that are independently optimized.

In some embodiments, the training process is repeated for each training instance in a plurality of training instances.

In some embodiments, the plurality of training instances comprises at least 3, at least 4, at least 5, at least 6, at least 7, at least 8, at least 9, at least 10, at least 50, at least 100, at least 500, at least 1000, at least 2000, at least 3000, at least 4000, at least 5000, or at least 7500 training instances. In some embodiments, the plurality of training instances comprises no more than 10,000, no more than 5000, no more than 1000, no more than 500, no more than 100, or no more than 50 training instances. In some embodiments, the plurality of training instances comprises from 3 to 10, from 5 to 100, from 100 to 5000, or from 1000 to 10,000 training instances. In some embodiments, the plurality of training instances falls within another range starting no lower than 3 training instances and ending no higher than 10,000 training instances.

In some embodiments, the training comprises transfer learning. Transfer learning is further described, for example, in the Definitions section (see, "Untrained models," above).

In some embodiments, the training procedure further includes evaluating the error function for one or more training instances. In some such embodiments, the training procedure further includes adjusting the first plurality of parameters after performing at least 1, at least 2, at least 3, at least 4, at least 5, at least 6, at least 7, at least 8, at least 9, at least 10, at least 20, at least 30, at least 40, at least 50, at least 100, at least 500, at least 1000, at least 10,000, at least 50,000, at least 100,000, at least 200,000, at least 500,000, or at least 1 million evaluations of the error function. In some such embodiments, the training procedure further includes adjusting the first plurality of parameters at least 1, at least 2, at least 3, at least 4, at least 5, at least 6, at least 7, at least 8, at least 9, at least 10, at least 20, at least 30, at least 40, at least 50, at least 100, at least 500, at least 1000, at least 10,000, at least 50,000, at least 100,000, at least 200,000, at least 500,000, or at least 1 million times based on the at least 1, at least 2, at least 3, at least 4, at least 5, at least 6, at least 7, at least 8, at least 9, at least 10, at least 20, at least 30, at least 40, at least 50, at least 100, at least 500, at least 1000, at least 10,000, at least 50,000, at least 100,000, at least 200,000, at least 500,000, or at least 1 million evaluations of an error function.

In some embodiments, the training process is performed over one or more training instances until the model satisfies a threshold performance requirement. For example, in some embodiments, the threshold performance requirement is satisfied when an error calculated for the model, following an evaluation of an error function, satisfies an error threshold. In some embodiments, the error calculated by the error function satisfies an error threshold when the error is less than 20 percent, less than 18 percent, less than 15 percent, less than 10 percent, less than 5 percent, or less than 3 percent.

In some embodiments, the threshold performance requirement is satisfied when a validation metric calculated for the model satisfies a validation metric. In some embodiments, the validation metric is selected from the group consisting of number of true positives, number of false positives, number of true negatives, number of false positives, false positive rate, receiver operating characteristic area under the curve (ROC AUC), precision, recall (e.g., true positive rate), average precision, F1, and/or diagnostic odds.

Generally, ROC AUC provides an aggregate measure of performance of a model across a range of classification thresholds. Precision (P) is defined as the number of true positives ($T_p$) over the number of true positives plus the number of false positives ($F_p$): $P=T_p/(T_p+F_p)$. Recall (R) is defined as the number of true positives ($T_p$) over the number of true positives plus the number of false negatives ($F_n$): $R=T_p/(T_p+F_n)$. Average precision (AP) is defined as the weighted mean of precisions achieved at each threshold over the range of classification threshold, with the increase in recall from the previous threshold used as the weight. F1 score is defined as the harmonic mean of precision and recall. A diagnostic odds ratio (DOR) indicates the odds of a positive prediction for a ground-truth positive (e.g., a prediction of similarity for a "hit" compound) relative to the odds of a positive prediction for ground-truth negative (e.g., a prediction of similarity for a "non-hit" compound). For instance, a diagnostic odds ratio of 10 would indicate that a compound that is predicted by the second model to be similar is 10 times more likely to be a true "hit" than a "non-hit."

In some embodiments, the training procedure includes a training step using a first subset of training compounds in the plurality of training compounds and a validation step using a second subset of training compounds in the plurality of training compounds. In some embodiments, the second subset of training compounds is a held-out portion of the plurality of training compounds. In some embodiments, the first subset of training compounds is at least 50%, at least 60%, at least 70%, at least 80%, or at least 90% of the plurality of training compounds. In some embodiments, the first subset of training compounds is no more than 99%, no more than 90%, no more than 80%, no more than 70%, or no more than 60% of the plurality of training compounds. In some embodiments, the second subset of training compounds is at least 10%, at least 20%, at least 30%, at least 40%, or at least 50% of the plurality of training compounds. In some embodiments, the second subset of training compounds is no more than 60%, no more than 50%, no more than 40%, no more than 30%, or no more than 20% of the plurality of training compounds.

In some embodiments, the training procedure further includes K-fold cross-validation. In some such embodiments, a training dataset (e.g., for a plurality of training compounds) is divided into K bins. For each fold of training, one bin in the plurality of K bins is held out of the training dataset and the model is trained on the remaining K−1 bins. Performance of the model is then evaluated on the Kth bin that was removed from the training. This process is repeated K times, until each bin has been used once for validation. In some embodiments, K is 1, 2, 3, 4, 5, 6, 7, 8, 9, 10, 11, 12, 13, 14, 15, 16, 17, 18, 19, 20, or more than 20. In some embodiments, K is between 3 and 10. In some embodiments, training is performed using K-fold cross-validation with shuffling. In some such embodiments, the K-fold cross-validation is repeated by shuffling the training dataset and performing a second K-fold cross-validation training. The shuffling is performed so that each bin in the plurality of K bins in the second K-fold cross-validation is populated with a different (e.g., shuffled) subset of training data. In some such embodiments, the training comprises shuffling the training dataset 1, 2, 3, 4, 5, 6, 7, 8, 9, 10, or more than 10 times.

Second Model (Classifier).

Referring to Block 238, in some embodiments, the score from the second model is obtained by inputting a vector of abundance values into a second model, where each element in the vector of abundance values is a difference between (a) an abundance of a corresponding cellular constituent in the set of cellular constituents in a corresponding reference cell-based assay upon exposure to the respective training compound solvated in the control solution; and (b) an abundance of a corresponding cellular constituent in the set of cellular constituents in a corresponding reference cell-based assay upon exposure to the control solution free of the respective training compound.

In some embodiments, the vector of abundance values includes a corresponding set of elements, where each respective element in the set of elements corresponds to a respective cellular constituent in the set of cellular constituents.

In some embodiments, abundances of cellular constituents are obtained after exposure of one or more cells to a perturbagen. As defined above, in some embodiments, a perturbagen is any entity that induces a perturbation in one or more test cells, such as an exposure of the one or more test cells to one or more chemical compounds. In some embodiments, a perturbation includes a change in the expression or abundance level of one or more cellular constituents in the cell. See, for example, the section entitled "Definitions: Perturbations," above. In some embodiments, perturbagens include one or more test chemical compounds (e.g., solvated in a control solution), one or more reference compounds (e.g., solvated in a control solution), and/or one or more control solutions (e.g., free of any test chemical compound and/or reference compound).

Accordingly, in some embodiments, each element in the vector of abundance values is a difference between (a) an abundance of a corresponding cellular constituent in the set of cellular constituents in a corresponding reference cell-based assay upon exposure to a first perturbagen; and (b) an abundance of the corresponding cellular constituent in the set of cellular constituents in a corresponding reference cell-based assay upon exposure to a second perturbagen different from the first perturbagen.

As described above, in some embodiments, an abundance of a corresponding cellular constituent (e.g., upon exposure to a respective perturbagen) is obtained from a database. Examples of suitable databases include databases that provide results from drug screens, annotations, and/or general information such as compound targets and chemical properties of compounds, including, but not limited to, the Genomics of Drug Sensitivity in Cancer, the Cancer Therapeutics Response Portal, the Connectivity Map, PharmacoDB, the Base of Bioisosterically Exchangeable Replacements (BoBER), and/or DrugBank. Examples of suitable databases include databases that provide information on genes and gene products, perturbation-induced cellular constituent signatures, and/or pathway annotations, including, but not limited to, the NIH Gene Expression Omnibus (GEO), EBI ArrayExpress, NCBI, BLAST, EMBL-EBI, GenBank, Ensembl, the KEGG pathway database, the Library of Integrated Network-based Cellular Signatures (LINCS) L1000 dataset, the Reactome pathway database, and/or the Gene Ontology project.

In some embodiments, any of the methods and embodiments for obtaining abundance values disclosed herein are contemplated for use in obtaining the abundance values used for generating the vector of abundance values for the second model. See, for example, the sections entitled "Cellular constituents" and "Abundance values," above). In some embodiments, the (a) abundance of a corresponding cellular constituent in the set of cellular constituents in a corresponding reference cell-based assay upon exposure to a first perturbagen is obtained using the same or a different method as the (b) abundance of the corresponding cellular constituent in the set of cellular constituents in a corresponding reference cell-based assay upon exposure to the second perturbagen. For instance, in some embodiments, the (a) abundance of a corresponding cellular constituent in the set of cellular constituents in a corresponding reference cell-based assay upon exposure to the respective training compound solvated in the control solution is obtained using the same or a different method as the (b) abundance of a corresponding cellular constituent in the set of cellular constituents in a corresponding reference cell-based assay upon exposure to the control solution free of the respective training compound.

In some embodiments, an abundance for a corresponding cellular constituent is obtained using one or more reference cell-based assays, such as one or more single-cell assay experiments.

In some embodiments, the one or more reference cell-based assays include single-cell ribonucleic acid (RNA) sequencing (scRNA-seq). In some embodiments, the one or more reference cell-based assays include scTag-seq, single-cell assay for transposase-accessible chromatin using sequencing (scATAC-seq), CyTOF/SCoP, E-MS/Abseq, miRNA-seq, CITE-seq, and any combination thereof. In some embodiments, an abundance for a corresponding cellular constituent in the set of cellular constituents is determined by a colorimetric measurement, a fluorescence measurement, a luminescence measurement, a resonance energy transfer (FRET) measurement, a measurement of a protein-protein interaction, a measurement of a protein-polynucleotide interaction, a measurement of a protein-small molecule interaction. mass spectrometry, nuclear magnetic resonance, or a microarray measurement.

Various methods for performing cell-based assays, including applying perturbagens to test cells, isolating test cells, and preparing test cells for measurement of cellular constituents are contemplated for use in the present disclosure, as well as any substitutions, modifications, additions, deletions, and/or combinations that will be apparent to one skilled in the art. See, for example, the section entitled "Abundance values," above.

For instance, in some embodiments, an abundance for a corresponding cellular constituent in the set of cellular constituents is obtained by exposing a plurality of test cells to a perturbagen, such as a respective training compound and/or reference compound, in a therapeutically effective amount (e.g., a therapeutically effective concentration of the perturbagen).

In some embodiments, a respective training compound and/or reference compound is solvated in the control solution prior to exposure to the test cells. In some embodiments, a respective training compound and/or reference compound is solvated in a second solution, other than the control solution, prior to exposure to the test cells. In some embodiments, a respective training compound and/or reference compound is not applied to the test cells in combination with any other training compounds and/or reference compounds. In some embodiments, a respective training compound and/or reference compound is applied to the test cells in combination with one or more additional training compounds and/or reference compounds. In some embodiments, the method includes incubating a respective perturbagen with the test cells for a predefined period of time (e.g., 10 minutes, 30 minutes, 1 hour, 2 hours, 12 hours, 1 day, or more) prior to obtaining the plurality of abundance values.

In some embodiments, the cell-based assay is performed in replicate (e.g., for a plurality of droplets and/or a plurality of wells on an assay plate) for a respective perturbagen and/or a respective cellular constituent. For example, in some implementations, for a respective perturbagen, for each respective cellular constituent in the set of cellular constituents, the cell-based assay generates a corresponding plurality of abundance values, where each respective abundance value in the corresponding plurality of abundance values corresponds to a respective replicate (e.g., well and/or droplet) in a plurality of replicates. In some embodiments, as described above, the plurality of replicates is selected from a plurality of matched wells, a plurality of wells obtained from a common assay plate, a plurality of wells obtained from across a plurality of assay plates, a plurality of wells obtained from a same single-cell assay experiment, and/or a plurality of wells obtained from across a plurality of single-cell assay experiments (e.g., different experimental and/or technical conditions).

In some embodiments, the plurality of replicates includes a first set of wells in an assay plate, where each well in the first set of wells is matched to a corresponding matched well in the second set of wells; the first set of wells and the second set of wells are subjected to a common handling procedure; and one of the first set of wells and the second set of wells is exposed to a first perturbagen (e.g., a respective test chemical compound and/or reference compound solvated in a control solution) and the other of the first set of wells and the second set of wells is exposed to a second perturbagen (e.g., the control solution free of the respective test chemical compound and/or reference compound).

In some embodiments, abundance values are obtained as discussed in U.S. patent application Ser. No. 16/511,691 entitled "Methods of Analyzing Cells," filed Jul. 15, 2019, which is hereby incorporated herein by reference.

In some embodiments, the vector of abundance values for input into a second model is a V-score vector. V-score vectors are illustrated, for example, in FIG. 4B and further described in Example 1 below.

In some embodiments, the abundance of a corresponding cellular constituent in the set of cellular constituents in a corresponding reference cell-based assay upon exposure to a first perturbagen (e.g., the respective training compound solvated in the control solution) is a measure of central tendency over a plurality of abundance values for the corresponding cellular constituent over a corresponding plurality of replicates (e.g., cells, droplets, and/or wells). In some embodiments, the abundance of a corresponding cellular constituent in the set of cellular constituents in a corresponding reference cell-based assay upon exposure to a second perturbagen (e.g., a control solution free of the respective training compound) is a measure of central tendency over a plurality of abundance values for the corresponding cellular constituent over a corresponding plurality of replicates (e.g., cells, droplets, and/or wells). In some embodiments, the measure of central tendency is any measure of central tendency known in the art, including but not limited to a mean, median, mode, weighted mean, weighted median, weighted mode, arithmetic mean, midrange, midhinge, trimean, and/or Winsorized mean.

In some embodiments, for each respective element in the vector of abundance values, the respective difference between the (a) first abundance and the (b) second abundance is normalized. In some implementations, the normalization is performed using a measure of dispersion for one or more of the (a) first abundance and the (b) second abundance. Example measures of dispersion contemplated for use in the present disclosure include, but are not limited to, variance, standard deviation, and/or standard error. In some embodiments, the measure of dispersion is a combined measure of dispersion determined for the first abundance and the second abundance (e.g., a combined standard deviation).

In some embodiments, each respective element in the vector of abundance values is a Z-statistic for a respective cellular constituent in the set of cellular constituents.

In some embodiments, for each respective training compound in the plurality of training compounds, the Z-statistic for a respective cellular constituent is calculated using the following equation:

$$Z = \frac{(\bar{X}_1 - \bar{X}_2)}{\sqrt{\sigma^2_{\bar{X}_1} - \sigma^2_{\bar{X}_2}}}$$

where:

$\bar{X}_1$ is the mean abundance value of the cellular constituent averaged over a first subset of abundance values for the cellular constituent, obtained from a corresponding reference cell-based assay upon exposure to the respective training compound solvated in the control solution (e.g., the mean abundance value for the training compound);

$\bar{X}_2$ is the mean abundance value of the cellular constituent averaged over a second subset of abundance values for the cellular constituent, obtained from a corresponding reference cell-based assay upon exposure to the control solution free of the respective training compound (e.g., the mean abundance value for the control solution);

$\sigma_{X_1}^2$ is the standard deviation of the first subset of abundance values divided by the square root of the number of abundance values in the first subset (e.g., the population standard deviation for the training compound); and $\sigma_{X_2}^2$ is the standard deviation of the second subset of abundance values divided by the square root of the number of abundance values in the second subset (e.g., the population standard deviation for the control solution).

Consider an example workflow for obtaining a V-score vector of abundance values including a first element for a first gene A and a second element for a second gene B. A reference cell-based assay is performed to obtain abundance values for Gene A and Gene B, for example, where the reference cell-based assay includes a first subset of three wells exposed to Compound 1 solvated in DMSO and a second subset of three wells exposed to DMSO alone. The first subset of wells can be visualized as wells $C_1$, $C_2$, and $C_3$ ("Compound") and the second subset of wells can be visualized as wells $D_1$, $D_2$, and $D_3$ ("DMSO"), as shown below:

$$\begin{bmatrix} C_1 & C_2 & C_3 \\ D_1 & D_2 & D_3 \end{bmatrix}.$$

In the example embodiment, each of the wells exposed to Compound 1 are matched to a corresponding well exposed to DMSO alone, such that each well in the first subset of wells is subjected to the same laboratory handing and analysis procedures as a corresponding well in the second subset of wells. However, it will be understood that, in other embodiments, one or more abundance values obtained for the test compound and/or one or more abundance values obtained for the control solution are not limited to matched wells, wells on the same plate, wells from the same cell-based assay, or wells from the same timepoint.

A cell-based assay (e.g., single-cell ribonucleic acid sequencing (scRNA-seq)) is performed to obtain, from each respective well in the first and second subsets of wells, for each gene in the plurality of genes, a corresponding abundance value, as shown below:

Gene A abundance values:

$$\begin{bmatrix} C_{1A} & C_{2A} & C_{3A} \\ D_{1A} & D_{2A} & D_{3A} \end{bmatrix},$$

and
Gene B abundance values:

$$\begin{bmatrix} C_{1B} & C_{2B} & C_{3B} \\ D_{1B} & D_{2B} & D_{3B} \end{bmatrix}.$$

The V-score vector is then obtained such that each respective element in the vector is a corresponding Z-statistic for a respective gene in the plurality of genes.

The first element, corresponding to Gene A, is calculated as a Z-statistic between a first subset of the Gene A abundance values corresponding to Compound 1 (e.g., $C_{1A}$, $C_{2A}$, $C_{3A}$) and a second subset of the Gene A abundance values corresponding to DMSO (e.g., $D_{1A}$, $D_{2A}$, $D_{3A}$), in accordance with the above equation. The second element, corresponding to Gene B, is calculated as a Z-statistic between a first subset of the Gene B abundance values corresponding to Compound 1 (e.g., $C_{1B}$, $C_{2B}$, $C_{3B}$) and a second subset of the Gene B abundance values corresponding to DMSO (e.g., $D_{1B}$, $D_{2B}$, $D_{3B}$), in accordance with the above equation. Thus, the V-score vector has the form:

$$V = [Z_A \ Z_B].$$

Advantageously, Z-statistics as used in the present disclosure allow for the accurate accounting of the differences in expression between individual cells, for instance, by taking into account the standard deviations between individual measurements. More particularly, as described elsewhere herein, some embodiments of the present disclosure include obtaining abundance values for cellular constituents using assay experiments (e.g., single-cell assay experiments). Without being limited to any one theory of operation, such methods for measuring abundance values at the single-cell level would provide increased resolution and granularity to the observed perturbational effects (e.g., changes in expression). In contrast, bulk assays are at risk of smoothing out such fine details in the measured data, in some cases resulting in the loss of real perturbational effects due to the aggregation of multiple distinct signatures across a plurality of cellular constituents (e.g., transcriptional profiles) and/or artificially inflating the importance of perturbations that appear uniform in bulk but are in fact highly variable between individual cells.

In some embodiments, for each respective training compound in the plurality of training compounds, a fingerprint of the chemical structure of the respective training compound is not inputted into the second model to obtain the score (e.g., the similarity score used to train the first model).

As described elsewhere herein, in some embodiments, the set of cellular constituents is selected by determining, for each respective cellular constituent in a plurality of candidate cellular constituents, a preliminary correlation metric that is calculated using, for each respective training compound in the plurality of training compounds, a difference between (a) an abundance of the respective candidate cellular constituent in a corresponding reference cell-based assay upon exposure to the respective training compound solvated in the control solution; (b) an abundance of the corresponding cellular constituent in a corresponding reference cell-based assay upon exposure to the control solution free of the respective training compound; and (c) a score for the respective training compound that indicates whether, or to what degree, the respective training compound has a perturbational effect that matches a perturbational effect of the reference compound.

In some embodiments, the preliminary correlation metric is obtained using linear regression or logistic regression. In some embodiments, for each respective candidate cellular constituent in the plurality of candidate cellular constituents, the preliminary correlation metric is obtained by performing a logistic regression analysis across the plurality of training compounds to determine a regression coefficient that indicates a probability that a differential abundance value for the respective candidate cellular constituent, for a respective training compound in the plurality of training compounds, is indicative of a similarity between the respective training compound and a reference compound. In some embodiments, the preliminary correlation metric is a logistic regression coefficient.

In some embodiments, the set of cellular constituents is obtained by selecting, from the plurality of candidate cellular constituents, each respective candidate cellular constituent having a preliminary correlation metric that satisfies a first selection criterion. In some embodiments, the first selection criterion is membership in a set of candidate cellular constituents having the top N highest logistic regression coefficients, in the plurality of candidate cellular constituents. In other words, in some such embodiments, the set of cellular constituents was selected as the top N cellular constituents that were most predictive for similarity to the reference compound.

In some embodiments, N is at least 5, at least 10, at least 15, at least 20, at least 25, at least 30, at least 40, at least 50, at least 60, at least 70, at least 80, at least 90, at least 100, at least 200, at least 300, at least 400, at least 500, at least 600, at least 700, at least 800, at least 900, or at least 1000, at least 2000, at least 3000, at least 4000, at least 5000, at least 10,000, at least 30,000, at least 50,000, or more than 50,000. In some embodiments, N is no more than 100,000, no more than 50,000, no more than 10,000, no more than 5000, no more than 1000, no more than 500, no more than 200, no more than 100, no more than 50, or no more than 20. In some embodiments, N is from 5 to 20, from 20 to 50, from 50 to 100, from 100 to 200, from 200 to 500, from 500 to 1000, from 1000 to 5000, from 5000 to 10,000, or from 10,000 to 50,000. In some embodiments, N falls within another range starting no lower than 5 and ending no higher than 100,000.

As described above, regression coefficients are generally used to indicate how strongly a set of data supports a model (e.g., a logistic regression model), where a high regression coefficient for a particular cellular constituent indicates that the value of the similarity score is highly correlated with the abundance values of the cellular constituent, whereas a low regression coefficient for the respective cellular constituent indicates that the value of the similarity score is poorly correlated with the abundance values of the cellular constituent.

Consider a first example embodiment in which a set of 5 test chemical compounds are plotted according to the abundance values of a respective cellular constituent (e.g., Gene A) and a similarity score relative to a reference compound. Where there is little to no relationship between the abundance values of Gene A induced by each respective test chemical compound and its corresponding similarity score, the data points are positioned about the best fit line such that the residuals (e.g., distance between a data point and the best fit line) are high. In such an instance, a calculation of the preliminary correlation metric would indicate that the value of the similarity score is poorly correlated with the abundance values of Gene A.

Further, consider a second example embodiment in which the set of 5 test chemical compounds are plotted according to the abundance values of a respective cellular constituent (e.g., Gene A) and a similarity score relative to a reference compound. Where there is a strong relationship between the abundance values of Gene A induced by each respective test chemical compound and its corresponding similarity score, the data points are positioned about the best fit line such that the residuals (e.g., distance between a data point and the best fit line) are low or minimal. In such an instance, a calculation of the preliminary correlation metric would indicate that the value of the similarity score is strongly correlated with the abundance values of Gene A.

In some embodiments, the preliminary correlation metric is a goodness of fit, a coefficient of determination, and/or a coefficient of correlation. Alternatively or additionally, in some embodiments, the preliminary correlation metric is mean squared error and/or $R^2$.

In some embodiments, the preliminary correlation metric for a respective cellular constituent is determined using the same plurality of training compounds used to train the first model. In some embodiments, the preliminary correlation metric for a respective cellular constituent is determined using the same plurality of training compounds used to train the second model. In some embodiments, the preliminary correlation metric for a respective cellular constituent is determined using a different plurality of training compounds from the plurality of training compounds used to train the first and/or the second model.

Various methods of selecting cellular constituents for inclusion in the set of cellular constituents are contemplated for use in the present disclosure. For example, methods for selecting variables for multiple regression and/or multiple logistic regression are known in the art. Non-limiting examples of variable selection include forward selection and/or backward elimination. See, for example, McDonald, J. H. (2014). "Multiple regression." In *Handbook of Biological Statistics* (3rd ed.). Sparky House Publishing, Baltimore, Maryland, pp. 229-237, available on the Internet at biostathandbook.com/multipleregression.html; and McDonald, J. H. (2014). "Multiple logistic regression." In *Handbook of Biological Statistics* (3rd ed.). Sparky House Publishing, Baltimore, Maryland, pp. 247-253, available on the Internet at biostathandbook.com/multiplelogistic.html, each of which is hereby incorporated herein by reference in its entirety.

In some embodiments, the second model is a logistic regression model. In some embodiments, the first model is a multiple logistic regression model. In some embodiments, the second model is an algorithm for gradient boosting on decision trees. In some embodiments, the second model is CatBoost or XGBoost. In some embodiments, the second model comprises a neural network model, a graph neural network model, a logistic regression model, a boosted trees model, a random forest model, a decision tree model, a multinomial logistic regression model, a linear model, or a linear regression model. Any suitable model for generating a score that indicates whether, or to what degree, a predicted perturbational effect of the respective training compound across the set of cellular constituents matches a measured cell-based perturbational effect of the reference chemical compound across the set of cellular constituents is contemplated for use in the present disclosure, as will be apparent to one skilled in the art. See, for example, the sections entitled "Definitions: Models" and "First model (Structure Behavior Relationship)," above).

In some embodiments, the score generated by the second model is a probability that falls between 0 and 1. In some embodiments, a score closer to "1" (e.g., 0.89, 0.90, 0.91, 0.92, etc.) indicates association between a training compound and a reference compound, and a score closer to "0" (e.g., 0.01, 0.02, 0.03, 0.04, etc.) indicates no association between the training compound and the reference compound. In some embodiments, a score closer to "1" (e.g., 0.89, 0.90, 0.91, 0.92, etc.) indicates no association between a training compound and a reference compound, and a score closer to "0" (e.g., 0.01, 0.02, 0.03, 0.04, etc.) indicates association between the training compound and the reference compound.

In some embodiments, when the score generated by the second model achieves a second threshold similarity, the respective training compound is associated with the reference compound. In some embodiments, the second threshold similarity includes any embodiments or methods for obtaining a threshold similarity disclosed herein, or any substitutions, modifications, additions, deletions, and/or combinations that will be apparent to one skilled in the art (see, for example, the section entitled "Similarity predictions," above). For example, in some implementations, the second threshold similarity is 0.15. An example schematic showing determination of whether a predicted perturbational effect of a respective training compound matches a measured cell-based perturbational effect of a reference chemical compound (e.g., transcriptional classification scores for hits and non-hits based on V-score vectors) are illustrated, for example, in FIG. 4D.

In some embodiments, the second model is trained using the same or different plurality of training compounds used to train the first model. In some embodiments, the second model is trained using all or a portion of the plurality of training compounds used to train the first model. In some embodiments, the second model is trained simultaneously with the first model. In some embodiments, the second model is trained separately from the first model. In some embodiments, the second model is trained by gradient descent.

In some implementations, the second model is trained using any of the methods for model training disclosed herein, or any substitutions, modifications, additions, deletions, and/or combinations that will be apparent to one skilled in the art (see, for example, the section entitled "First model (Structure Behavior Relationship)," above).

Example Applications

As described above, in some embodiments, the reference chemical compound induces a corresponding perturbational effect, such as a cell behavior or phenotype that is associated with a condition. Various example applications for test chemical compounds associated with the reference compound will now be described.

Referring to Block 240, in some embodiments, the reference compound alleviates a condition in a subject, and the method further comprises administering the test chemical compound to the subject as a treatment to alleviate the condition in the subject when the predicted similarity achieves the threshold similarity. Referring to Block 242, in some embodiments, the treatment comprises a composition comprising the test chemical compound and one or more excipient and/or one or more pharmaceutically acceptable carrier and/or one or more diluent.

Referring to Block 244, in some embodiments, the condition is inflammation or pain. Referring to Block 246, in some embodiments, the condition is a disease. Referring to Block 248, in some embodiments, the condition is a cancer, hematologic disorder, autoimmune disease, inflammatory disease, immunological disorder, metabolic disorder, neurological disorder, genetic disorder, psychiatric disorder, gastroenterological disorder, renal disorder, cardiovascular disorder, dermatological disorder, respiratory disorder, viral infection, or other disease or disorder.

In some embodiments, the method 200 further includes evaluating a plurality of test chemical compounds for association with the reference compound. In some such embodiments, each test chemical compound in a plurality of test chemical compounds is used to perform the method 200. Thus, if there are 100 test chemical compounds and one reference compound, in some such embodiments, method 200 is performed 100 times, where each instance in the 100 instances is for a different one of the test chemical compounds.

Moreover, in some embodiments, the method 200 further includes evaluating a plurality of test chemical compounds for association with a plurality of reference compounds. In some such embodiments, for each respective reference compound in the plurality of reference compounds, each respective each test chemical compound in the plurality of test chemical compounds is used to perform the method 200. Thus, if there are 100 test chemical compounds and two reference compounds, in some such embodiments, method 200 is performed 200 times, where each instance in the 200 instances is for a different one of the test chemical compounds against either the first or the second reference compound.

Any one or more of the embodiments disclosed here for performing a first instance of a method of associating a test chemical compound with a reference compound, including conditions, test chemical compounds, reference chemical compounds, cellular conditions, abundance values, similarity predictions, first model, second model, model training, and/or selection of cellular constituents are similarly contemplated for a second, third, fourth, or any subsequent instance of the method, or any substitutions, modifications, additions, deletions, and/or combinations that will be apparent to one skilled in the art.

In some embodiments, the method further includes ranking the plurality of test chemical compounds based on the predicted similarity of each respective test chemical compound in the plurality of test chemical compounds.

In some embodiments, the method further includes determining a probability that one or more test chemical compounds in the plurality of test chemical compounds are associated with the reference compound. In some embodiments, the method further includes determining a probability that no test chemical compounds in the plurality of test chemical compounds are associated with the reference compound. In some embodiments, the method further includes selecting a number of test chemical compounds in the plurality of test chemical compounds for further validation.

In some embodiments, the method further includes, when the test chemical compound is associated with the reference compound, performing a validation of the perturbational effect of the test chemical compound using a cell-based assay for a biological sample comprising one or more test cells.

In some embodiments, the method further includes, when the test chemical compound is associated with the reference compound, determining one or more molecular properties of the test chemical compounds.

For instance, in some implementations, the sub-structures within the test chemical compounds that cause such compounds to associate with the reference compound are identified using one or more of substructure mining, maximum common substructure (MCS) analysis, SMARTS, Frequent Subgraph Mining, and/or graph and chemical mining. Examples of substructure mining include, but are not limited to, MOSS (Borgetl and Meinl, 2006, "Full Perfect Extension Pruning for Frequent Graph Mining," Proc. Workshop on Mining Complex Data (MCD 2006 at ICDM 2006, Hong Kong, China, IEEE Press, Piscataway, NJ, USA, which is hereby incorporated by reference, and MOFA (Meinl and Worlein, 2006 "Mining Molecular Datasets on Symmetric Processor Systems," International conference on Systems, man and Cybernetics 2, pp. 1269-1274, which is hereby incorporated by reference). Examples of MCS analysis include, but are not limited to LIBMCS (Chemaxon, Library MCS, 2008), MCSS (OEChem TK version 2.0.0, OpenEye Scientific Software, Santa Fe, NM, available on the Internet at eyesopen.com), and CncMCS (available on the Internet at chemnavigator.com/cnc/products/downloads.asp). An Example of SMART analysis is the CDK Descriptor GUI. An example of Frequent Subgraph Mining is ParMol (Uni Erlangen). An example of graph and chemical mining is PAFI/AFGen (Karypis Lab UMN).

Further Embodiments

Another aspect of the present disclosure provides a method of associating a test chemical compound with a reference compound, the method comprising (A) obtaining a fingerprint of a chemical structure of the test chemical compound, and (B) responsive to inputting the fingerprint of the chemical structure of the test chemical compound into a first model, retrieving, as output from the first model, a predicted perturbational effect of the test chemical compound.

In some embodiments, the first model comprises a first plurality of parameters, further comprising training the first model by a procedure comprising: for each respective training compound in a plurality of training compounds: (i) obtaining a respective training fingerprint of a chemical structure of the respective training compound; (ii) responsive to inputting the respective fingerprint of the chemical structure of the respective training compound into the first model, retrieving, as respective training output from the first model, a corresponding training predicted perturbational effect of the respective training compound; (iii) applying a respective difference to a loss function to obtain a respective output of the loss function, wherein the respective difference is between (a) the corresponding training predicted perturbational effect of the respective training compound from the first model and (b) a reference perturbational effect of the respective training compound, wherein the reference perturbational effect of the respective training compound is (i) a measured reference perturbational effect obtained from a reference cell-based assay, or (ii) a predicted reference perturbational effect predicted by a second model; and (iv) using the respective output of the loss function to adjust the first plurality of parameters.

In some embodiments, for each respective training compound in at least a first subset of the plurality of training compounds, the reference perturbational effect is a predicted reference perturbational effect predicted by the second model.

In some embodiments, the predicted reference perturbational effect from the second model is obtained by inputting a vector of abundance values into the second model, wherein each element in the vector of abundance values is a difference between: (a) an abundance of a corresponding cellular constituent in a set of cellular constituents in a corresponding reference cell-based assay upon exposure to the respective training compound solvated in a control solution; and (b) an abundance of a corresponding cellular constituent in the set of cellular constituents in a corresponding reference cell-based assay upon exposure to the control solution free of the respective training compound.

In some embodiments, the second model comprises a second plurality of parameters, further comprising training the second model by a procedure comprising: for each respective pre-training compound in a plurality of pre-training compounds: (i) obtaining a vector of abundance values, each element in the vector of abundance values a difference between: (a) an abundance of a corresponding cellular constituent in a set of cellular constituents in a corresponding reference cell-based assay upon exposure to the respective training compound solvated in a control solution, and (b) an abundance of a corresponding cellular constituent in the set of cellular constituents in a corresponding reference cell-based assay upon exposure to the control solution free of the respective training compound. In some embodiments, the procedure further includes, for each respective pre-training compound in a plurality of pre-training compounds: (ii) responsive to inputting the vector of abundance values of the pre-training compound into the second model, retrieving, as respective pre-training output from the second model, a corresponding pre-training predicted perturbational effect of the respective pre-training compound. In some embodiments, the procedure further includes, for each respective pre-training compound in a plurality of pre-training compounds: (iii) applying a respective difference to a loss function to obtain a respective output of the loss function, wherein the respective difference is between (a) the corresponding pre-training predicted perturbational effect of the respective pre-training compound from the second model and (b) a reference perturbational effect of the respective pre-training compound, wherein the reference perturbational effect of the respective training compound is a measured cell-based perturbational effect of the respective pre-training compound obtained from a reference cell-based assay. In some embodiments, the procedure further includes, for each respective pre-training compound in a plurality of pre-training compounds: (iv) using the respective output of the loss function to adjust the second plurality of parameters.

In some embodiments, for each respective training compound in at least a second subset of the plurality of training compounds, the reference perturbational effect is a measured reference perturbational effect obtained from a reference cell-based assay.

In some embodiments, each respective training compound in the second subset of the plurality of training compounds is used to train the second model.

In some embodiments, the method further includes determining a similarity between (i) the predicted perturbational effect of the test chemical compound and (ii) a measured cell-based perturbational effect of the reference compound.

In some embodiments, the retrieving the predicted perturbational effect of the test chemical compound further comprises: inputting, to the first model, a plurality of abundance values for each cellular constituent in a set of cellular constituents obtained from one or more reference assay experiments across a first plurality of cells that have been exposed to a control solution free of the test chemical compound.

In some embodiments, the control solution is a polar aprotic solvent or a mixture of polar aprotic solvents. In some embodiments, the control solution is dimethyl sulfoxide, N,N-dimethylformamide, acetonitrile, acetone or a mixture thereof. In some embodiments, each respective abundance value in the plurality of abundance values is a measure of central tendency of the abundance value of the corresponding cellular constituent across the first plurality of cells in the one or more reference assay experiments. In some embodiments, the plurality of abundance values are obtained in the one or more reference assay experiments by single-cell ribonucleic acid (RNA) sequencing (scRNA-seq). In some embodiments, each cellular constituent in the set of cellular constituents uniquely maps to a different gene. In some embodiments, each cellular constituent in the plurality of cellular constituents is a particular gene, a particular mRNA associated with a gene, a carbohydrate, a lipid, an epigenetic feature, a metabolite, an antibody, a peptide a protein, or a post-translational modification of a protein. In some embodiments, the set of cellular constituents comprises 10 or more cellular constituents, 20 or more cellular constituents, 30 or more cellular constituents, 40 or more cellular constituents, or 50 or more cellular constituents. In some embodiments, the set of cellular constituents consists of between 10 and 200 cellular constituents. In some embodiments, the first plurality of cells are cells from an organ, cells from a tissue, a plurality of stem cells, a plurality of primary human cells, cells from umbilical cord blood, cells from peripheral blood, bone marrow cells, cells from a solid tissue, or a plurality of differentiated cells. In some embodiments, the plurality of abundance values are determined by a colorimetric measurement, a fluorescence measurement, a luminescence measurement, a resonance energy transfer (FRET) measurement, a measurement of a protein-protein interaction, a measurement of a protein-polynucleotide interaction, a measurement of a protein-small molecule interaction. mass spectrometry, nuclear magnetic resonance, or a microarray measurement.

In some embodiments, the first model is a logistic regression model.

In some embodiments, the first model is an algorithm for gradient boosting on decision trees.

In some embodiments, the first model is CatBoost or XGBoost.

In some embodiments, the first model comprises a neural network, a graph neural network, a logistic regression model, a boosted trees model, a random forest model, a decision tree model, a multinomial logistic regression model, a linear model, or a linear regression model.

In some embodiments, the method further includes calculating the fingerprint of the chemical structure of the test chemical compound from a string representation of the chemical structure. In some embodiments, the string representation is in a SMARTS (SMARTS—A Language for Describing Molecular Patterns," 2022 on the Internet at daylight.com/dayhtml/doc/theory/theory.smarts.html (accessed December 2020), DeepSMILES (O'Boyle and Dalke, 2018, "DeepSMILES: an adaptation of SMILES for use in machine-learning of chemical structures," Preprint at ChemRxiv. https://doi.org/10.26434/chemrxiv.7097960.v1.), self-referencing embedded string (SELFIES) (Krenn et al., 2022, "SELFIES and the future of molecular string representations," Patterns 3(10), pp. 1-27), or simplified molecular-input line-entry system (SMILES) format. Molecular fingerprinting using SMILES strings is described, for example, in Honda et al., 2019, "SMILES Transformer: Pre-trained Molecular Fingerprint for Low Data Drug Discovery," arXiv:1911.04738, which is hereby incorporated herein by reference in its entirety.

Another approach to transforming chemical structures into machine-learning readable formats includes determining a graph-based molecular fingerprint. In graph-based molecular fingerprinting, the original molecular structure is represented by a graph, in which nodes represent individual atoms and edges represent bonds between atoms. Graph-based approaches provide several advantages, including the ability to efficiently encode multiple substructures with lower size requirements and thus lower computational burden, as well as the ability to encode indications of structural similarity between fingerprints. Graph-based fingerprinting is further described, for instance, in Duvenaud et al., 2015, "Convolutional networks on graphs for learning molecular fingerprints," NeurIPS, 2224-2232, which is hereby incorporated herein by reference in its entirety. In some embodiments, the fingerprint is generated from a graph convolutional network. In some embodiments, the fingerprint is generated from a spatial graph convolutional network, such as a graph attention network (GAT), a graph isomorphism network (GIN), or a graph substructure index-based approximate graph (SAGA). In some embodiments, the fingerprint is generated from a spectral graph convolutional network, such as a spectral graph convolution using Chebyshev polynomial filtering.

In some embodiments, the method further includes generating the fingerprint of the chemical structure of the test chemical compound from a chemical structure of the test chemical compound using Daylight, BCI, ECFP4, EcFC, MDL, APFP, TTFP, UNITY 2D fingerprint, RNNS2S, or GraphConv.

In some embodiments, the method further includes generating the fingerprint of the chemical structure of the test chemical compound from a chemical structure of the test chemical compound by inputting a string representation of the test chemical compound into each featurizer in a set of featurizers to obtain the fingerprint. In some embodiments, the set of featurizers consists of 1, 2, 3, or 4 featurizers in Table 4.

In some embodiments, the fingerprint of the first compound 2108-1 is a concatenation of an output of each feature in the set of features in such embodiments. For instance, in an embodiment in which all four featurizers of Table 4 are used, the fingerprint of the test chemical compound consists of 300+2000+211+167 or 2678 features.

In some embodiments, the set of featurizers consists of between 2 and 40 featurizers in Table 5. In some embodiments, the feature representation of the test chemical compound is a concatenation of an output of each feature in the set of featurizers.

In some embodiments, a featurizer in the set of featurizers makes use of a deep graph convolutional neural network (e.g., Zhang et al, "An End-to-End Deep Learning Architecture for Graph Classification," The Thirty-Second AAAI Conference on Artificial Intelligence), GraphSage (e.g., Hamilton et al., 2017, "Inductive Representation Learning on Large Graphs," arXiv:1706.02216 [cs.SI]), a graph isomorphism network (e.g., Hu et al., 2018, "How Powerful are Graph Neural Networks," cs>arXiv:1810.00826, an edge-conditioned convolutional neural network (ECC) (e.g., Simonovsky and Komodakis, 2017, "Dynamic Edge-Conditioned Filters in Convolutional Neural Networks on Graphs," arXiv:1704.02901 [cs.CV]), a differentiable graph encoder such as DiffPool (e.g., Ying et al., 2018, "Hierarchical Graph Representation Learning with Differentiable Pooling" arXiv:1806.08804 [cs.LG]), a message-passing graph neural network such as MPNN (Gilmer et al., 2017, "Neural Message Passing for Quantum Chemistry," arXiv: 1704.01212 [cs.LG]) or D-MPNN (Yang et al., 2019, "Analyzing Learned Molecular Representations for Property Prediction" J. Chem. Inf. Model. 59(8), pp. 3370-3388), or a graph neural network such as CMPNN (Song et al., "Communicative Representation Learning on Attributed Molecular Graphs," Proceedings of the Twenty-Ninth International Joint Conference on Artificial Intelligence (IJCAI-20)). See also Rao et al., 2021, "MolRep:A Deep Representation Learning Library for Molecular Property Prediction," doi.org/10.1101/2021.01.13.426489; posted Jan. 16, 2021. T; Rao et al., "Quantitative Evaluation of Explainable Graph Neural Networks for Molecular Property Prediction," arXiv preprint arXiv:2107.04119; and github.com/biomed-AI/MolRep.

In some embodiments, the fingerprint of the chemical structure of the test chemical compound is obtained as a vector representation (e.g., as a string). Any suitable method for obtaining vector representations of chemical structure fingerprints, including the methods and embodiments disclosed above, are contemplated for use in the present disclosure.

In some embodiments, the fingerprint of the chemical structure of the test chemical compound is concatenated to a vector that includes, for each cellular constituent in a set of cellular constituents, a plurality of abundance values obtained from one or more reference assay experiments across a first plurality of cells that have been exposed to a control solution free of the test chemical compound.

In some embodiments, the test chemical compound is a first organic compound having a molecular weight of less than 2000 Daltons, and the reference chemical compound is a second organic compound having a molecular weight of less than 2000 Daltons.

In some embodiments, the test chemical compound satisfies any two or more rules, any three or more rules, or all four rules of the Lipinski's rule of Five: (i) not more than five hydrogen bond donors, (ii) not more than ten hydrogen bond acceptors, (iii) a molecular weight under 500 Daltons, and (iv) a Log P under 5.

In some embodiments, the reference compound alleviates a condition in a subject, and the method further comprises: administering the test chemical compound to the subject as a treatment to alleviate the condition in the subject when a similarity between (i) the predicted perturbational effect of the test chemical compound and (ii) a measured cell-based perturbational effect of the reference chemical compound achieves a threshold similarity.

In some embodiments, the treatment comprises a composition comprising the test chemical compound and one or more excipient and/or one or more pharmaceutically acceptable carrier and/or one or more diluent.

In some embodiments, the condition is inflammation or pain. In some embodiments, the condition is a disease. In some embodiments, the condition is a cancer, hematologic disorder, autoimmune disease, inflammatory disease, immunological disorder, metabolic disorder, neurological disorder, genetic disorder, psychiatric disorder, gastroenterological disorder, renal disorder, cardiovascular disorder, dermatological disorder, respiratory disorder, viral infection, or other disease or disorder.

In some embodiments, the second model is a logistic regression model or a random forest model.

In some embodiments, the predicted perturbational effect is selected from the group consisting of an IC50, a measure of differential gene expression, a log fold change, a ddCq value, a measure of apoptosis, a staining intensity, a textural pattern, a size of a cell or a cellular structure thereof, a shape of a cell or a cellular structure thereof, and any correlation or adjacency relationship thereof.

In some embodiments, the perturbational effect comprises any biological, biochemical, chemical, or physiological readout that is measurable by a cell-based assay, as will be apparent to one skilled in the art. For instance, in some embodiments, the perturbational effect is one that is measurable by imaging cytometry, electrophysiology, proteomic imaging, and/or 3D imaging.

In some embodiments, imaging cytometry is used to obtain the perturbational effect for one or more cells. Imaging flow cytometry combines the statistical power and fluorescence sensitivity of standard flow cytometry with the spatial resolution and quantitative morphology of digital microscopy. See, for example, Basiji et al., 2007, "Cellular Image Analysis and Imaging by Flow Cytometry," Clinics in Laboratory Medicine 27, 653-670, which is hereby incorporated by reference.

In some embodiments, electrophysiology is used to obtain the perturbational effect for one or more cells. See, for example, Dunlop et al., 2008, "High-throughput electrophysiology: an emerging paradigm for ion-channel screening and physiology," Nature Reviews Drug Discovery 7, 358-368, which is hereby incorporated by reference.

In some embodiments, proteomic imaging/3D imaging is used to obtain the perturbational effect for one or more cells. See for example, United States Patent Publication No. 20170276686 A1, entitled "Single Molecule Peptide Sequencing," which is hereby incorporated by reference. Such methods can be used to large-scale sequencing of single peptides in a mixture from an entity, or a plurality of entities at the single molecule level.

In some embodiments, a perturbational effect is measured for one or more cells after such cells have been exposed to a perturbation (e.g., a compound, an analog compound, an siRNA, etc.), such as by using a panel of fluorescent stains that emit at different wavelengths. Non-limiting example fluorescent stains suitable for use in the present disclosure include, for instance, Concanavalin A/Alexa Fluor 488 conjugate (Invitrogen, cat. no. C11252), Hoechst 33342 (Invitrogen, cat. no. H3570), SYTO 14 green fluorescent nucleic acid stain (Invitrogen, cat. no. S7576), Phalloidin/Alexa Fluor 568 conjugate (Invitrogen, cat. no. A12380), and MitoTracker Deep Red (Invitrogen, cat. no. M22426). In some embodiments, perturbational effects include staining intensities, textural patterns, size, and shape of the labeled cellular structures, as well as correlations between stains across channels, and adjacency relationships between cells and among intracellular structures. In some embodiments, two, three, four, five, six, seven, eight, nine, ten, or more than 10 fluorescent stains, imaged in two, three, four, five, six, seven, or eight channels, is used to measure perturbational effects, including but not limited to measurements obtained within different cellular components or compartments within such entities. In some embodiments, perturbational effects are measured from single cells. In some embodiments, perturbational effects are measured from a compartment or a component (e.g., nucleus, endoplasmic reticulum, nucleoli, cytoplasmic RNA, F-actin cytoskeleton, Golgi, plasma membrane, mitochondria) of a single cell or a plurality of cells. In some embodiments, each channel comprises (i) an excitation wavelength range and (ii) a filter wavelength range in order to capture the emission of a particular dye from among the set of dyes the cell or cells has been exposed to prior to measurement. Non-limiting example dyes that may be invoked and the type of cells or components thereof that may be measured for perturbational effects for five suitable channels are provided in Table 3 below, which is adapted from Table 1 of Bray et al., 2016, "Cell Painting, a high-content image-based assay for morphological profiling using multiplexed fluorescent dyes," Nature Protocols, 11, p. 1757-1774, which is hereby incorporated by reference.

TABLE 3 example channels used for measuring features

| Channel | Dye | Filter (excitation; nm) | Filter (emission; nm) | Entity component or compartment |
|---|---|---|---|---|
| 1 | Hoechst 33342 | 387/11 | 417-477 | Nucleus |
| 2 | Concanavalin A/Alexa Fluor 488 conjugate | 472/30$_a$ | 503-538$_a$ | Endoplasmic reticulum |
| 3 | SYTO 14 green fluorescent nucleic acid stain | 531/40 | 573-613 | Nucleoli, cytoplasmic RNA$_b$ |
| 4 | Phalloidin/Alexa Fluor 568 conjugate, wheat-germ agglutinin/Alexa Fluor 555 conjugate | 562/40 | 622-662$_c$ | F-actin cytoskeleton, Golgi, plasma membrane |
| 5 | MitoTracker Deep Red | 628/40 | 672-712 | Mitochondria |

In some embodiments, the perturbational effect is selected from the group consisting of area, shape, number, volume, capacity, center X, center Y, compactness, eccentricity, Euler number, extent, form factor, major axis length, max Feret diameter, maximum radius, mean radius, median radius, min Feret diameter, minor axis length, orientation, perimeter, solidity, Zernike, correlation, granularity, intensity, location, radial distribution, texture, neighbors, variance, entropy, displacement, contrast, and/or any measure of central tendency, measure of dispersion, or confidence thereof.

Alternatively or additionally, in some embodiments, the perturbational effect is associated with and/or obtained from a cell or a component thereof, including but not limited to cell body, nuclear components, and/or cytoplasmic components (e.g., endoplasmic reticulum, DNA, mitochondria, ADP-glucose pyrophosphorylase).

Alternatively or additionally, in some embodiments, the perturbational effect is selected from any of the image features described in Bray et al., 2016, "Cell Painting, a high-content image-based assay for morphological profiling using multiplexed fluorescent dyes," Nature Protocols, 11, p. 1757-1774, which is hereby incorporated by reference.

As noted above, in some embodiments, the process of measuring perturbational effects using cell-based assays for each test compound in a library of test compounds is laborious, costly, resource-heavy, and time-consuming. Consider, for example, the case where thousands, millions, hundreds of millions, or more test compounds are candidates for drug development and discovery. Determining which of the many candidate test compounds will induce the target cellular behavior or readout would be impractical or even impossible.

Additionally, the identification of target molecules, such as binding partners, for such a large number of candidate test compounds can be challenging, and presents a bottleneck for the drug discovery process. Thus, in some implementations, the systems and methods disclosed herein advantageously facilitate the optimization of structures towards target cell behaviors (e.g., perturbational effects) without a cellular target by using target-agnostic in-silico screening. In other words, in some implementations, systems and methods disclosed herein are used to directly predict the target activity (e.g., cell behaviors or perturbational effects) of candidate test chemical compounds. In some embodiments, this prediction occurs using only the chemical structures, and/or, optionally, target-agnostic perturbation data such as control or baseline transcriptional data obtained from cells in the absence of test compound exposure.

Advantageously, the systems and methods disclosed herein allow for the direct prediction of perturbational effects (e.g., cell behaviors) that are both target-agnostic (e.g., that bypass the need to identify molecular targets for the test chemical compounds) and can be performed with a limited set of experimentally measured data (e.g., that bypass the need for laborious, expensive, and time-consuming in vitro experimentation). In some implementations, this is accomplished by using an intermediate model (e.g., a transcriptional model, or the second model) to extrapolate predictions of perturbational effects for compounds based on transcriptional signatures (e.g., vectors of abundance values) for training compounds, and using the extrapolated predictions to train a primary model (e.g., a structure model, or the first model) to predict the same based on chemical structure.

Figure 10A:
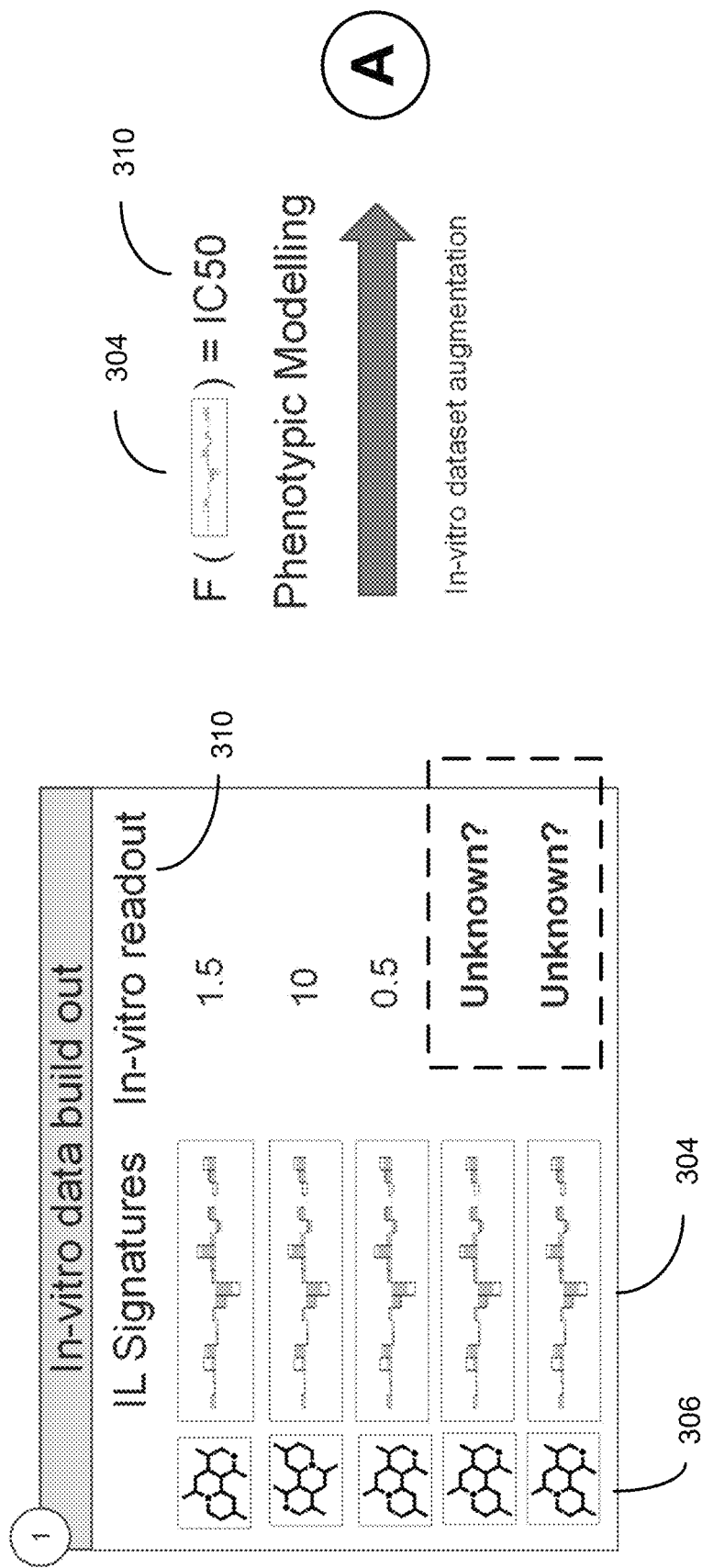
FIGS. 10A, 10B, 10C, and 10D collectively illustrate an example schematic for associating a test chemical compound with a reference compound, in accordance with an embodiment of the present disclosure.
Figure 10B:
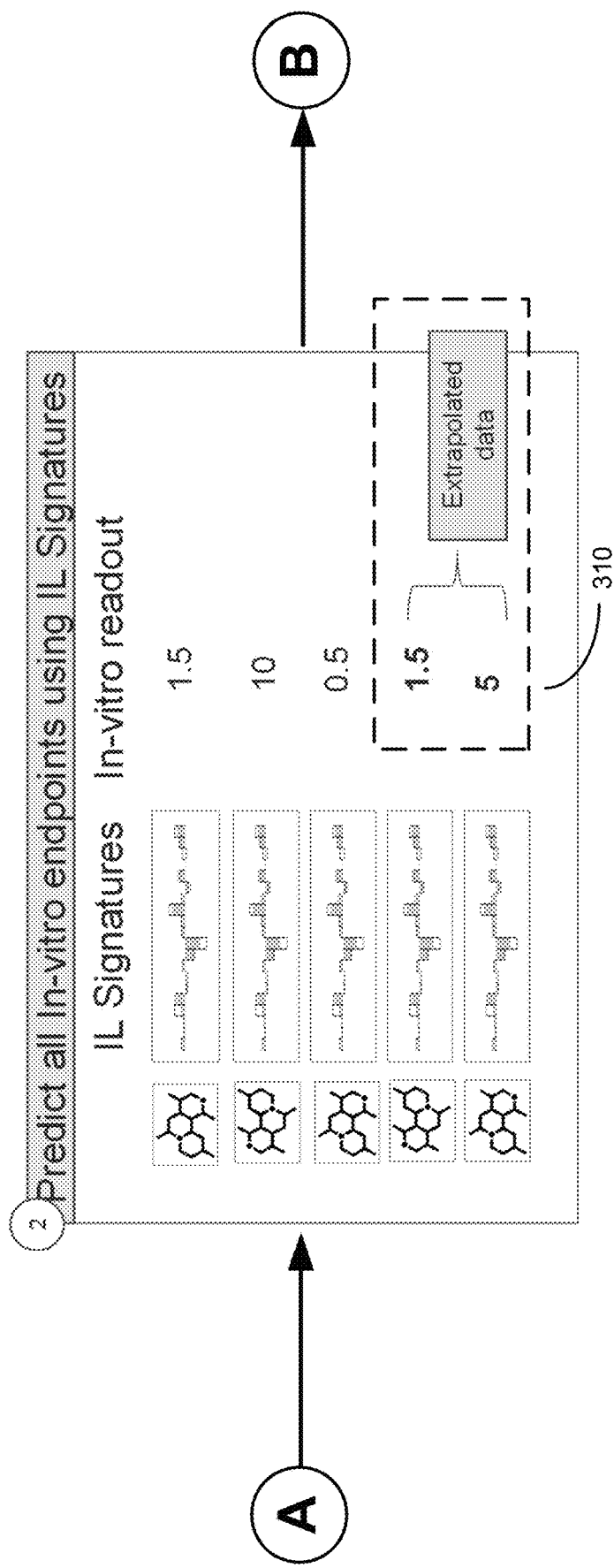
Figure 10C:
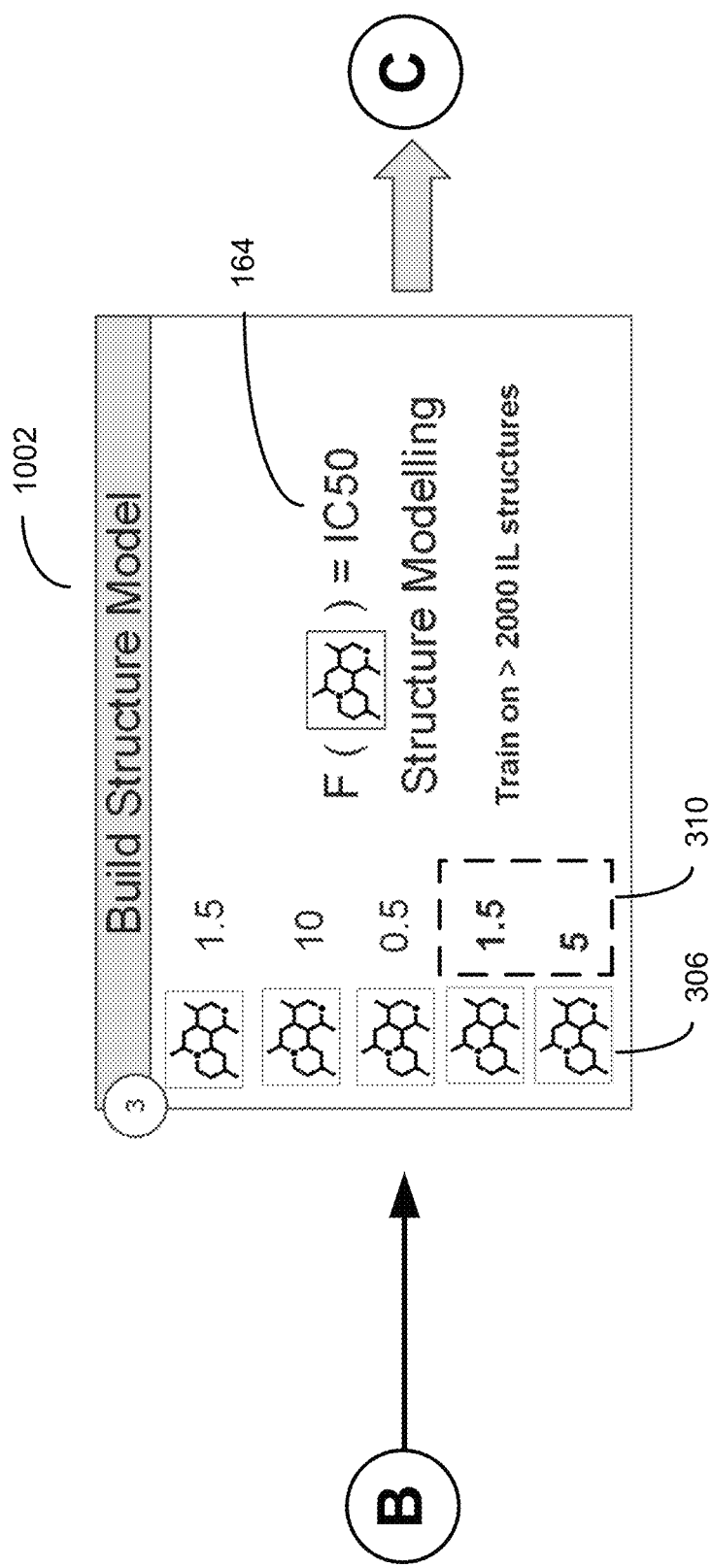

An example schematic illustrating an embodiment of this prediction is provided in FIGS. 10A-D. Consider, for example, an "intervention library" ("IL") that includes a large number of training compounds with accompanying chemical structures 306 and transcriptional signatures (e.g., vectors of abundance values), as illustrated in FIG. 10A. The IL signatures 304 can be obtained using any of the methods disclosed herein (see, e.g., the section entitled "Abundance values," above). Within the Intervention Library, a smaller subset of training compounds may have additional, measured experimental data pertaining to a particular cellular behavior of interest (e.g., a perturbational effect of interest, or an "in-vitro readout") 310. However, in some implementations, not all compounds in the Intervention Library will have measured experimental data for the perturbational effect of interest ("Unknown"), more so if the Intervention Library has a large number of training compounds. In some cases, the Intervention Library contains multiple subsets of training compounds, each subset including measured experimental data for a different perturbational effect of interest. For instance, in a library of 1000 training compounds, one set of 100 training compounds may have experimental data for binding assays (IC50), another set of 100 different training compounds may have experimental data for transcriptional assays (ddCq), and yet another set of 100 different training compounds may have imaging data. Thus, it is beneficial to be able to extrapolate from training compounds that have perturbational effect data to those that do not, using the accompanying transcriptional signatures contained in the Intervention Library.

The second model, therefore, can be used for "in-vitro dataset augmentation," that is, extrapolation of perturbational effect data using transcriptional signatures. This is illustrated, for example, in FIG. 10B, in which the second model predicts values for the perturbational effect of interest (here, "IC50," although any perturbational effect is contemplated for use in the present disclosure, as described above and as will be apparent to one skilled in the art). In some implementations, the second model is trained on a small number of training compounds having perturbational effect data relative to the number of training compounds to which the perturbational effect data is extrapolated (e.g., the number of training compounds in the Intervention Library having perturbational effect data for the perturbational effect of interest relative to the number of training compounds in the Intervention Library that do not have perturbational effect data for the perturbational effect of interest).

In some implementations the second model is trained on at least 10, at least 50, at least 100, at least 1000, at least 10,000, or at least 100,000 training compounds. In some implementations, the second model is trained on no more than 1 million, no more than 100,000, no more than 10,000, no more than 1000, no more than 100, or no more than 50 compounds. In some embodiments, the second model is trained on from 10 to 100, from 50 to 200, from 100 to 1000, from 800 to 40,000, from 20,000 to 200,000, or from 100,000 to 1 million training compounds. In some implementations, the second model is trained on another range of training compounds starting no lower than 10 compounds and ending no higher than 1 million training compounds.

Alternatively or additionally, in some embodiments, the second model extrapolates perturbational effect data to at least 10, at least 50, at least 100, at least 1000, at least 10,000, at least 100,000, at least 1 million, at least 10 million, or at least 100 million training compounds. In some implementations, the second model extrapolates perturbational effect data to more than 1 billion, no more than 100 million, no more than 1 million, no more than 100,000, no more than 10,000, no more than 1000, no more than 100, or no more than 50 compounds. In some embodiments, the second model extrapolates perturbational effect data to from 10 to 1000, from 500 to 5000, from 3000 to 100,000, from 80,000 to 1 million, from 1 million to 100 million, or from 100 million to 1 billion training compounds. In some implementations, the second model extrapolates perturbational effect data to another range of training compounds starting no lower than 10 compounds and ending no higher than 1 million training compounds.

For example, in some embodiments, the second model is trained on no more than 100 training compounds having perturbational effect data, and is used to extrapolate perturbational effect data to at least 2000 training compounds that do not have perturbational effect data for the perturbational effect of interest.

Figure 10D:
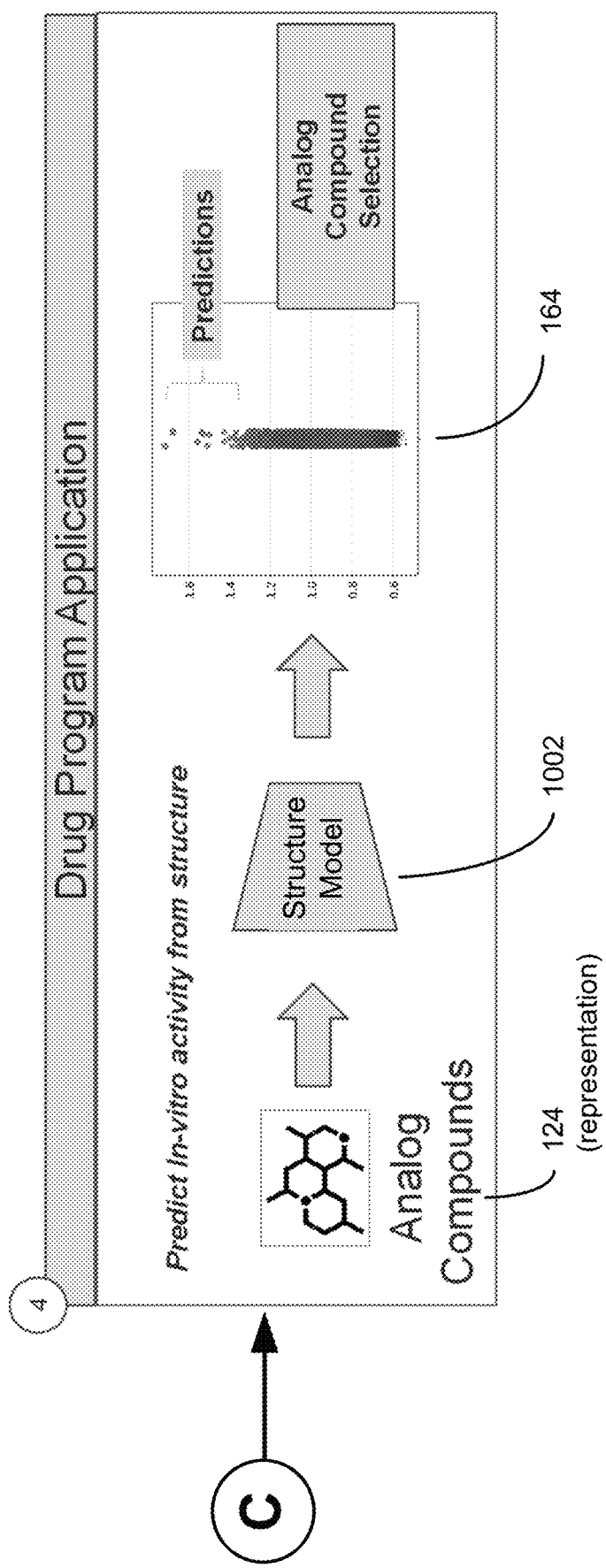

Referring again to FIGS. 10C-D, the (i) chemical structures 306, or a representation thereof 124, and the (ii) accompanying perturbational effect data 310 (both measured and/or predicted/extrapolated), for each of the training compounds in the Intervention Library, are used to train a primary model 1002 (e.g., the structure model, or the first model) to output the predicted perturbational effect 164. Optionally, a vector of abundance values for a biological context (e.g., basal expression of a cell line in the presence of control solvent only) is further inputted into the second model. Predictions can be ranked, compared to reference compounds or reference perturbational effects, and/or otherwise analyzed to determine "hit" test compounds for further development. FIG. 10D illustrates, for example, the ability of the model to predict in vivo (e.g. phenotypic) impact from compound structure despite a paucity of phenotypic data to work from. As shown in FIG. 10D, the model relies on a relative "abundance" of transcriptional data. In embodiments, the model relies on the use of minimal phenotypic data to navigate and inform more numerous transcriptional data to predict phenotypic outcomes of any given compound structure.

Additional Embodiments

Another aspect of the present disclosure provides a computer system, comprising one or more processors and memory, the memory storing instructions for performing a method for associating a test chemical compound with a reference compound. In some embodiments, the method comprises (A) obtaining, in electronic form, a fingerprint of a chemical structure of the test chemical compound; (B) obtaining, in electronic form, from one or more reference assay experiments, a plurality of abundance values for each cellular constituent in a set of cellular constituents across a first plurality of cells that have been exposed to a control solution composition free of the test chemical compound; and (C) responsive to inputting the fingerprint of the chemical structure of the test chemical compound and the plurality of abundance values into a first model, retrieving, as output from the first model, a predicted similarity between (i) a predicted perturbational effect of the test chemical compound across the set of cellular constituents and (ii) a measured cell-based perturbational effect of the reference chemical compound across the set of cellular constituents, where, when the predicted similarity achieves a threshold similarity, the test chemical compound is associated with the reference compound and wherein the first model comprises a first plurality of parameters.

Another aspect of the present disclosure provides a non-transitory computer-readable medium storing one or more computer programs, executable by a computer, for associating a test chemical compound with a reference compound, the computer comprising one or more processors and a memory, the one or more computer programs collectively encoding computer executable instructions that perform a method. In some embodiments, the method comprises (A) obtaining, in electronic form, a fingerprint of a chemical structure of the test chemical compound; (B) obtaining, in electronic form, from one or more reference assay experiments, a plurality of abundance values for each cellular constituent in a set of cellular constituents across a first plurality of cells that have been exposed to a control solution free of the test chemical compound; and (C) responsive to inputting the fingerprint of the chemical structure of the test chemical compound and the plurality of abundance values into a first model, retrieving, as output from the first model, a predicted similarity between (i) a predicted perturbational effect of the test chemical compound across the set of cellular constituents and (ii) a measured cell-based perturbational effect of the reference chemical compound across the set of cellular constituents, where, when the predicted similarity achieves a threshold similarity, the test chemical compound is associated with the reference compound and wherein the first model comprises a first plurality of parameters.

Another aspect of the present disclosure provides a computer system, comprising one or more processors and memory, the memory storing instructions for performing a method for associating a test chemical compound with a reference compound, the method comprising: (A) obtaining a fingerprint of a chemical structure of the test chemical compound; and (B) responsive to inputting the fingerprint of the chemical structure of the test chemical compound and the plurality of abundance values into a first model, retrieving, as output from the first model, a predicted perturbational effect of the test chemical compound.

Another aspect of the present disclosure provides a non-transitory computer-readable medium storing one or more computer programs, executable by a computer, for associating a test chemical compound with a reference compound, the computer comprising one or more processors and a memory, the one or more computer programs collectively encoding computer executable instructions that perform a method comprising: (A) obtaining a fingerprint of a chemical structure of the test chemical compound; and (B) responsive to inputting the fingerprint of the chemical structure of the test chemical compound and the plurality of abundance values into a first model, retrieving, as output from the first model, a predicted perturbational effect of the test chemical compound.

Still another aspect of the present disclosure provides a computer system having one or more processors, and memory storing one or more programs for execution by the one or more processors, the one or more programs comprising instructions for performing any of the methods and/or embodiments disclosed herein. In some embodiments, any of the presently disclosed methods and/or embodiments are performed at a computer system having one or more processors, and memory storing one or more programs for execution by the one or more processors.

Yet another aspect of the present disclosure provides a non-transitory computer readable storage medium storing one or more programs configured for execution by a computer, the one or more programs comprising instructions for carrying out any of the methods disclosed herein.

III. Examples

Provided herein are example performance measures and therapeutic applications of models for associating compounds with physiological conditions.

Example 1—Prediction and Validation of Test Chemical Compounds with Perturbational Similarity to a Reference Compound An example prediction and validation workflow was performed to obtain, using a first model (e.g., a structure behavior relationship model), test chemical compounds with transcriptional similarity to a reference compound in accordance with an embodiment of the present disclosure, with reference to FIGS. 4A-E, 5A-B, 6A-B, 7, and 8A-B.

To obtain labels (e.g., ground truth labels) for training and testing the first model's ability to generate predicted similarities for test chemical compounds, a second model (e.g., a transcriptional classifier) was obtained. The second model was used to generate, for a respective input compound, a score that indicated whether, or to what degree, a predicted perturbational effect of the respective input compound across a set of cellular constituents matched a measured cell-based perturbational effect of the reference chemical compound across the set of cellular constituents.

In accordance with some embodiments of the present disclosure, the first model provides similarity predictions based on chemical structures and control solution-specific transcriptional signatures, whereas the second model provides similarity predictions based on test chemical compound-specific transcriptional signatures. Advantageously, the similarity predictions generated by the second model are used to train the first model, thus increasing the accuracy and predictive power of the first model while reducing the complexity and cost of its inputs. Inputs based on chemical structure (e.g., the first model) and/or compound-specific transcriptional signatures (e.g., the second model) are illustrated, for example, in FIG. 4A.

Defining a Transcriptional Signature.

A set of 50 genes was selected as the set of cellular constituents. These 50 genes were chosen as the genes having the highest regression coefficients (e.g., logistic regression coefficients), measured independently using abundance values for training compounds for each respective gene in a plurality of candidate genes.

Briefly, for each respective training compound in a plurality of training compounds, a corresponding set of abundance values was obtained, where the corresponding set of abundance values included one or more abundance values for each respective gene in a plurality of candidate genes. For a respective training compound, the corresponding set of abundance values was obtained from cells exposed to the respective training compound solvated in a control solution, and were further normalized against a control set of abundance values obtained from cells exposed to the control solution free of the training compound. Thus, each set of abundance values provided a differential transcriptional profile obtained from cells exposed to a respective training compound relative to a control.

For each respective gene in the plurality of candidate genes, a preliminary logistic regression analysis was performed to determine the relationship between the respective gene's abundance values and a similarity to a transcriptional profile obtained for a reference compound (e.g., a differential transcriptional profile obtained from cells exposed to the reference compound relative to a control). Regression coefficients were obtained from the respective analysis corresponding to each respective gene in the plurality of candidate genes, and the 50 genes having the highest absolute value regression coefficients were selected as the final set of cellular constituents, thus establishing a transcriptional signature of interest.

Second Model: Classifier

For the second model, a logistic regression model was obtained and trained on transcriptional data obtained over 18 assay experiments. Each respective assay experiment included single-cell RNA sequencing analysis of a different set of chemical compounds prepared using a respective compound library and a respective set of plates. Experiments 3 and 4 were removed due to variations in experimental conditions. The model was trained on experiments 1, 2, and 5-15, while experiments 16-18 were held out for testing. In total, the full transcriptional dataset included 2,512 total data points, of which 432 observations corresponded to the reference compound, with 296 unique chemical compounds used to obtain abundance values across the 18 assay experiments. The 13 experiments used for training included 1,810 total data points, of which 338 observations corresponded to the reference compound. The held-out experiments used for testing included 702 total data points, of which 94 observations corresponded to the reference compound, with abundance values for 79 unique test chemical compounds unseen by the model during training.

Using the 50 genes as the set of cellular constituents, input to the second model (e.g., the transcriptional classifier) for training included, for each training compound in the training set, a corresponding vector of abundance values. Each element in the vector of abundance values was a difference between (a) an abundance of a corresponding cellular constituent in the set of cellular constituents in a corresponding reference cell-based assay upon exposure to the respective training compound solvated in the control solution, and (b) an abundance of a corresponding cellular constituent in the set of cellular constituents in a corresponding reference cell-based assay upon exposure to the control solution free of the respective training compound.

In other words, for each respective training compound, the input to the second model was represented as a "V-score" vector of 50 elements, where each element in the V-score vector corresponded to a different respective gene in the set of 50 genes. For each respective gene in the set of 50 genes, the corresponding vector entry was a difference between (a) the abundance values obtained from cells exposed to the respective training compound solvated in DMSO, and (b) a control set of abundance values obtained from cells exposed to DMSO alone. Thus, as described above, each vector entry provided a differential gene expression value for cells exposed to the respective training compound relative to a control. V-score vectors are illustrated, for example, in FIG. 4B.

After training the second model, the held-out experiments were inputted to the second model to test and validate the second model's ability to output similarity scores that accurately match whether a respective test chemical compound has a similar transcriptional signature to the reference transcriptional signature (e.g., whether, or to what degree, a predicted perturbational effect of the respective training compound across the set of cellular constituents matches a measured cell-based perturbational effect of the reference chemical compound across the set of cellular constituents). Outputted similarity scores ranged from 0 to 1, with higher values indicating greater confidence or probability that the transcriptional signature of the test chemical compound matched the transcriptional signature of the reference compound. V-score vectors corresponding to the reference compound were also included in the testing set as a positive control (e.g., to confirm that the model generates high similarity scores for reference compound inputs). Alternatively, test compounds that generated high similarity scores were considered to be "hits." The second model's output was compared against known similarity labels (e.g., hits and non-hits) to evaluate the accuracy and performance of the model.

Figure 5A:
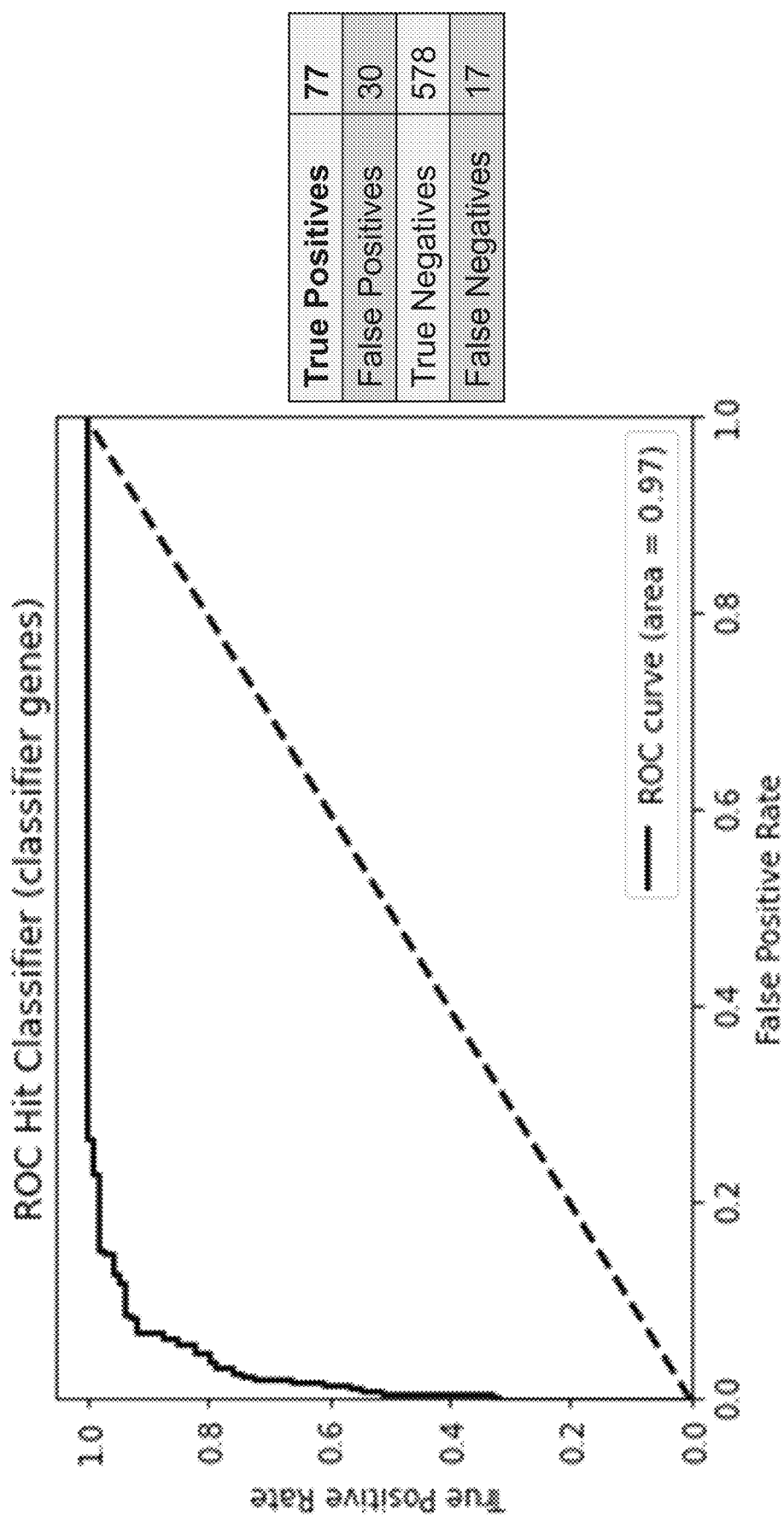
FIGS. 5A and 5B collectively illustrate classification of transcriptional signatures using logistic regression, where positive predictions indicate similarity to a target transcriptional profile of interest, in accordance with an embodiment of the present disclosure.
Figure 5B:
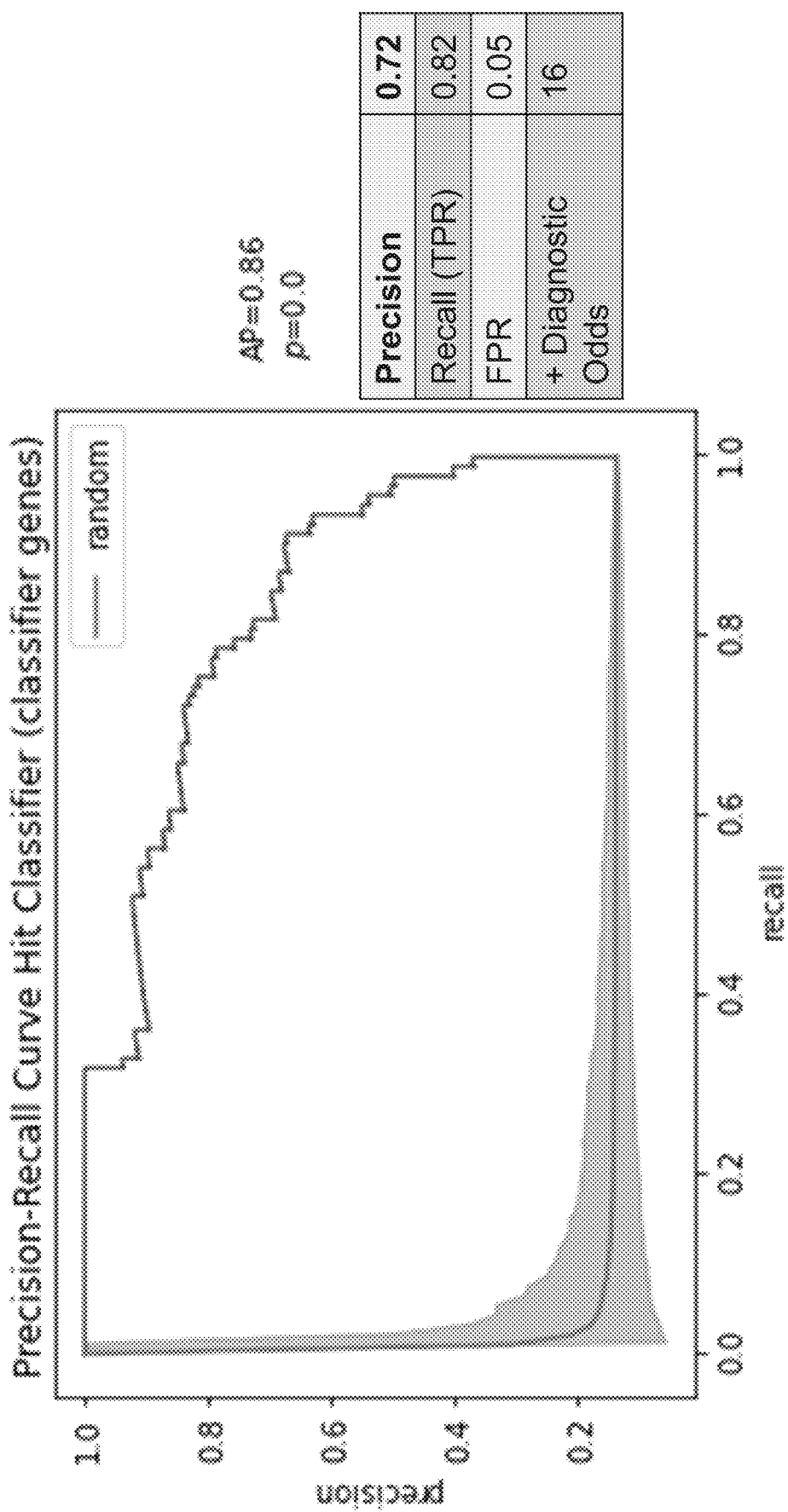

In the testing set, good separation of high and low similarity scores was observed between true hits and non-hits. FIGS. 5A-B illustrate various performance metrics that show the second model's ability to classify transcriptional signatures using logistic regression, where positive predictions classify transcriptional signatures as being similar to the target transcriptional profile of the reference compound. In FIG. 5A, the receiver operating characteristic area under the curve (ROC AUC) shows an aggregate measure of performance across a range of classification thresholds for the true positive rate and false positive rate parameters. ROC AUC for the second model was 0.97, indicating a 97% chance that the model's outputted similarity scores are accurate. The dashed trendline illustrates the likelihood that a respective test compound will be accurately classified as a hit or non-hit by chance. Thus, the second model's predictive ability is improved over random chance. A summary of classification of the data points is also provided. Of the 702 total data points in the held-out testing set, the second model predicted 77 true positives, 30 false positives, 578 true negatives, and 17 false negatives.

In FIG. 5B, the precision-recall curve illustrates the balance between precision and recall over a range of classification thresholds. A high area under the curve represents both high recall and high precision, where high precision relates to a low false positive rate and high recall relates to a low false negative rate. More particularly, precision (P) is defined as the number of true positives ($T_p$) over the number of true positives plus the number of false positives ($F_p$): $P=T_p/(T_p+F_p)$; and recall (R) is defined as the number of true positives ($T_p$) over the number of true positives plus the number of false negatives ($F_n$): $R=T_p/(T_p+F_n)$. Average precision (AP) summarizes the plot as the weighted mean of precisions achieved at each threshold, with the increase in recall from the previous threshold used as the weight. The diagnostic odds ratio (DOR) indicates the odds of a prediction of similarity for a test compound that is a true "hit" relative to the odds of a prediction of similarity for a test compound that is a "non-hit." For instance, a diagnostic odds ratio of 10 would indicate that a compound that is predicted by the second model to be similar is 10 times more likely to be a true "hit" than a "non-hit." The second model achieved a precision of 0.72, recall of 0.82, and average precision of 0.86 with a significance of p=0.0. The second model's false positive rate (FPR) was 0.05, with diagnostic odds of 16. For comparison, the shaded line provides a precision-recall curve for random predictions ("random"), further illustrating that the second model's predictive ability is improved over random chance.

Given the similarity scores outputted by the second model, a threshold similarity (e.g., a cutoff threshold) was selected to separate test compounds into classified "hits" and "non-hits" and to provide ground truth labels for training the first model (e.g., the structure behavior relationship model). A false positive rate (FPR) of 0.05 was selected as the classification threshold, which corresponded to a threshold similarity score of 0.15 or greater. Thus, test compounds that achieved a similarity score of at least 0.15 by the second model were classified as "hits," and test compounds having a similarity score of less than 0.15 were classified as "non-hits." Classification scores for hits and non-hits based on V-score vectors are illustrated, for example, in FIG. 4D. The second model (e.g., the transcriptional classifier) therefore provided a data-driven approach to identifying test compounds having a target transcriptional signature (e.g., similarity to a reference transcriptional signature) with high precision.

Figure 3:
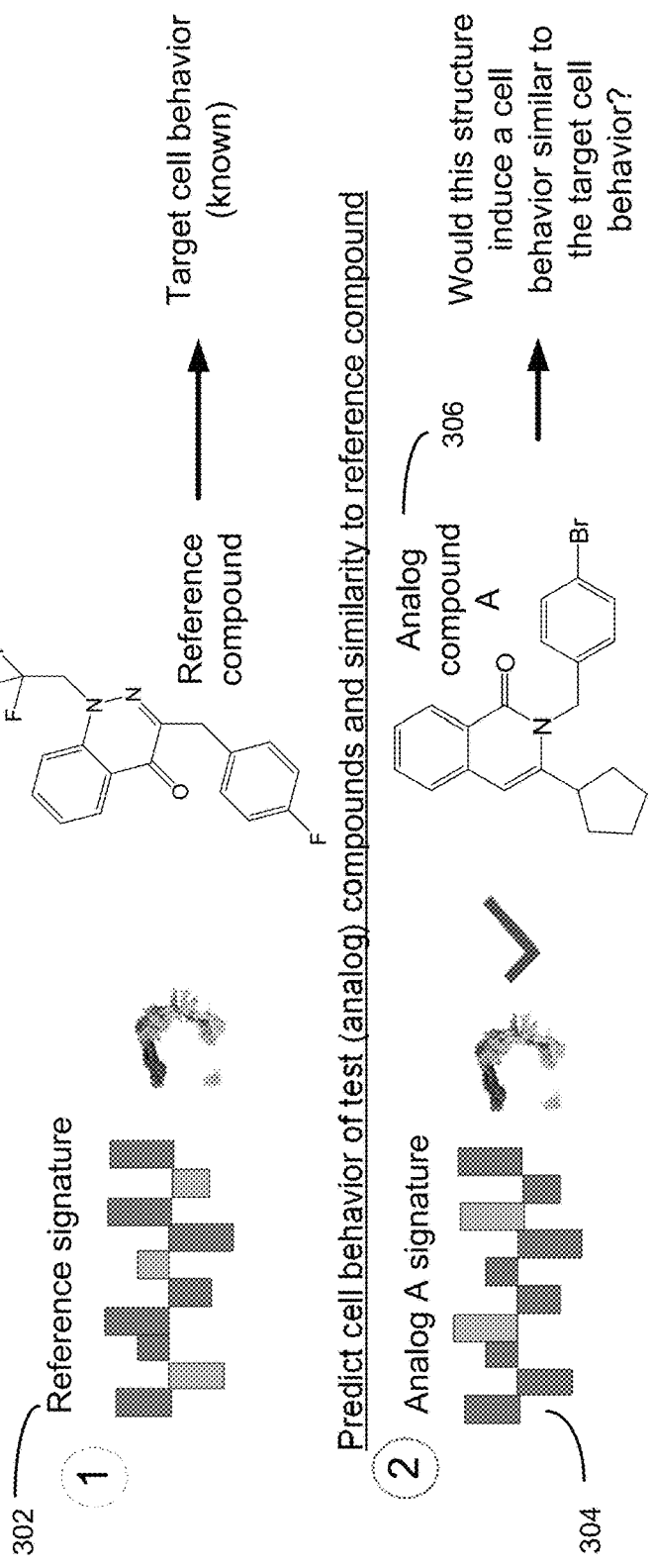
FIG. 3 illustrates an example schematic for optimizing test chemical compounds (e.g., test compound A and test compound B) towards a target perturbational effect across a set of cellular constituents (e.g., cell behavior or CB), in accordance with some embodiments of the present disclosure.
Figure 3:
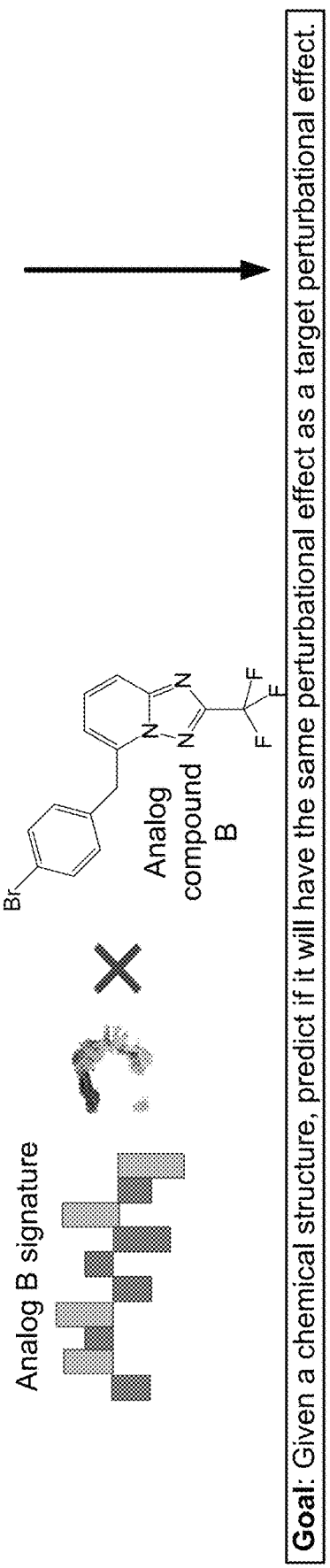
Figure 4A:
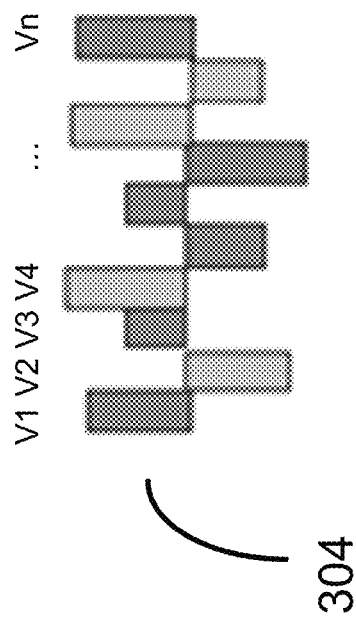
Figure 4B:
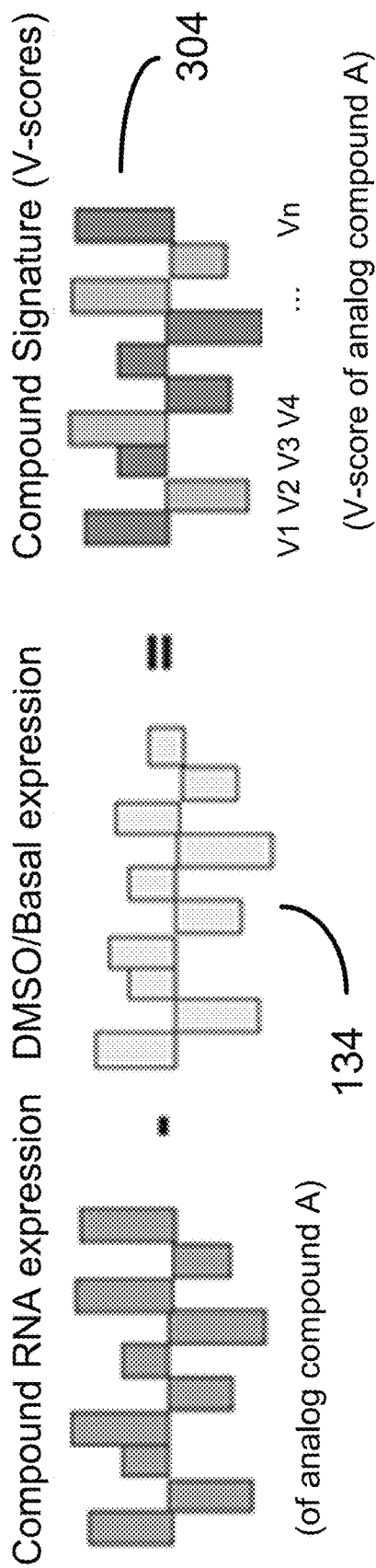
Figure 4C:
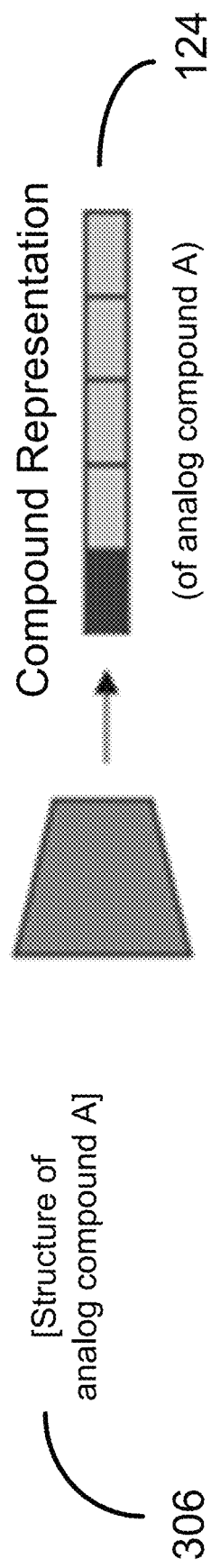
Figure 4E:
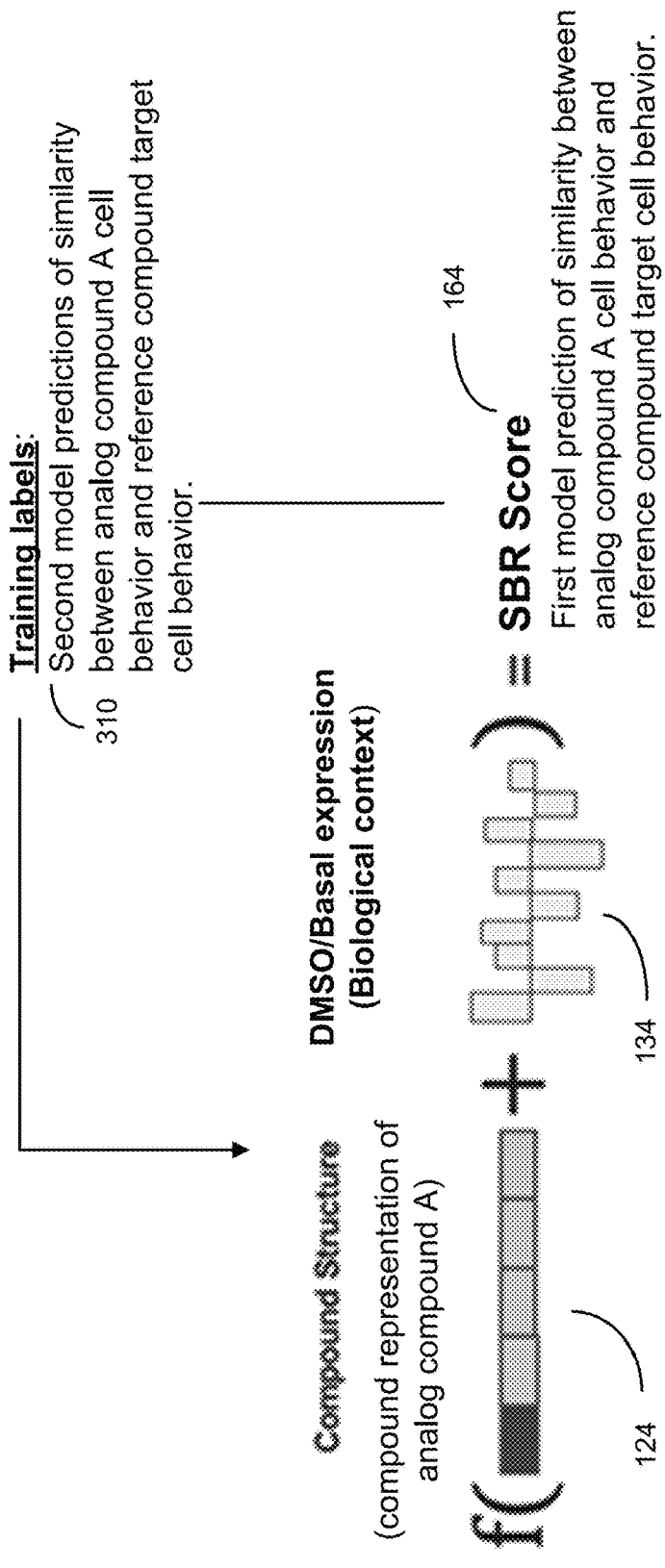

First Model (Structure Behavior Relationship):

FIG. 3 illustrates an example schematic for optimizing test chemical compounds (e.g., test compound A and test compound B) towards a target perturbational effect across a set of cellular constituents (e.g., cell behavior or CB), in accordance with some embodiments of the present disclosure. In particular, the schematic depicts the use of the second model (e.g., the transcriptional classifier) for determining similarity predictions, which are also useful as ground truth labels for training the first model (e.g., the structure behavior relationship model).

At step 1, a reference compound is identified, and a measured cell-based perturbational effect of the reference compound (e.g., the target transcriptional signature for the reference compound or "CB target behavior") is defined. At step 2, the perturbational effects of a plurality of test chemical compounds are obtained (e.g., as a vector of abundance values, such as a V-score vector), and a predicted similarity score for each test chemical compound is generated by a second model (e.g., a transcriptional classifier). As an illustrative example, a first test chemical compound (test compound A) is classified as a "hit," and a second test chemical compound (test compound B) is classified as a "non-hit." Using the chemical structure of test compounds A and B, the first model was trained to predict similarity between test compound and reference compound-induced cell behaviors, without the need for compound-specific transcriptional data (e.g., V-score vectors) as input.

For the first model, a gradient boosted decision tree algorithm including a plurality of parameters was obtained and trained on transcriptional data obtained over 19 assay experiments. As described above, each respective assay experiment included single-cell RNA sequencing analysis of a different set of chemical compounds prepared using a respective compound library and a respective set of plates. The model was trained on experiments 1-16, while experiments 17-19 were held out for testing. Cumulatively, the training experiments included 290 unique training compounds used to obtain abundance values across the 16 assay experiments, while the held-out experiments used for testing included abundance values for 50 unique test chemical compounds unseen by the model during training. Of these 50 test chemical compounds, 6 compounds were classified as "hits" by the second model (e.g., the transcriptional classifier).

As previously described, the first model was trained to predict similarity between the predicted transcriptional profiles induced by the test chemical compounds and the target transcriptional profile induced by the reference compound, based only on the fingerprint of the chemical structure of the test chemical compounds and a control set of abundance values, for the set of 50 genes, obtained from cells exposed to a control DMSO solution alone. The input to the first model was provided as a vector in which a vector representation of the chemical structure (e.g., a fingerprint) was concatenated to a vector containing control abundance values for the set of 50 genes. The DMSO-specific abundance values were obtained using the same samples used to calculate the V-score vectors for the second model. Example schematics for vector representations of compound structures and concatenated input vectors for the first model are provided, for instance, in FIGS. 4C and 4E.

Training the first model was performed by, for each respective training compound in the plurality of (e.g., 290) training compounds, obtaining a respective training fingerprint of a chemical structure of the respective training compound. A plurality of abundance values for each cellular constituent in a set of cellular constituents across a first plurality of cells been exposed to a control solution free of the test chemical compound was also obtained from one or more reference single-cell assay experiments (e.g., the DMSO-specific abundance values for each gene in the set of 50 genes). The respective fingerprint of the chemical structure of the respective training compound and the plurality of control-specific abundance values were inputted into the first model (e.g., as a concatenated vector).

Responsive to the inputting, the first model generated, as respective training output, a corresponding training predicted similarity between (a) a predicted perturbational effect of the respective training compound across the set of cellular constituents and (b) a measured cell-based perturbational effect of the reference chemical compound across the set of cellular constituents. A respective difference to a loss function was applied to obtain a respective output of the loss function, where the respective difference was between (a) the corresponding training predicted similarity from the first model and (b) a score from the second model that indicated whether, or to what degree, a predicted perturbational effect of the respective training compound across the set of cellular constituents matched a measured cell-based perturbational effect of the reference chemical compound across the set of cellular constituents, as described above. The respective output of the loss function was then used to adjust the first plurality of parameters, thereby training the first model.

After training the first model, the model's ability to accurately predict similarity based on chemical structure was validated on the testing set. Using the trained first model, each test chemical compound (e.g., in the set of 50 held-out test chemical compounds) was evaluated by a procedure including obtaining a fingerprint of a chemical structure of the test chemical compound and a plurality of control-specific abundance values, as described above. Responsive to inputting the fingerprint and the plurality of abundance values into the first model (e.g., as a concatenated vector), a predicted similarity was retrieved, as output from the first model, between (i) a predicted perturbational effect of the test chemical compound across the set of cellular constituents and (ii) a measured cell-based perturbational effect of the reference chemical compound across the set of cellular constituents.

Outputted similarity scores ranged from 0 to 1, with higher values indicating greater confidence or probability that the predicted transcriptional signature of the test chemical compound was similar to the transcriptional signature of the reference compound. A chemical structure corresponding to the reference compound was also included in the testing set as a positive control (e.g., to confirm that the model generates a high similarity score for the reference compound structure). When the predicted similarity achieved a threshold similarity (e.g., 0.15), the test chemical compound was associated with the reference compound. The first model's output was compared against known similarity labels (e.g., hits and non-hits classified by the second model) to evaluate the accuracy and performance of the model.

As illustrated in FIGS. 6A-B, the first model exhibited strong predictability, as measured by receiver operating characteristic area under curve (ROC AUC=0.91) and average precision metrics (AP=0.87, p=0.0). As further illustrated in FIG. 7, the predicted similarities generated by the first model were generally higher for test compounds that were classified as transcriptional hits by the second model than for test compounds that were classified as non-hits by the second model, with high similarity predicted for the positive control. In particular, all but one of the test compounds that were classified as a "hit" by the second model exceeded the threshold similarity of 0.15 and were accordingly associated with the reference compound (e.g., "Small Molecule Analog Predicted Hits"). The maximum Tanimoto coefficient for the set of held-out testing compounds was less than or equal to 0.67, indicating that all compounds in the testing set were considered to be dissimilar in structure from the reference compound. This illustrates the first model's capability to accurately predict similarity between test and reference transcriptional signatures even for test compounds with dissimilar chemical structures, highlighting the broad applicability of the presently disclosed systems and methods towards the discovery of new, structurally diverse compounds that induce similar perturbational effects (e.g., for drug development and therapeutics). Note that the Tanimoto (or Jaccard) coefficient T is a similarity measure for comparing chemical structures represented as fingerprints, where T>0.85 indicates structural similarity.

Transcriptional Validation of Predicted Similarity

Test chemical compounds that were predicted as transcriptionally similar to the reference compound ("predicted hits") were validated by comparing the transcriptional responses (e.g., differential expression for a panel of genes) induced in test cells when exposed to the predicted hits versus when exposed to the reference compound. As illustrated in the heatmaps in FIGS. 8A-B, the transcriptional responses induced by the predicted hits and the reference compound were highly similar across a panel of genes that were selected as the most highly correlated between the reference compound and the predicted hits (e.g., degree of downregulation indicated by shading only for negative values in log fold change; degree of upregulation indicated by asterisks and shading for positive values in log fold change). In contrast, a set of random control compounds (non-hits) induced transcriptional responses in the panel of genes that were substantially different from that of the reference compound. These results demonstrate the ability of the first model to accurately predict whether a test chemical compound induces behavioral responses (e.g., transcriptional responses) that are similar to a target behavioral response induced by a reference compound.

The data show that the first model for determining an association between a test compound and a reference compound (e.g., predicting structure behavior relationships) is able to correctly predict test chemical compounds that have a similar perturbational effect as the reference compound, using only the chemical structure of the test chemical compound and a control set of abundance values. The dissimilarity of the chemical structures identified as predicted hits further illustrates the ability of the first model to generalize to new compounds with diverse chemical structures.

Figure 9:
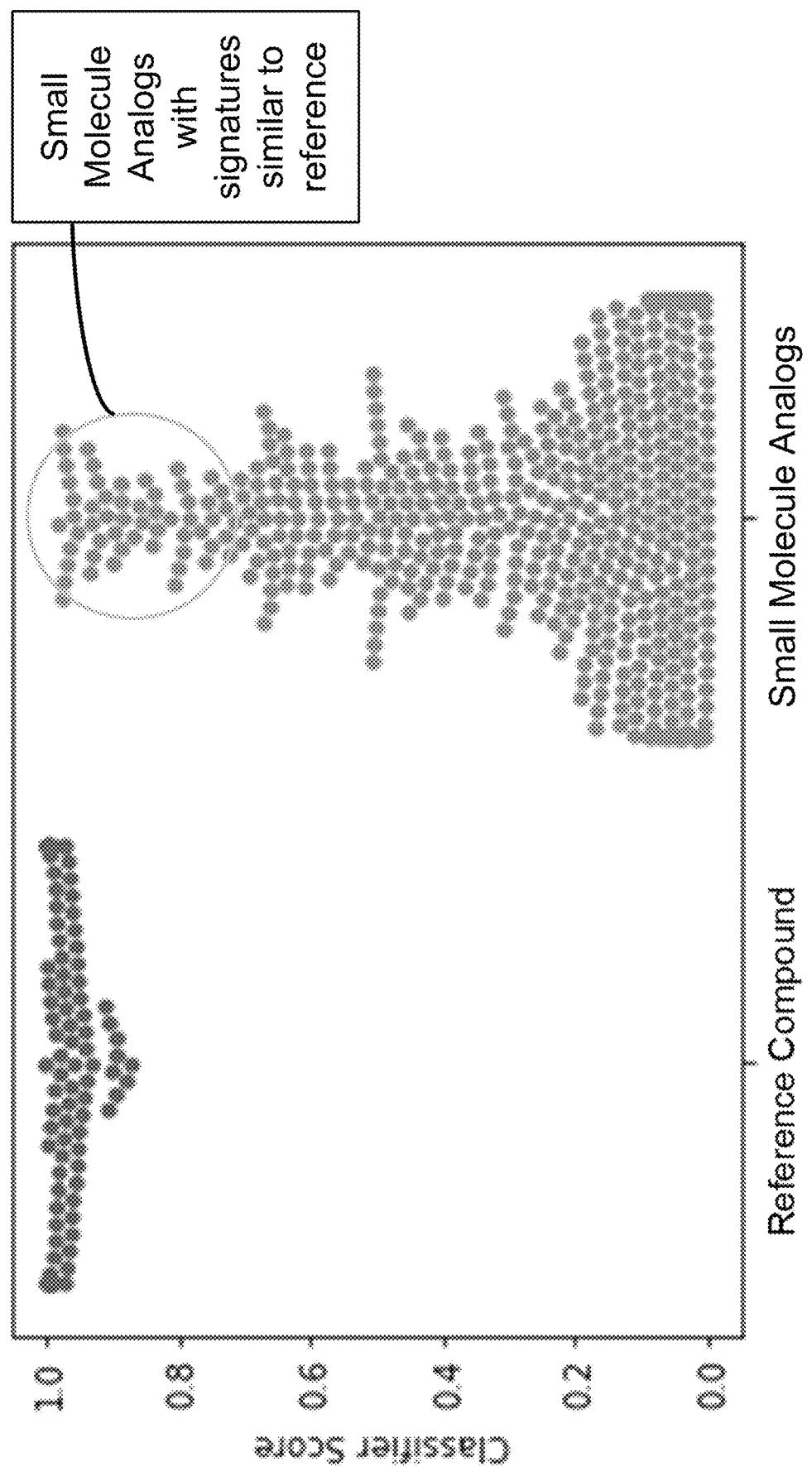
FIG. 9 illustrates an example validation of a second model for classification of transcriptional signatures using a set of positive controls, in accordance with an embodiment of the present disclosure.

Example 2—Validation of the Second Model (Transcriptional Classifier) for Classifying Transcriptional Similarity on Positive Controls An example validation of a second model for classification of transcriptional signatures using a set of positive controls was performed, in accordance with an embodiment of the present disclosure, with reference to FIG. 9.

A second model (e.g., a transcriptional classifier) was trained to generate, for a respective compound, a score indicating whether, or to what degree, a predicted perturbational effect of the respective compound across a set of cellular constituents matches a measured cell-based perturbational effect of a reference chemical compound across the set of cellular constituents. The set of cellular constituents included a set of 50 genes selected as having the highest absolute value regression coefficients in a preliminary logistic regression analysis performed on measured cell-based transcriptional data, as described in Example 1 above. Inputs to the second model for training and testing included V-score vectors that included, for a respective training and/or test compound, for each respective gene in the set of 50 genes, a corresponding element that included a differential gene abundance calculated between (i) cells exposed to the respective compound solvated in a control solution and (ii) cells exposed to a control solution free of the respective compound (e.g., DMSO).

Training and testing (e.g., validation) of the second model was performed as described above in Example 1, using a training set and a held-out testing set. The training set included 2,034 total data points, of which 370 observations corresponded to the reference compound, while the testing set included 702 total data points, of which 92 observations corresponded to the reference compound. The 92 observations corresponding to the reference compound provided positive controls for validating the model in that the transcriptional signatures obtained for the reference compound were expected to be scored with a high similarity and high accuracy to the reference compound.

As shown in FIG. 9, the second model generated similarity scores between 0 and 1, with higher values indicating greater confidence or probability that the predicted transcriptional signature of the test chemical compound was similar to the transcriptional signature of the reference compound. All reference compounds in the testing set were accurately predicted as having a high similarity to the reference compound (similarity score of greater than 0.8), validating the positive controls. In addition, a set of test chemical compounds in the testing set that were predicted as having strong transcriptional similarity to the reference compound ("Small Molecule Analogs") were identified (circled subset, similarity score of greater than 0.65).

After training and validation, the second model was used to generate similarity scores for a set of unseen test chemical compounds. Mean similarity scores (e.g., "Classifier scores") for a subset of the unseen test chemical compounds having the highest similarity scores are provided in Table 2.

TABLE 2

Mean Classifier Scores for Top Compounds

| Compound ID | Classifier Score |
|---|---|
| 10000345 | 0.965 |
| 10033752 | 0.960 |
| 10034140 | 0.933 |
| 10033471 | 0.756 |
| 10034366 | 0.706 |
| 10033858 | 0.695 |
| 10033857 | 0.692 |
| 10034464 | 0.679 |
| 10034466 | 0.635 |
| 10034578 | 0.576 |
| 10034141 | 0.569 |
| 10034584 | 0.474 |
| 10034585 | 0.473 |
| 10034365 | 0.464 |

These results validate the ability of the second model (e.g., the transcriptional classifier) to accurately classify test chemical compounds as "hits" or "non-hits" based on transcriptional signatures, as well as the utility of the second model for generating similarity scores for new compounds. Such similarity scores can be used, for instance, as training labels to train additional models (e.g., a first model for structure behavior relationships).

Example 3—Prediction and Validation of ddCq Values for Test Chemical Compounds

An example training a prediction workflow was performed to obtain, using a first model (e.g., a structure behavior relationship model), predicted perturbational effects for test chemical compounds based on chemical structure, in accordance with an embodiment of the present disclosure, with reference to FIGS. 11A-E.

Figure 11A:
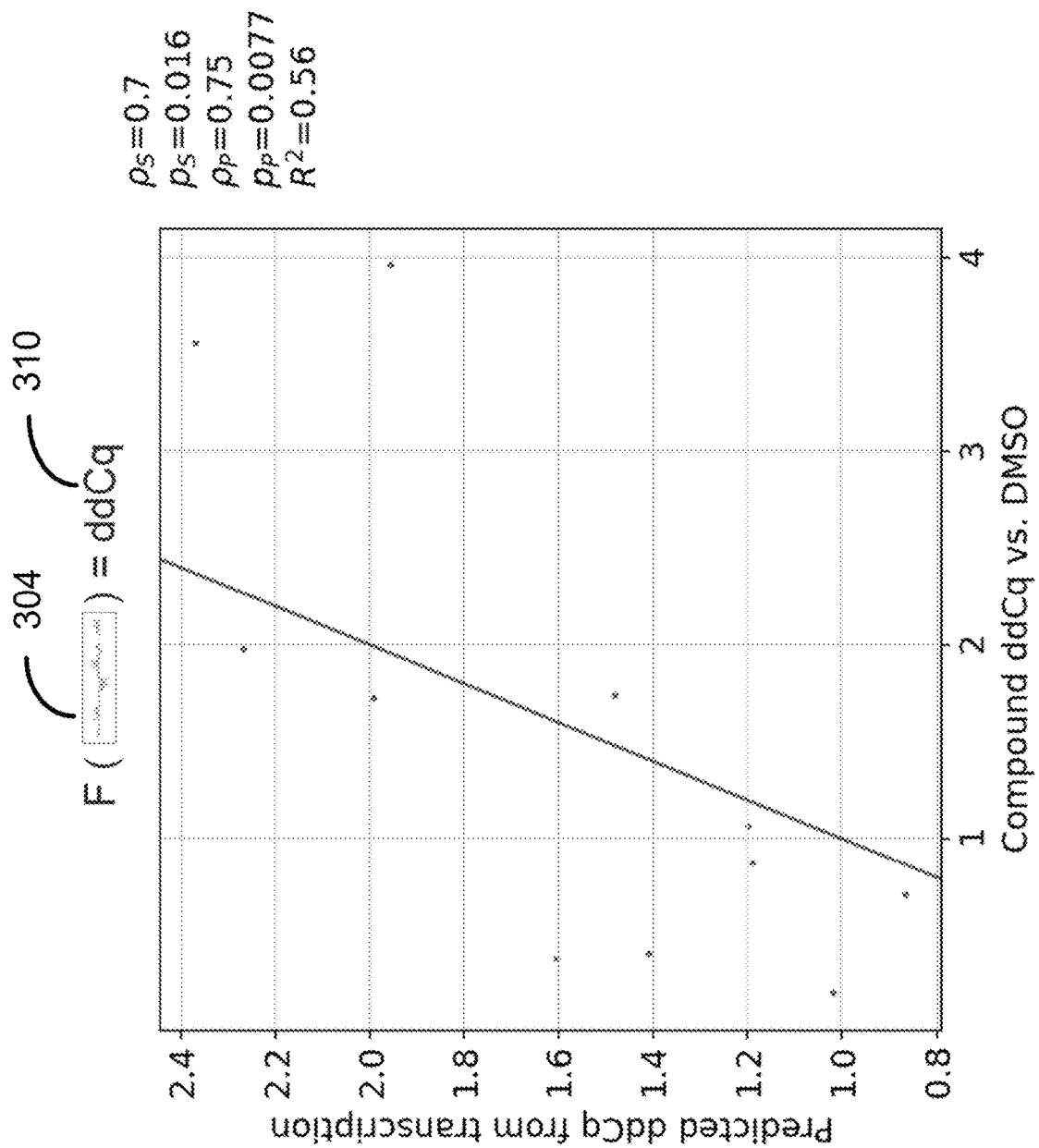
FIGS. 11A, 11B, 11C, 11D, and 11E collectively illustrate example assays demonstrating performance of a first model for associating a test chemical compound with a reference compound based on inputted test chemical compound structure, in accordance with an embodiment of the present disclosure.

A transcriptional model (e.g., second model) was trained to predict perturbational effects (ddCq) from abundance values for cellular constituents (transcriptional signatures for a set of genes) selected for a reference compound Laropiprant. 72 training compounds in an Intervention Library included qPCR data that was used to calculate the ddCq used to train the transcriptional model, using a train-test split of 61-11. FIG. 11A illustrates that the predicted values for ddCq from the trained model match the experimental values for ddCq.

Figure 11B:
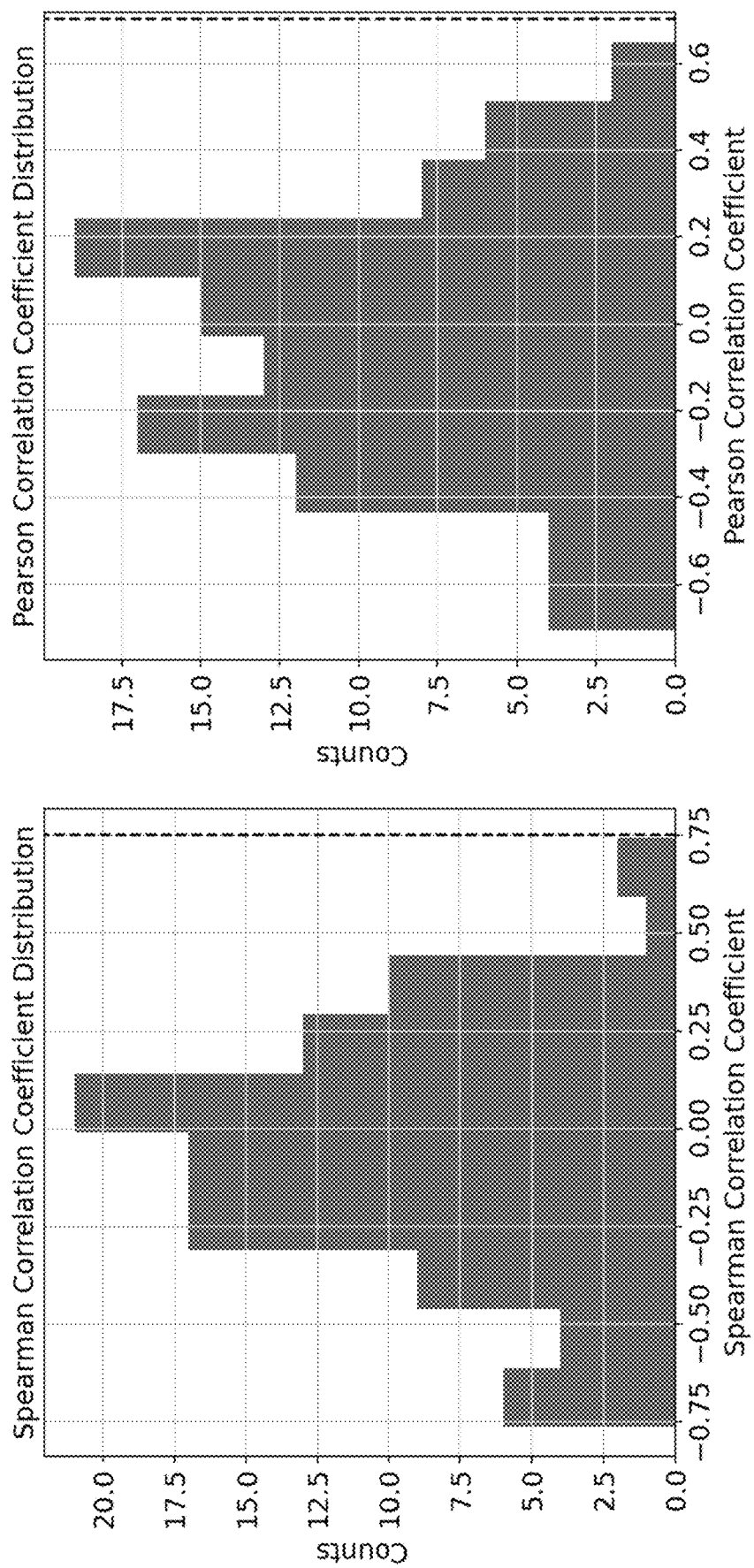

A validation experiment was also performed to determine whether the set of cellular constituents selected for the reference compound Laropiprant was robust in its predictive ability. FIG. 11B shows the results of this validation. The training of the transcriptional model was repeated 100 times, each time with a different set of 20 randomly selected genes. Distributions of both Spearman and Pearson correlation coefficient illustrate that models trained on randomly selected gene sets exhibited poorer correlation (shaded bars) between predicted and actual ddCqs compared to models trained on the Laropiprant gene set (dashed line).

The trained transcriptional model was then used to predict the ddCqs of an additional 2000+ test compounds in the Intervention Library, by inputting their transcriptional signatures into the trained second model, resulting in a total of 2833 training compounds with either measured or predicted ddCqs. Next, a structure model (e.g., first model) was trained to predict ddCq directly from chemical structure, using the compound structures of the 2833 test compounds and their corresponding ddCqs as training labels.

Figure 11C:
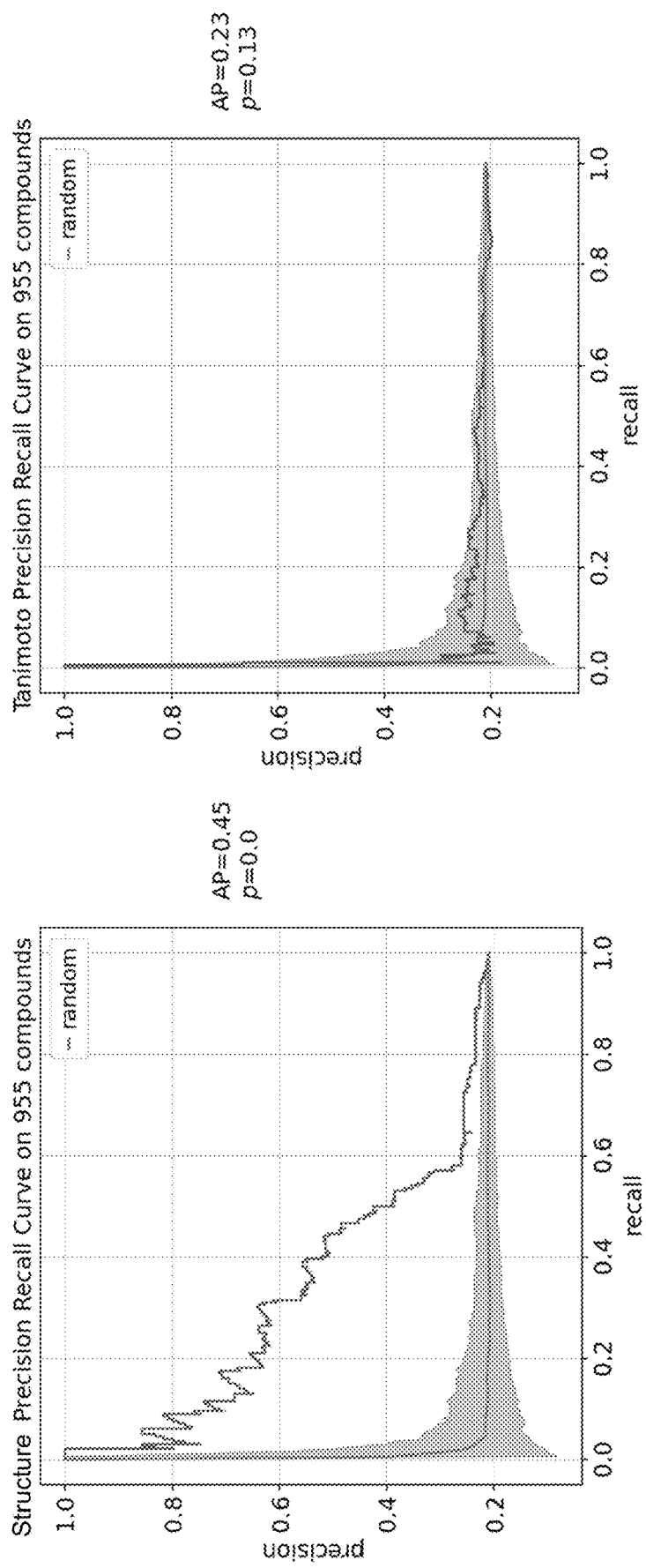
Figure 11D:
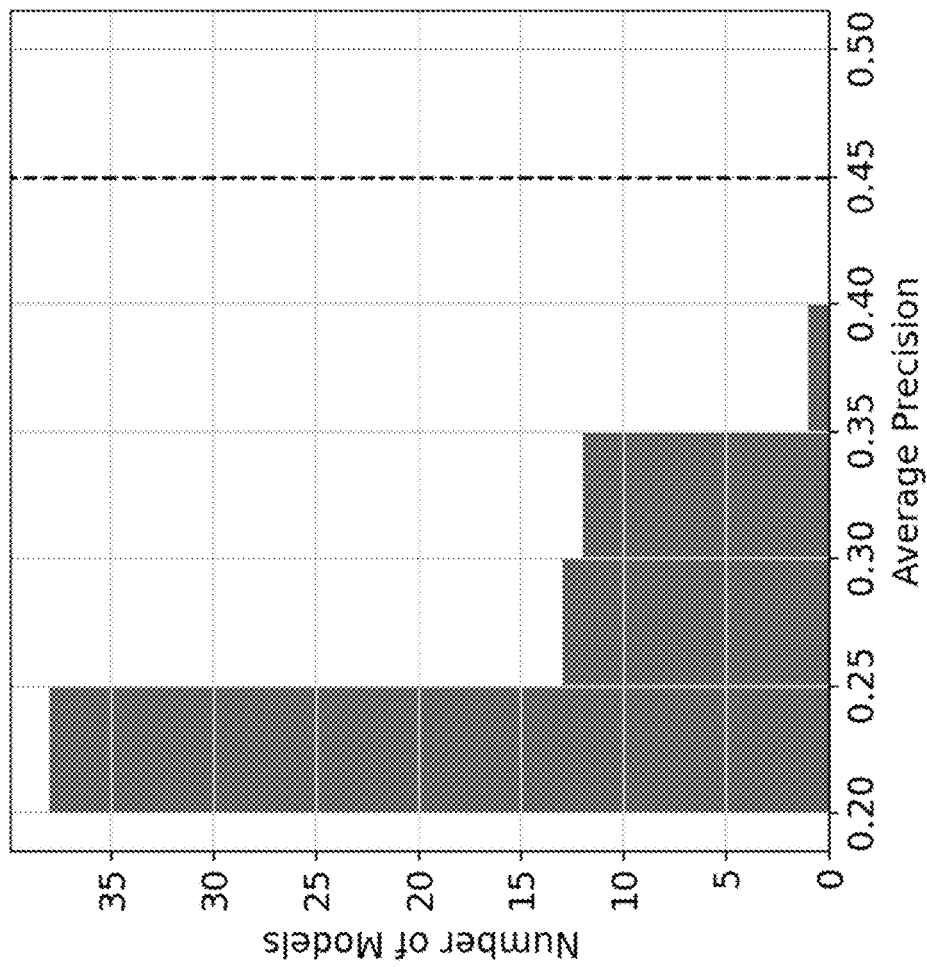

The structure model was then validated on 955 unseen test compounds that did not have transcriptional signatures (DPG8 analogs), to assess the structure model's ability to accurately predict ddCq and rank the 955 test compounds based on the similarity of their predicted ddCqs to the reference compound Laropiprant. The tested compounds were analogs of Ponalrestat. As illustrated in FIG. 11C, the structure model trained on transcriptional model-predicted ddCqs correctly ranked hits versus non-hits 2.14 times better than random value controls (shaded line). The structure model also outperformed a model trained to predict ddCqs based on Tanimoto similarity. As a control, a model trained on random ddCq values was assessed and found to perform poorly compared to the model trained on actual ddCq values predicted by the transcriptional model, as shown in FIG. 11D.

Figure 11E:
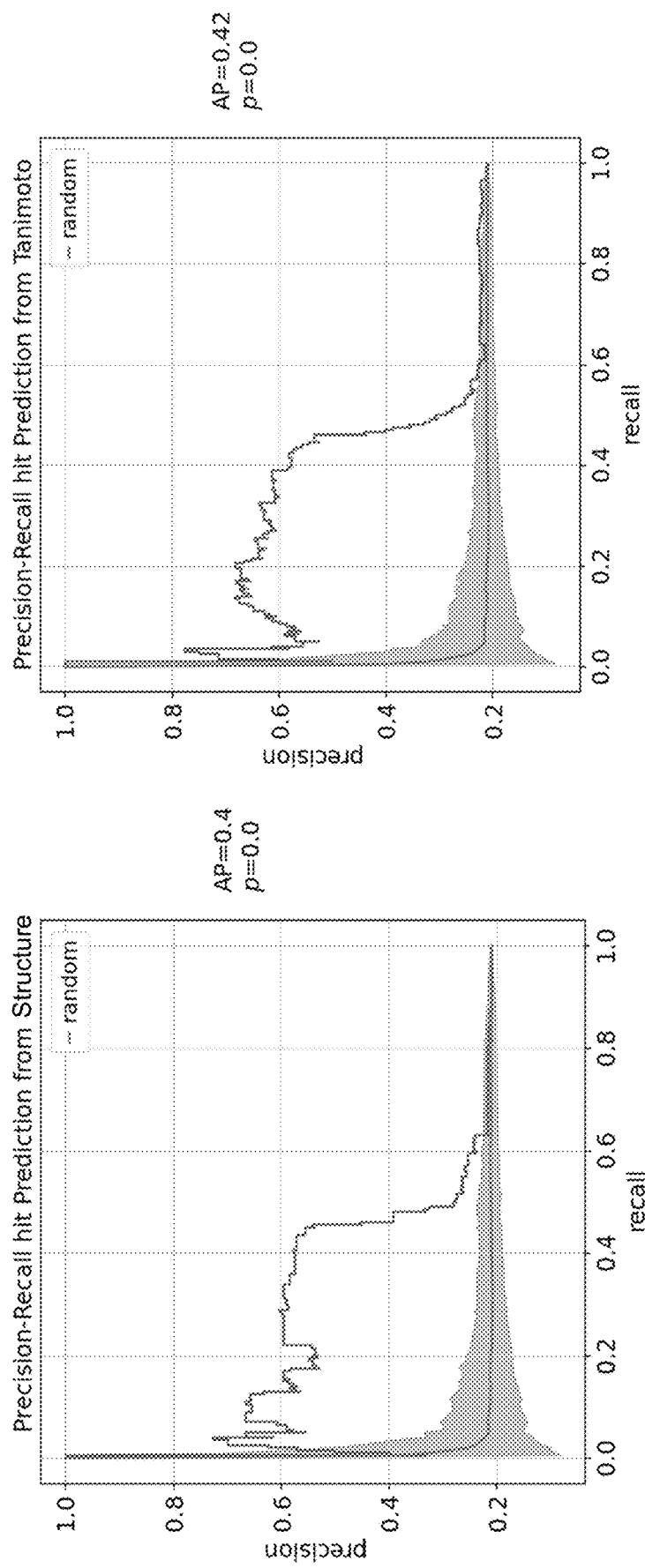

Notably, as shown in FIG. 11E, the structure model trained on compound structures and measured or predicted ddCqs showed consistent performance when using gene sets selected for the Laropiprant reference compound as well as when using gene sets selected for a second reference compound Ponalrestat. In contrast, a model trained to predict ddCqs based on Tanimoto similarity performed well for Ponalrestat, but not for Laropiprant. This consistency illustrates the robustness, generalizability, and applicability of the presently disclosed systems and methods across a range of possible reference compounds.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that includes a computer program mechanism embedded in a non-transitory computer readable storage medium. For instance, the computer program product could contain the program modules shown in any combination of FIGS. 1 and 2. These program modules can be stored on a CD-ROM, DVD, magnetic disk storage product, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method of screening a plurality of test chemical compounds against a reference compound, the method comprising:

(A) obtaining a fingerprint of a chemical structure of each test chemical compound in the plurality of test chemical compounds, wherein the plurality of test chemical compounds comprises at least ten thousand test chemical compounds;

(B) obtaining, from one or more reference assay experiments, a plurality of abundance values for each cellular constituent in a set of cellular constituents across a first plurality of cells that have been exposed to a control solution free of the plurality of test chemical compounds;

(C) for each test chemical compound in the plurality of test chemical compounds, responsive to inputting the fingerprint of the chemical structure of the test chemical compound and the plurality of abundance values into a first model, retrieving, as output from the first model, a predicted similarity between (i) a predicted perturbational effect of the test chemical compound across the set of cellular constituents and (ii) a measured cell-based perturbational effect of the reference chemical compound across the set of cellular constituents, wherein, when the predicted similarity achieves a threshold similarity, the test chemical compound is associated with the reference compound thereby identifying a subset of the plurality of test chemical compounds in the plurality of test chemical compounds that are associated with the reference compound and wherein the first model comprises a first plurality of parameters;

(D) exposing a second plurality of cells to a test chemical compound in the subset of the plurality of test chemical compounds, wherein the test chemical compound has a Tanimoto coefficient of less than 0.85 with respect to the reference chemical compound;

(E) measuring a transcriptional response of each gene in a panel of genes in the second plurality of cells after the exposing (D);

(F) exposing a third plurality of cells to the reference compound;

(G) measuring a transcriptional response of each gene in the panel of genes in the third plurality of cells after the exposing (F); and (H) determining that a transcriptional response to the test compound and the reference compound is similar across the panel of genes thereby validating the perturbational effect of the test chemical compound.

2. The method of claim 1, wherein the control solution is a polar aprotic solvent or a mixture of polar aprotic solvents.

3. The method of claim 1, wherein the control solution is dimethyl sulfoxide, N,N-dimethylformamide, acetonitrile, acetone or a mixture thereof.

4. The method of claim 1, wherein each respective abundance value in the plurality of abundance values is a measure of central tendency of the abundance value of the corresponding cellular constituent across the first plurality of cells in the one or more reference assay experiments.

5. The method of claim 1, wherein the plurality of abundance values is obtained in the one or more reference assay experiments by single-cell ribonucleic acid (RNA) sequencing (scRNA-seq).

6. The method of claim 1, wherein each cellular constituent in the set of cellular constituents uniquely maps to a different gene.

7. The method of claim 1, wherein each cellular constituent in the plurality of cellular constituents is a particular gene, a particular mRNA associated with a gene, a carbohydrate, a lipid, an epigenetic feature, a metabolite, an antibody, a peptide a protein, or a post-translational modification of a protein.

8. The method of claim 1, wherein the set of cellular constituents comprises 10 or more cellular constituents, 20 or more cellular constituents, 30 or more cellular constituents, 40 or more cellular constituents, or 50 or more cellular constituents.

9. The method of claim 1, wherein the set of cellular constituents consists of between 10 and 200 cellular constituents.

10. The method of claim 1, wherein the first model is a logistic regression model.

11. The method of claim 1, wherein the first model is an algorithm for gradient boosting on decision trees.

12. The method of claim 1, wherein the first plurality of cells are cells from an organ, cells from a tissue, a plurality of stem cells, a plurality of primary human cells, cells from umbilical cord blood, cells from peripheral blood, bone marrow cells, cells from a solid tissue, or a plurality of differentiated cells.

13. The method of claim 1, the method further comprising calculating the fingerprint of the chemical structure of a test chemical compound in the plurality of test chemical compounds from a string representation of the test chemical compound.

14. The method of claim 1, the method further comprising generating the fingerprint of the chemical structure of a test chemical compound in the plurality of test chemical compounds from a chemical structure of the test chemical compound using one or more featurizers.

15. The method of claim 1, wherein the plurality of abundance values is determined by a colorimetric measurement, a fluorescence measurement, a luminescence measurement, a resonance energy transfer (FRET) measurement, a measurement of a protein-protein interaction, a measurement of a protein-polynucleotide interaction, a measurement of a protein-small molecule interaction, mass spectrometry, nuclear magnetic resonance, or a microarray measurement.

16. The method of claim 1, wherein each test chemical compound in the plurality of test chemical compounds is a first organic compound having a molecular weight of less than 2000 Daltons, and the reference chemical compound is a second organic compound having a molecular weight of less than 2000 Daltons.

17. The method of claim 1, wherein each test chemical compound in the plurality of test chemical compounds satisfies any two or more rules, any three or more rules, or all four rules of the Lipinski's rule of Five: (i) not more than five hydrogen bond donors, (ii) not more than ten hydrogen bond acceptors, (iii) a molecular weight under 500 Daltons, and (iv) a Log P under 5.

18. The method of claim 1, wherein the reference compound alleviates a condition in a subject, and the method further comprises:
administering the test chemical compound in the subset of test chemical compounds to the subject as a treatment to alleviate the condition in the subject.

19. The method of claim 18, wherein the treatment comprises a composition comprising the test chemical compound and one or more excipient and/or one or more pharmaceutically acceptable carrier and/or one or more diluent.

20. The method of claim 18, wherein the condition is inflammation or pain.

21. The method of claim 18, wherein the condition is a disease.

22. The method of claim 1, the method further comprising training the first model.

23. The method of claim 22, wherein the first model comprises a first plurality of parameters and wherein the training comprises, for each respective training compound in a plurality of training compounds, performing a procedure comprising:
(i) obtaining a respective training fingerprint of a chemical structure of the respective training compound;
(ii) responsive to inputting the respective fingerprint of the chemical structure of the respective training compound and the plurality of abundance values for each cellular constituent in the set of cellular constituents across the first plurality of cells into the first model, retrieving, as respective training output from the first model, a corresponding training predicted similarity between (a) a predicted perturbational effect of the respective training compound across the set of cellular constituents and (b) a measured cell-based perturbational effect of the reference chemical compound across the set of cellular constituents;
(iii) applying a respective difference to a loss function to obtain a respective output of the loss function, wherein the respective difference is between (a) the corresponding training predicted similarity from the first model and (b) a score from a second model that indicates whether, or to what degree, a predicted perturbational effect of the respective training compound across the set of cellular constituents matches a measured cell-based perturbational effect of the reference chemical compound across the set of cellular constituents; and
(iv) using the respective output of the loss function to adjust the first plurality of parameters.

24. The method of claim 23, wherein the score from the second model is obtained by inputting a vector of abundance values into a second model, wherein each element in the vector of abundance values is a difference between:
(a) an abundance of a corresponding cellular constituent in the set of cellular constituents in a corresponding reference cell-based assay upon exposure to the respective training compound solvated in the control solution; and
(b) an abundance of a corresponding cellular constituent in the set of cellular constituents in a corresponding reference cell-based assay upon exposure to the control solution free of the respective training compound.

25. The method of claim 22, wherein the second model is a logistic regression model or a random forest model.

26. The method of claim 1, wherein the predicted perturbational effect is selected from the group consisting of an IC50, a measure of differential gene expression, a log fold change, a ddCq value, a measure of apoptosis, a staining intensity, a textural pattern, a size of a cell or a cellular structure thereof, a shape of a cell or a cellular structure thereof, and any correlation or adjacency relationship thereof.

27. The method of claim 1, wherein the panel of genes comprises SLCO5A1, APOL4, FAM19A2, HSPA8, OSM, SH3BP5, CFH, WFDC2, TMEM176A, VMP1, S100A9, ENPP2, CISH, NPDC1, ENPP3, MYC, CKAP4, EIF5, IFITM2, or EIF4A1.

28. A method of screening a plurality of test chemical compounds against a reference compound, the method comprising:
(A) obtaining a fingerprint of a chemical structure of each test chemical compound in the plurality of test chemical compounds, wherein the plurality of test chemical compounds comprises at least ten thousand test chemical compounds;
(B) for each test chemical compound in the plurality of test chemical compounds, responsive to inputting the fingerprint of the chemical structure of the test chemical compound into a first model, retrieving, as output from the first model, a predicted perturbational effect of the test chemical compound thereby identifying a subset of the plurality of test chemical compounds in the plurality of test chemical compounds that have a perturbation effect that is similar to the reference compound and wherein the first model comprises a first plurality of parameters; and
(C) exposing a first plurality of cells to a test chemical compound in the subset of the plurality of test chemical compounds, wherein the test chemical compound has a Tanimoto coefficient of less than 0.85 with respect to the reference chemical compound;
(E) measuring a transcriptional response of each gene in a panel of genes in the first plurality of cells after the exposing (C);
(F) exposing a second plurality of cells to the reference compound;
(G) measuring a transcriptional response of each gene in the panel of genes in the second plurality of cells after the exposing (F); and
(H) determining that a transcriptional response to the test compound and the reference compound is similar across the panel of genes thereby validating a perturbational effect of the test chemical compound in the subset of the plurality of test chemical compounds.

29. The method of claim 28, wherein the first model comprises a first plurality of parameters, and wherein the method further comprises training the first model by a procedure comprising:
for each respective training compound in a plurality of training compounds:
(i) obtaining a respective training fingerprint of a chemical structure of the respective training compound;
(ii) responsive to inputting the respective fingerprint of the chemical structure of the respective training compound into the first model, retrieving, as respective training output from the first model, a corresponding training predicted perturbational effect of the respective training compound;
(iii) applying a respective difference to a loss function to obtain a respective output of the loss function, wherein the respective difference is between (a) the corresponding training predicted perturbational effect of the respective training compound from the first model and (b) a reference perturbational effect of the respective training compound, wherein the reference perturbational effect of the respective training compound is (i) a measured reference perturbational effect obtained from a reference cell-based assay, or (ii) a predicted reference perturbational effect predicted by a second model; and
(iv) using the respective output of the loss function to adjust the first plurality of parameters.

30. The method of claim 28, wherein the reference compound alleviates a condition in a subject, and the method further comprises:
administering the test chemical compound in the subset of test chemical compounds to the subject as a treatment to alleviate the condition in the subject.

31. The method of claim 30, wherein the treatment comprises a composition comprising the test chemical compound and one or more excipient and/or one or more pharmaceutically acceptable carrier and/or one or more diluent.

32. The method of claim 28, wherein the panel of genes comprises SLCO5A1, APOL4, FAM19A2, HSPA8, OSM, SH3BP5, CFH, WFDC2, TMEM176A, VMP1, S100A9, ENPP2, CISH, NPDC1, ENPP3, MYC, CKAP4, EIF5, IFITM2, or EIF4A1.

* * * * *